US007226769B2

(12) United States Patent
Lambeth et al.

(10) Patent No.: US 7,226,769 B2
(45) Date of Patent: Jun. 5, 2007

(54) DUAL OXIDASES AS MITOGENIC AND ENDOCRINE REGULATORS

(75) Inventors: J. David Lambeth, Decatur, GA (US); Bernard P. Lassegue, Decatur, GA (US); Kathy K. Griendling, Stone Mountain, GA (US); Rebecca S. Arnold, Lilburn, GA (US); Guangjie Cheng, Atlanta, GA (US); Lisa Sharling, Scotland (GB); Guy Benian, Decatur, GA (US); William A. Edens, Tucker, GA (US)

(73) Assignee: Emory University, Atlanta, GA (US)

( * ) Notice: Subject to any disclaimer, the term of this patent is extended or adjusted under 35 U.S.C. 154(b) by 430 days.

(21) Appl. No.: 10/276,153

(22) PCT Filed: May 14, 2001

(86) PCT No.: PCT/US01/15573

§ 371 (c)(1),
(2), (4) Date: Aug. 7, 2003

(87) PCT Pub. No.: WO01/87957

PCT Pub. Date: Nov. 22, 2001

(65) Prior Publication Data

US 2005/0089844 A1    Apr. 28, 2005

Related U.S. Application Data

(63) Continuation-in-part of application No. 09/437,568, filed on Nov. 10, 1999, now Pat. No. 6,620,603.

(60) Provisional application No. 60/222,421, filed on Aug. 1, 2000, provisional application No. 60/204,441, filed on May 15, 2000, provisional application No. 60/151,242, filed on Aug. 27, 1999, provisional application No. 60/149,332, filed on Aug. 17, 1999, provisional application No. 60/107,911, filed on Nov. 10, 1998.

(51) Int. Cl.
*C12N 9/08* (2006.01)
*C12N 9/00* (2006.01)
*C12N 9/02* (2006.01)
*C12P 21/06* (2006.01)
*C12Q 1/68* (2006.01)

(52) U.S. Cl. .................. 435/192; 435/69.1; 435/6; 435/183; 435/189; 435/320.1; 435/252.3; 435/325; 536/23.2

(58) Field of Classification Search ............... 536/23.1, 536/23.2; 435/320.1, 183, 68.1, 6, 69.1, 435/189, 252.3, 325
See application file for complete search history.

(56) References Cited

U.S. PATENT DOCUMENTS 5,593,966 A    1/1997 Malech et al.

6,620,603 B1 *  9/2003 Lambeth et al. ............ 435/189

OTHER PUBLICATIONS

International Search Report dated Aug. 16, 2000 for PCT/US 99/26592.
Li, F. et al.: "CD34+Peripheral Blood Progenitors as a Target for Genetic Correction of the Two Flavocytochrome B558 Defective Forms of Chronic Granulomatous Disease," Blood, US, W.B. Saunders, Philadelphia, VA, vol. 84, No. 1, Jul. 1, 1994, pp. 53-58, XP000674233 ISSN: 0006-4971, p. 54, col. 2, figures 1, 2.
Strausberg et al., "National cancer institute, cancer genome anatomy project (CGAP)," EMBL Database Acc No. AA493362, Jun. 28, 1997, XP002137597.
Lloyd: "Human DNA sequence from clone 146h21 on chromosome Xq22," EMBL Database Acc. No. Z83819, Jan. 10, 1997, XP002137598.
Adams et al.: "Initial assessment of human gene diversity and expression patterns based upon 83 million basepairs of cDNA sequence," EMBL Database Acc No. AA305700, Apr. 18, 1997, XP002137621 cited in the application.
Palmer: "Human DNA sequence from clone 257I9 on chromosome 6q25.1-26 contains gene similar to Cytochrome B, CA repeat, GSS" EMBL Database Acc. No. AL031773, Sep. 29, 1998, XP002144975.
Hillier et al.: "Generation and analysis of 280,000 human expressed sequence tags," EMBL Database Acc. No. W52750, Jun. 4, 1996, XP002144976.
Strausberg: "National cancer institute, cancer genome anatomy project (CGAP)" EMBL Database Acc. No. AA641653, Nov. 1, 1997, XP002144977.
Wilson et al.: "f53g12.3" EMBL Database Acc. No. AF003139, Jul. 1, 1997, XP002144978, abstract.
Suh et al.: "Cell transformation by the superoxide-generating oxidase Mox1" Nature, vol. 401, Sep. 2, 1999, pp. 79-82, XP002137599.
Dupuy et al.: "Purification of a novel flavoprotein involved in the thyroid NADPH oxidase," The Journal of Biological Chemistry, vol. 274, No. 52, Dec. 24, 1999, pp. 37265-37269, XP002144979.
Dupuy et al.: EMBL Database Acc. No. AF181972, Dec. 29, 1999, XP002144980.
Abdelrahim, M., et al., "Liquid chromatographic assay of dityrosin in human cerebrospinal fluid," J. Chromatogr. B. Biomed. Sci. Appl., vol. 696, pp. 175-182 (1997).

(Continued)

*Primary Examiner*—Rebecca E. Prouty
*Assistant Examiner*—Ganapathirama Raghu
(74) *Attorney, Agent, or Firm*—Klarquist Sparkman, LLP

(57) ABSTRACT

The present invention relates to new genes encoding for the production of novel proteins involved in generation of reactive oxygen intermediates and in peroxidative reactions that affect biological functions including cell division, thyroid hormone biosynthesis and tissue fibrosis. The present invention also provides vectors containing these genes, cells transfected with these vectors, antibodies raised against these novel proteins, kits for detection, localization and measurement of these genes and proteins, and methods to determine the activity of drugs to affect the activity of the proteins of the present invention.

21 Claims, 8 Drawing Sheets

OTHER PUBLICATIONS

Anderson, S.O., "Covalent cross-links in a structural protein, resilin," Acta Physiol. Scand., vol. 66 Suppl. 263, pp. 1-81 (1966).

Burdon, R.H., "Superoxide and hydrogen peroxide in relation to mammalian cell proliferation," Free Radical Biol. Med., vol. 18, No. 4, pp. 775-794 (1995).

Church, S.L., et al., "Increased managanese superoxide dismutase expression suppresses the malignant phenotype of human melanoma cells," Proc. Natl. Acad. Sci. USA, vol. 90, pp. 3113-3117 (1993).

Emmendörffer, A., et al., "Production of oxygen radicals by fibroblasts and neutrophils from a patient with x-linked chronic granulomatous disease," Eur. J. Haematol, vol. 51, pp. 223-227 (1993).

Fernandez-Pol, J.A., et al., "Correlation between the loss of the transformed phenotype and an increase in superoxide dismutase activity in a revertant subclone of sarcoma virus-infected mammalian cells," Can. Res., vol. 42, pp. 609-617 (1982).

Fire, A., et al., "Potent and specific genetic interference by double-stranded RNA in Caenorhabditis elegans," Nature, vol. 391, No. 6669, pp. 806-811 (1998).

Frohman, M.A., et al., "Rapid production of full-length cDNAs from rare transcripts: Amplification using a single gene-specific oligonucleotide primer," Proc. Natl. Acad. Sci. USA, vol. 85, pp. 8998-9002 (1988).

Fukui, T., et al., "p22phox mRNA expression and NADPH oxidase activity are increased in aortas from hypertensive rats," Cir. Res., vol. 80, No. 1, pp. 45-51 (1997).

Gardner, P.R., et al., "Superoxide radical and iron modulate aconitase activity in mammalian cells," J. Biol. Chem., vol. 270, No. 22, pp. 13399-13405 (1995).

Griendling, K. K., et al., "Angiotensin II stimulates NADH and NADPH oxidase activity in cultured vascular smooth muscle cells," Cir. Res., vol. 74, No. 6, pp. 1141-1148 (1994).

Irani, K., et al., "Mitogenic signaling mediated by oxidants in ras-transformed fibroblasts," Science, vol. 275, No. 5306, pp. 1649-1652 (1997).

Li, Y., et al., "Validation of lucigenin (Bis-N-methylacridinium) as a chemilumigenic probe for detecting superoxide anion radical production by enzymatic and cellular systems," J. Biol. Chem., vol. 273, No. 4, pp. 2015-2023 (1998).

Mastsubara, T., et al., "Increased superoxide anion release from human endothelial cells in response to cytokines," J. Immun., vol. 137, No. 10, pp. 3295-3298 (1986).

Meier, B., et al., "Human fibroblasts release reactive oxygen species in response to interleukin-1 or tumor necrosis factor-α," Biochem. J., vol. 263, No. 2, pp. 539-545 (1989).

Pagano, P. J., et al., "Localization of a constitutively active, phagocyte-like NADPH oxidase in rabbit aortic adventitia: Enhancement by angiotensin II," Proc. Natl. Acad. Sci. USA, vol. 94, No. 26, pp. 14483-14488 (1997).

Schmidt, K. N., et al., "The roles of hydrogen peroxide and superoxide as messengers in the activation of transcription factor NF-κB ," Chem & Bio., vol. 2, No. 1, pp. 13-22 (1995).

Schreck, R., et al., "Reactive oxygen intermediates as apparently widely used messengers in the activation of the NF-κB transcription factor and HIV-1," EMBO J., vol. 10, No. 8, pp. 2247-2258 (1991).

Suh, Y., et al., "Cell transformation by the superoxide-generating oxidase Mox1," Nature, vol. 401, No. 6748, pp. 79-82 (1999).

Sundaresan, M., et al., "Requirement for generation of $H_2O_2$ for platelet-derived growth factor signal transduction," Science, vol. 270, pp. 296-299 (1995).

Szatrowski, T.P., et al., "Production of large amounts of hydrogen peroxide by human tumor cells," Canc. Res., vol. 51, No. 3, pp. 794-798 (1991).

Uhlinger, D.J., "Nucleoside triphosphate requirements for superoxide generation and phosphorylation in a cell-free system from human neutrophils," vol. 266, No. 31, pp. 20990-20997 (1991).

Ushio-Fukai M., et al., "$p22^{phox}$ is a critical component of the superoxide-generating NADH/NADPH oxidase system and regulates angiotensin II-induced hypertrophy in vascular smooth muscle cells," J. Biol. Chem., vol. 271, No. 38, pp. 23317-23321 (1996).

Yan, T., et al., "Manganese-containing superoxide dismutase overexpression causes phenotypic reversion in SV40-transformed human lung fibroblasts," Canc. Res., vol. 56, pp. 2864-2871 (1996).

Yu, L., et al., Biosynthesis of the phagocyte NADPH oxidase cytochrome $b_{558}$, J. Biol. Chem., vol. 272, No. 43, pp. 27288-27294 (1997).

* cited by examiner

DUAL OXIDASES AS MITOGENIC AND ENDOCRINE REGULATORS

PRIOR RELATED APPLICATIONS

This application is the National Stage of International Application No. PCT/US01/15573, filed May 14, 2001, which claims the benefit of U.S. Provisional Application No. 60/204,441, filed May 15, 2000, and U.S. Provisional Application No. 60/222,421, filed Aug. 1, 2000. This application is also a Continuation-in-Part of U.S. patent application Ser. No. 09/437,568, filed Nov. 10, 1999 now U.S. Pat. No. 6,620,603, which claims the benefit of U.S. Provisional Application No. 60/107,911, filed Nov. 10. 1998, U.S. Provisional Application No. 60/151,242, filed Aug. 27, 1999, and U.S. Provisional Application No. 60/149,332, filed Aug. 17, 1999.

TECHNICAL FIELD

The present invention relates to the fields of normal and abnormal cell growth, in particular mitogenic regulation, to thyroid hormone biosynthesis and to nematode cuticle biogenesis. The present invention provides the following: nucleotide sequences encoding for the production of enzymes that are mitogenic regulators, that catalyze thyroid hormone biosynthesis and in nematodes catalyze the biogenesis of cuticle; amino acid sequences of these enzymes; vectors containing these nucleotide sequences; methods for transfecting cells with vectors that produce these enzymes; and antibodies to these enzymes that are useful for detecting and measuring levels of these enzymes, and for binding to cells possessing extracellular epitopes of these enzymes.

BACKGROUND OF THE INVENTION

Reactive oxygen intermediates (ROI) are partial reduction products of oxygen: 1 electron reduces $O_2$ to form superoxide ($O_2^-$), and 2 electrons reduce $O_2$ to form hydrogen peroxide ($H_2O_2$). ROI are generated as a byproduct of aerobic metabolism and by toxicological mechanisms. There is growing evidence for regulated enzymatic generation of $O_2^-$ and its conversion to $H_2O_2$ in a variety of cells. The conversion of $O_2^-$ to $H_2O_2$ occurs spontaneously, but is markedly accelerated by superoxide dismutase (SOD). High levels of ROI are associated with damage to biomolecules such as DNA, biomembranes and proteins. Recent evidence indicates generation of ROI under normal cellular conditions and points to signaling and metabolic roles for $O_2^-$ and $H_2O_2$.

Several biological systems generate reactive oxygen. Phagocytic cells such as neutrophils generate large quantities of ROI as part of their battery of bactericidal mechanisms. Exposure of neutrophils to bacteria or to various soluble mediators such as formyl-Met-Leu-Phe or phorbol esters activates a massive consumption of oxygen, termed the respiratory burst, to initially generate superoxide, with secondary generation of $H_2O_2$, HOCl and hydroxyl radical. The enzyme responsible for this oxygen consumption is the respiratory burst oxidase (nicotinamide adenine dinucleotide phosphate-reduced form (NADPH) oxidase).

There is growing evidence for the generation of ROI by non-phagocytic cells, particularly in situations related to cell proliferation. In addition in some tissues such as thyroid, ROI generation is implicated in metabolic conversions such as the biosynthesis of thyroid hormone. Significant generation of $H_2O_2$, $O_2^-$, or both have been noted in some cell types. Fibroblasts and human endothelial cells show increased release of superoxide in response to cytokines such as interleukin-1 or tumor necrosis factor (TNF) (Meier et al. (1989) *Biochem J.* 263, 539–545.; Matsubara et al. (1986) *J. Immun.* 137, 3295–3298). Ras-transformed fibroblasts show increased superoxide release compared with control fibroblasts (Irani, et al. (1997) *Science* 275, 1649–1652). Rat vascular smooth muscle cells show increased $H_2O_2$ release in response to PDGF (Sundaresan et al. (1995) *Science* 270, 296–299) and angiotensin II (Griendling et al. (1994) *Circ. Res.* 74, 1141–1148; Fukui et al. (1997) *Circ. Res.* 80, 45–51; Ushio-Fukai et al. (1996) *J. Biol. Chem.* 271, 23317–23321), and $H_2O_2$ in these cells is associated with increased proliferation rate. The occurrence of ROI in a variety of cell types is summarized in Table 1 (adapted from Burdon, R. (1995) *Free Radical Biol. Med.* 18, 775–794).

TABLE 1

| Superoxide | Hydrogen Peroxide |
|---|---|
| human fibroblasts | Balb/3T3 cells |
| human endothelial cells | rat pancreatic isletcells |
| human/rat smooth muscle cells | murine keratinocytes |
| human fat cells | rabbit chondrocytes |
| human osteocytes | human tumor cells |
| BHK-21 cells | fat cells, 3T3 L1 cells |
| human colonic epithelial cells | |

ROI generated by the neutrophil have a cytotoxic function. While ROI are normally directed at the invading microbe, ROI can also induce tissue damage (e.g., in inflammatory conditions such as arthritis, shock, lung disease, and inflammatory bowel disease) or may be involved in tumor initiation or promotion, due to damaging effects on DNA. Nathan (Szatrowski et al. (1991) *Canc. Res.* 51, 794–798) proposed that the generation of ROI in tumor cells may contribute to the hypermutability seen in tumors, and may therefore contribute to tumor heterogeneity, invasion and metastasis.

In addition to cytotoxic and mutagenic roles, ROI have ideal properties as signal molecules: 1) they are generated in a controlled manner in response to upstream signals; 2) the signal can be terminated by rapid metabolism of $O_2^-$ and $H_2O_2$ by SOD and catalase/peroxidases; 3) they elicit downstream effects on target molecules, e.g., redox-sensitive regulatory proteins such as NF kappa B and AP-1 (Schreck et al. (1991) *EMBO J.* 10, 2247–2258; Schmidt et al. (1995) *Chemistry & Biology* 2, 13–22). Oxidants such as $O_2^-$ and $H_2O_2$ have a relatively well defined signaling role in bacteria, operating via the SoxI/II regulon to regulate transcription.

ROI appear to have a direct role in regulating cell division, and may function as mitogenic signals in pathological conditions related to growth. These conditions include cancer and cardiovascular disease. $O_2^-$ is generated in endothelial cells in response to cytokines, and might play a role in angiogenesis (Matsubara et al. (1986) *J. Immun.* 137, 3295–3298). $O_2^-$ and $H_2O_2$ are also proposed to function as "life-signals", preventing cells from undergoing apoptosis (Matsubara et al. (1986) *J. Immun.* 137, 3295–3298). As discussed above, many cells respond to growth factors (e.g., platelet derived growth factor (PDGF), epidermal derived growth factor (EGF), angiotensin II, and various cytokines) with both increased production of $O_2^-$/$H_2O_2$ and increased proliferation. Inhibition of ROI generation prevents the mitogenic response. Exposure to exogenously generated $O_2^-$ and $H_2O_2$ results in an increase in cell proliferation. A partial list of responsive cell types is shown below in Table 2 (adapted from Burdon, R. (1995) *Free Radical Biol. Med.* 18, 775–794).

TABLE 2

| Superoxide | Hydrogen peroxide |
| --- | --- |
| human, hamster fibroblasts | mouse osteoblastic cells |
| Balb/3T3 cells | Balb/3T3 cells |
| human histiocytic leukemia | rat, hamster fibroblasts |
| mouse epidermal cells | human smooth muscle cells |
| rat colonic epithelial cells | rat vascular smooth muscle cells |
| rat vascular smooth muscle cells | |

While non-transformed cells can respond to growth factors and cytokines with the production of ROI, tumor cells appear to produce ROI in an uncontrolled manner. A series of human tumor cells produced large amounts of hydrogen peroxide compared with non-tumor cells (Szatrowski et al. (1991) *Canc. Res.* 51, 794–798). Ras-transformed NIH 3T3 cells generated elevated amounts of superoxide, and inhibition of superoxide generation by several mechanisms resulted in a reversion to a "normal" growth phenotype.

$O_2^-$ has been implicated in maintenance of the transformed phenotype in cancer cells including melanoma, breast carcinoma, fibrosarcoma, and virally transformed tumor cells. Decreased levels of the manganese form of SOD (MnSOD) have been measured in cancer cells and in vitro-transformed cell lines, predicting increased $O_2^-$ levels (Burdon, R. (1995) *Free Radical Biol. Med.* 18, 775–794). MnSOD is encoded on chromosome 6q25 which is very often lost in melanoma. Overexpression of MnSOD in melanoma and other cancer cells (Church et al. (1993) *Proc. of Natl. Acad. Sci.* 90, 3113–3117; Fernandez-Pol et al. (1982) *Canc. Res.* 42, 609–617; Yan et al. (1996) *Canc. Res.* 56, 2864–2871) resulted in suppression of the transformed phenotype.

ROI are implicated in growth of vascular smooth muscle associated with hypertension, atherosclerosis, and restenosis after angioplasty. $O_2^-$ generation is seen in rabbit aortic adventitia (Pagano et al. (1997) *Proc. Natl. Acad. Sci.* 94, 14483–14488). Vascular endothelial cells release $O_2^-$ in response to cytokines (Matsubara et al. (1986) *J. Immun.* 137, 3295–3298). $O_2^-$ is generated by aortic smooth muscle cells in culture, and increased $O_2^-$ generation is stimulated by angiotensin II which also induces cell hypertrophy. In a rat model system, infusion of angiotensin II leads to hypertension as well as increased $O_2^-$ generation in subsequently isolated aortic tissue (Ushio-Fukai et al. (1996) *J. Biol. Chem.* 271, 23317–23321.; Yu et al. (1997) *J. Biol. Chem.* 272, 27288–27294). Intravenous infusion of a form of SOD that localizes to the vasculature or an infusion of an $O_2^-$ scavenger prevented angiotensin II induced hypertension and inhibited ROI generation (Fukui et al. (1997) *Circ. Res.* 80, 45–51).

The neutrophil NADPH oxidase, also known as phagocyte respiratory burst oxidase, provides a paradigm for the study of the specialized enzymatic ROI-generating system. This extensively studied enzyme oxidizes NADPH and reduces oxygen to form $O_2^-$. NADPH oxidase consists of multiple proteins and is regulated by assembly of cytosolic and membrane components. The catalytic moiety consists of flavocytochrome $b_{558}$, an integral plasma membrane enzyme comprised of two components: gp91phox (gp refers to glycoprotein; phox is an abbreviation of the words phagocyte and oxidase) and p22phox (p refers to protein). gp91phox contains 1 flavin adenine dinucleotide (FAD) and 2 hemes as well as the NADPH binding site.

p22phox has a C-terminal proline-rich sequence which serves as a binding site for cytosolic regulatory proteins. The two cytochrome subunits, gp91phox and p22phox appear to stabilize one another, since the genetic absence of either subunit, as in the inherited disorder chronic granulomatous disease (CGD), results in the absence of the partner subunit (Yu et al. (1997) *J. Biol. Chem.* 272. 27288–27294). Essential cytosolic proteins include p47phox, p67phox and the small GTPase Rac, of which there are two isoforms. p47phox and p67phox both contain $SH_3$ regions and proline-rich regions which participate in protein interactions governing assembly of the oxidase components during activation. The neutrophil enzyme is regulated in response to bacterial phagocytosis or chemotactic signals by phosphorylation of p47phox, and perhaps other components, as well as by guanine nucleotide exchange to activate the GTP-binding protein Rac.

The origin of ROI in non-phagocytic tissues is unproven, but the occurrence of phagocyte oxidase components has been evaluated in several systems by immunochemical methods, Northern blots and reverse transcriptase-polymerase chain reaction (RT-PCR). The message for p22phox is expressed widely, as is that for Rac1. Several cell types that are capable of $O_2^-$ generation have been demonstrated to contain all of the phox components including gp91phox, as summarized below in Table 3. These cell types include endothelial cells, aortic adventitia and lymphocytes.

TABLE 3

| Tissue | gp91phox | p22phox | p47phox | p67phox |
| --- | --- | --- | --- | --- |
| neutrophil | $+^{1,2}$ | $+^{1,2}$ | $+^{1,2}$ | $+^{1,2}$ |
| aortic adventitia | $+^1$ | $+^1$ | $+^1$ | $+^1$ |
| lymphocytes | $+^2$ | $+^2$ | $+^{1,2}$ | $+^{1,2}$ |
| endothelial cells | $+^2$ | $+^2$ | $+^{1,2}$ | $+^{1,2}$ |
| glomerular mesangial cells | — | $+^{1,2}$ | $+^{1,2}$ | $+^{1,2}$ |
| fibroblasts | — | $+^2$ | $+^{1,2}$ | $+^2$ |
| aortic sm. muscle | — | $+^{1,2}$ | ? | ? |

[1] = protein expression shown.
[2] = mRNA expression shown.

A distinctly different pattern is seen in several other cell types shown in Table 3 including glomerular mesangial cells, rat aortic smooth muscle and fibroblasts. In these cells, expression of gp91phox is absent while p22phox and in some cases cytosolic phox components have been demonstrated to be present. Since gp91phox and p22phox stabilize one another in the neutrophil, there has been much speculation that some molecule, possibly related to gp91phox, accounts for ROI generation in glomerular mesangial cells, rat aortic smooth muscle and fibroblasts (Ushio-Fukai et al. (1996) *J. Biol. Chem.* 271, 23317–23321). Investigation of fibroblasts from a patient with a genetic absence of gp91phox provides proof that the gp91phox subunit is not involved in ROI generation in these cells (Emmendorffer et al. (1993) *Eur. J. Haematol.* 51, 223–227). Depletion of p22phox from vascular smooth muscle using an antisense approach indicated that this subunit participates in ROI generation in these cells, despite the absence of detectable gp91phox (Ushio-Fukai et al. (1996) *J. Biol. Chem.* 271, 23317–23321).

Thyroid hormone regulates basal metabolic rate through end-effects on mitochondrial respiration, and conditions of under- or over-production are important clinically. Development of drugs to regulate the biosynthesis of thyroid hormone is a medically important goal, and identification of the enzymes in this pathway is key to developing pharmacologically relevant targets. Thyroid uniquely concentrates iodide, which is used to iodinate tyrosine residues on thyroglobulin (TG). TG is a large protein (660 kDa) that contains 67 tyrosyl residues, some of which are preferential sites for iodination. Iodination of tyrosines in TG is catalyzed by thyroid peroxidase (TPO), a plasma membrane hemoprotein. Iodination requires a previously unidentified enzymatic source of $H_2O_2$. A second step is the coupling of two diiodotyrosines (DIT) to form protein-associated thyroxine (T4), which is subsequently proteolytically cleaved from TG to liberate free T4. What is needed is a composition of the gene that encodes the enzyme that generates $H_2O_2$ in thyroid and that catalyzes the coupling reaction, and a method of using that composition to modulate thyroid hormone biosynthesis. Such information would be useful in the development of drugs for modulation of thyroid function. Such modulation might be useful in the treatment of hyperthyroidism.

Recent evidence suggests that enzymes involved in oxidative cross-linking of tyrosine in growth factor stimulated fibroblasts may lead to fibrotic damage. Lung fibrosis is particularly damaging to individuals afflicted with this condition. Identification of the genes encoding enzymes involved in such oxidative cross-linking reactions is needed so that drugs may be designed to alleviate or prevent fibrotic damage, particularly in the lung.

Parasitic diseases are a major cause of morbidity and mortality worldwide in humans and animals, and have a significant impact on agricultural productivity as well. Parasitic diseases have proven difficult to treat, in part due to the presence of the cuticle, a tough exoskeletal structure of parasites such as nematodes. What is needed is a composition and method of using the composition to fight parasitic diseases, including but not limited to those parasitic diseases caused by parasites with cuticles.

Accordingly, what is needed is a method of disrupting the formation of the cuticle which would make the worm susceptible to the host defense mechanisms and drug treatment.

What is also needed is the identity of the proteins involved in ROI generation, especially in non-phagocytic tissues and cells. What is also needed are the nucleotide sequences encoding for these proteins, and the primary sequences of the proteins themselves. Also needed are vectors designed to include nucleotides encoding for these proteins. Probes and PCR primers derived from the nucleotide sequence are needed to detect, localize and measure nucleotide sequences, including mRNA, involved in the synthesis of these proteins. In addition, what is needed is a means to transfect cells with these vectors. What is also needed are expression systems for production of these molecules. Also needed are antibodies directed against these molecules for a variety of uses including localization, detection, and measurement and passive immunization.

SUMMARY OF THE INVENTION

The present invention solves the problems described above by providing a novel family of nucleotide sequences and proteins encoded by these nucleotide sequences termed duox proteins. In particular, the present invention provides compositions comprising the nucleotide sequences SEQ ID NO: 1 and SEQ ID NO: 3, and fragments and conservative substitutions thereof, which encode for the expression of proteins comprising SEQ ID NO: 2 and SEQ ID NO: 4 respectively, and fragments and conservative substitutions thereof Preferred protein fragments include, but are not limited to, SEQ ID NO: 31 and SEQ ID NO: 32. While not wanting to be bound by the following statement, it is believed that these proteins are involved in ROI production and are capable of stimulating superoxide production or generating peroxidative reactions. The present invention also provides vectors containing these nucleotide sequences, cells transfected with these vectors which produce the proteins comprising SEQ ID NO: 2 and SEQ ID NO: 4, and fragments and conservative substitutions thereof, and antibodies to these proteins and fragments and conservative substitutions thereof The present invention also provides methods for stimulating cellular proliferation by administering vectors encoded for production of the proteins comprising SEQ ID NO: 2 and SEQ ID NO: 4 and fragments and conservative substitutions thereof The present invention also provides methods for stimulating cellular proliferation by administering the proteins comprising SEQ ID NO: 2 and SEQ ID NO: 4 and fragments and conservative substitutions thereof. The proteins comprising SEQ ID NO: 2 and SEQ ID NO: 4 and fragments and conservative substitutions thereof are useful in affecting the exoskeleton, especially the cuticle of parasites, including but not limited to nematodes. The nucleotides and antibodies of the present invention are useful for the detection, localization and measurement of the nucleic acids encoding for the production of the proteins of the present invention, and also for the detection, localization and measurement of the proteins of the present invention. These nucleotides and antibodies can be combined with other reagents in kits for the purposes of detection, localization and measurement.

Most particularly, the present invention involves a method for regulation of cell division or cell proliferation by modifying the activity or expression of the duox proteins described as SEQ ID NO: 2 and SEQ ID NO: 4 or fragments or conservative substitutions thereof. These proteins, in their naturally occurring or expressed forms, are expected to be useful in drug development, for example for screening of chemical and drug libraries by observing inhibition of the activity of these enzymes. Such chemicals and drugs would likely be useful as treatments for cancer, prostatic hypertrophy, benign prostatic hypertrophy, hypertension, metabolic disease, fibrosis, atherosclerosis and many other disorders involving abnormal cell growth or proliferation, and a variety of parasitic diseases in both animals and crops as described below. The entire expressed protein may be useful in these assays. Portions of the molecule which may be targets for inhibition or modification include but are not limited to the binding site for pyridine nucleotides (NADPH or NADH), the flavoprotein domain (approximately the C-terminal 265 amino acids), and/or the binding or catalytic site for flavin adenine dinucleotide (FAD).

The method of the present invention may be used for the development of drugs or other therapies for the treatment of conditions associated with abnormal growth including, but not limited to the following: cancer, fibrosis, lung fibrosis, metabolic imbalances, thyroid imbalances, hyperthryoidism, psoriasis, prostatic hypertrophy, benign prostatic hypertrophy, cardiovascular disease, proliferation of vessels, including but not limited to blood vessels and lymphatic vessels, arteriovenous malformation, vascular problems associated with the eye, atherosclerosis, hypertension, and restenosis following angioplasty and parasitic diseases. The enzymes of the present invention are excellent targets for the development of drugs and other agents which may modulate the activity of these enzymes. It is to be understood that modulation of activity may result in enhanced, diminished or absence of enzymatic activity. Modulation of the activity of these enzymes may be useful in treatment of conditions, including but not limited to conditions associated with abnormal growth, metabolic disorders, and fibrosis.

Drugs which affect the activity of the duox enzymes represented in SEQ ID NO: 2 and SEQ ID NO: 4, or fragments or conservative substitutions thereof, may also be combined with other therapeutics in the treatment of specific conditions. For example, these drugs may be combined with angiogenesis inhibitors in the treatment of cancer, with antihypertensives for the treatment of hypertension, with cholesterol lowering drugs for the treatment of atherosclerosis and with hormonal agonist or antagonists in the treatment of endocrine disorders, such as thyroid disorders.

It is to be understood that the proteins of the present invention, including but not limited to, SEQ ID NO: 2 and SEQ ID NO: 4, or fragments or conservative substitutions thereof, may be administered together with other compositions such as anti-parasitic compositions, pesticides, herbicides and fertilizers. Accordingly, the proteins of the present invention may be useful alone or in combination with other compositions for treating humans or animals, including livestock, other farm animals and domestic animals, including pets, for preventing or fighting parasitic disease, for protecting plants and crops against attack by parasites, especially soil nematodes, and for destroying parasites.

Accordingly, an object of the present invention is to provide nucleotide sequences, or fragments thereof or conservative substitutions thereof, encoding for the production of proteins, or fragments thereof or conservative substitutions thereof, that are involved in ROI production, stimulate superoxide production or generate peroxidative reactions.

It is another object of the present invention is to provide the proteins represented in SEQ ID NO: 2, SEQ ID NO: 4, SEQ ID NO: 31, and SEQ ID NO: 32 or fragments Or conservative substitutions thereof.

It is another object of the present invention is to provide the nucleotide sequences encoding for the proteins represented in SEQ ID NO: 2, SEQ ID NO: 4, SEQ ID NO: 31, and SEQ ID NO: 32 or fragments or conservative substitutions thereof, wherein these nucleotide sequence include SEQ ID NO: 1, SEQ ID NO: 3 or fragments or conservative substitutions thereof.

It is another object of the present invention to provide proteins, fragments thereof or conservative substitutions thereof, involved in exoskeletal or cuticle formation that may be used as targets for therapies designed to prevent exoskeletal or cuticle formation and to harm organisms having an exoskeleton or cuticle, particularly parasites.

It is another object of the present invention to provide proteins, fragments thereof or conservative substitutions thereof, involved in thyroid hormone biosynthesis that may be used as targets for therapies designed to inhibit biosynthesis of thyroid hormone.

It is yet another object of the present invention to provide proteins, fragments thereof or conservative substitutions thereof, involved in tissue fibrosis that may be used as targets for therapies designed to prevent fibrosis.

Another object of the present invention is to provide proteins involved in lung fibrosis that may be used as targets for therapies designed to prevent lung fibrosis.

Another object of the present invention is to provide vectors containing these nucleotide sequences, or fragments thereof.

Yet another object of the present invention is to provide cells transfected with these vectors.

Still another object of the present invention is to administer cells transfected with these vectors to animals and humans.

Another object of the present invention is to provide proteins, or fragments thereof, that are involved in ROI production, stimulate superoxide production or generate peroxidative reactions.

Still another object of the present invention is to provide antibodies, including monoclonal and polyclonal antibodies, or fragments thereof, raised against proteins, or fragments thereof or conservative substitutions thereof, that are involved in ROI production, stimulate superoxide production or generate peroxidative reactions. Such antibodies are useful in the localization and measurement of proteins, or fragments thereof, that are involved in ROI production.

Another object of the present invention is to administer genes containing nucleotide sequences, or fragments thereof, encoding for the production of proteins, or fragments thereof or conservative substitutions thereof, that are involved in ROI production, stimulate superoxide production or generate peroxidative reactions, to animals and humans and also to cells obtained from animals and humans.

Another object of the present invention is to administer antisense complimentary sequences of genes containing nucleotide sequences, or fragments thereof or conservative substitutions thereof, encoding for the production of proteins, or fragments thereof or conservative substitutions thereof, that are involved in ROI production, stimulate superoxide production or generate peroxidative reactions, to animals and humans and also to cells obtained from animals and humans.

Yet another object of the present invention is to provide a method for stimulating or inhibiting cellular proliferation by administering vectors containing nucleotide sequences, or fragments thereof, encoding for the production of proteins, or fragments thereof, that are involved in ROI production, stimulate superoxide production or generate peroxidative reactions, to animals and humans. It is also an object of the present invention to provide a method for stimulating or inhibiting cellular proliferation by administering vectors containing antisense complimentary sequences of nucleotide sequences, or fragments thereof, encoding for the production of proteins, or fragments thereof, that are involved in ROI production, stimulate superoxide production or generate peroxidative reactions, to animals and humans. These methods of stimulating cellular proliferation are useful for a variety of purposes, including but not limited to, developing animal models of tumor formation, stimulating cellular proliferation of blood marrow cells following chemotherapy or radiation, or in cases of anemia.

Yet another object of the present invention is to provide nucleotide probes useful for the detection, localization and measurement of nucleotide sequences, or fragments thereof, encoding for the production of proteins, or fragments thereof, that are involved in ROI production, stimulate superoxide production or generate peroxidative reactions.

Another object of the present invention is to provide kits useful for detection of nucleic acids including the nucleic acids represented in SEQ ID NO: 1, and SEQ ID NO: 3, or fragments thereof or conservative substitutions thereof, that encode for proteins, or fragments thereof or conservative substitutions thereof, that are involved in ROI production, stimulate superoxide production or generate peroxidative reactions.

Yet another object of the present invention is to provide kits useful for detection and measurement of nucleic acids including the nucleic acids represented in SEQ ID NO: 1, and SEQ ID NO: 3, or fragments thereof, that encode for proteins, or fragments thereof or conservative substitutions thereof, that are involved in ROI production, stimulate superoxide production or generate peroxidative reactions.

Another object of the present invention is to provide kits useful for detection of proteins, including the proteins represented in SEQ ID NO: 2 and SEQ ID NO: 4 or fragments thereof, that are involved in ROI production, stimulate superoxide production or generate peroxidative reactions.

Yet another object of the present invention is to provide kits useful for detection and measurement of proteins, including the proteins represented in SEQ ID NO: 2 and SEQ ID NO: 4, or fragments thereof, that are involved in ROI production, stimulate superoxide production or generate peroxidative reactions.

Still another object of the present invention is to provide kits useful for localization of proteins, including the proteins represented in SEQ ID NO: 2 and SEQ ID NO: 4, or fragments thereof, that are involved in ROI production, stimulate superoxide production or generate peroxidative reactions.

Yet another object of the present invention is to provides kits useful for the detection, measurement or localization of nucleic acids, or fragments thereof, encoding for proteins, or fragments thereof, that are involved in ROI production, for use in diagnosis and prognosis of abnormal cellular proliferation related to ROI production.

Another object of the present invention is to provides kits useful for the detection, measurement or localization of proteins, or fragments thereof, that are involved in ROI production, for use in diagnosis and prognosis of abnormal cellular proliferation related to ROI production.

These and other objects, features and advantages of the present invention will become apparent after a review of the following detailed description of the disclosed embodiments and the appended drawings.

DETAILED DESCRIPTION OF THE INVENTION

Figure 1:
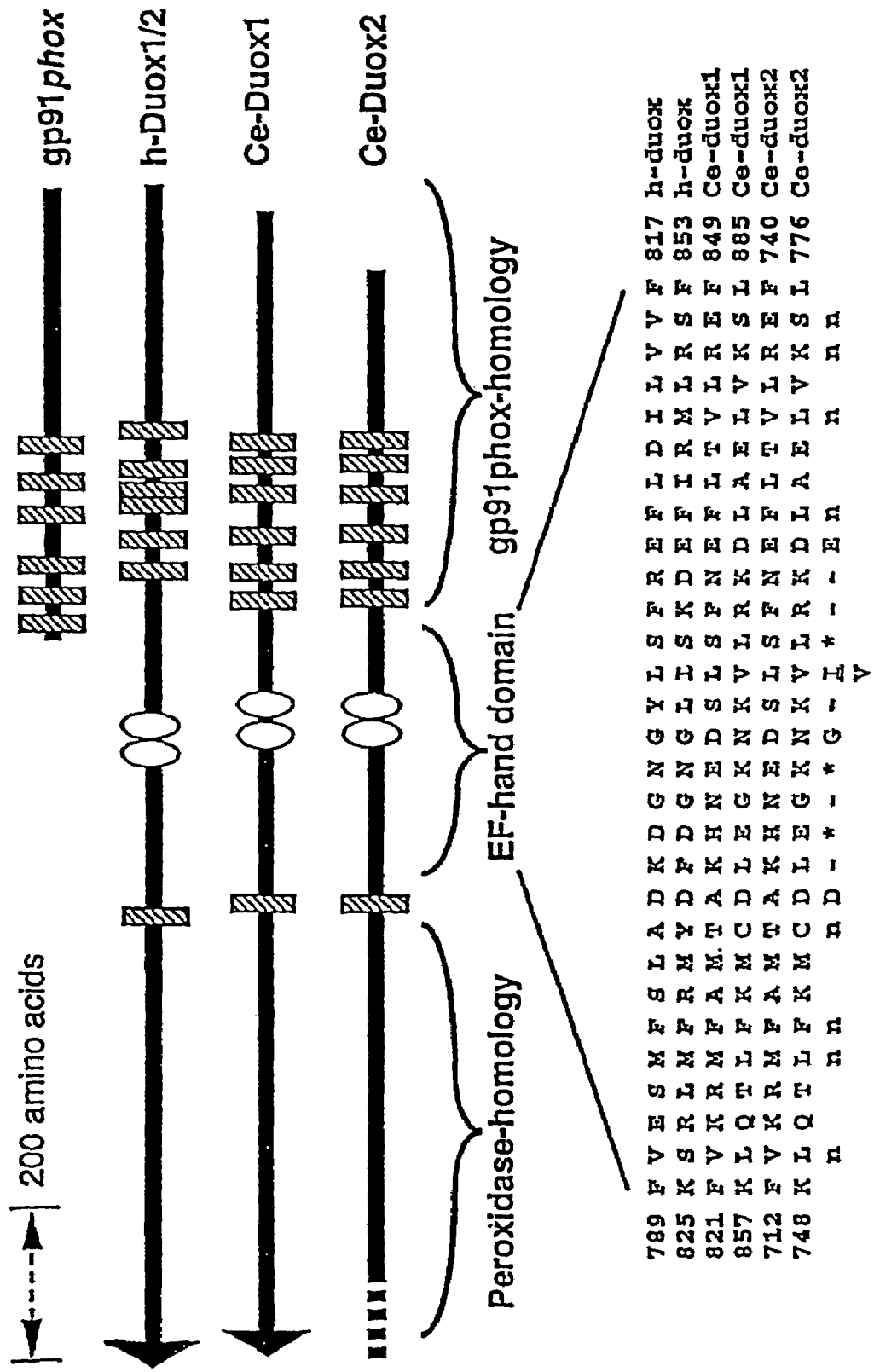
FIG. 1. Structure and sequence alignments of large homologs of gp9phox. Sequence alignment of the first and second EF hand domains from h-doux (SEQ ID NO: 2, residues 823 to 851 and 859 to 887 respectively), the first and second EF hand domains from Ce-doux1, (SEQ ID NO: 3, residues 821 to 849 and 857 to 885 respectively), and the first and second EF hand domains from Ce-doux2 (SEQ ID NO: 3 residues 821 to 849 and 857 to 885 respectively). Domain structure of Duox proteins. Secretory signal peptide sequences are indicated by a gray triangle, while predicted transmembrane alpha helices are indicated by a hashed rectangle. White ovals indicate regions showing homology with EF-hand calcium binding sites.

The present invention solves the problems described above by providing a novel family of nucleotide sequences and proteins, encoded by these nucleotide sequences, termed duox proteins. The term "duox" refers to "dual oxidase". In particular, the present invention provides novel compositions comprising the nucleotide sequences SEQ ID NO: 1, and SEQ ID NO: 3, and fragments thereof or conservative substitutions thereof, which encode, respectively, for the expression of proteins comprising SEQ ID NO: 2 and SEQ ID NO: 4 and fragments thereof or conservative substitutions thereof. Preferred protein fragments include, but are not limited to SEQ ID NO: 31 and SEQ ID NO: 32.

The duox proteins described herein have homology to the gp91phox protein involved in ROI generation, however, the duox proteins comprise a novel and distinct family of proteins. The duox proteins described herein have three distinct regions: the amino terminal region having homology to peroxidase proteins, the internal region having homology to calmodulin (CAM) proteins and the carboxy-terminal region having homology to mox (also called nox) proteins. The amino acid sequence of human duox2 is shown in SEQ ID NO: 2. Nucleotides encoding duox2 proteins are also shown in SEQ ID NO: 1. In addition to the human duox proteins, comparison of the sequence of human duox1 and human duox2 with genomic databases using BLAST searching resulted in the identification of two homologs of duox in C. elegans (Ce-duox1 SEQ ID NO: 3) and the pseudogene Ce-duox2. Drosophila also appears to have at least one duox homolog. Thus, the duox family of genes/proteins is widely distributed among multicellular organisms.

High molecular weight homologs of gp91phox, have been identified in human (h) and C. elegans (Ce), and are termed Duox for "dual oxidase" because they have both a peroxidase-homology domain and a gp91phox domain. Ce-Duox uses cytosolic NADPH to generate reactive oxygen. It catalyzes cross-linking of free tyrosine ethyl ester involved in the stabilization of the cuticular extracellular matrix in nematodes.

Although not wanting to be bound by the following statement, it is believed that duox enzymes, for example duox2 and Ce-duox1, have dual enzymatic functions, catalyzing both the generation of superoxide and peroxidative type reactions. The latter class of reactions utilize hydrogen peroxide as a substrate (and in some cases have been proposed to utilize superoxide as a substrate). Since hydrogen peroxide is generated spontaneously from the dismutation of superoxide, it is believed that the NAD(P)H oxidase domain generates the superoxide and/or hydrogen peroxide which can then be used as a substrate for the peroxidase domain. In support of this hypothesis, a model for the duox2 protein in C. elegans has been developed that has an extracellular N-terminal peroxidase domain, a transmembrane region and a NADPH binding site located on the cytosolic face of the plasma membrane. By analogy with the neutrophil NADPH-oxidase which generates extracellular superoxide, human duox2 is predicted to generate superoxide and its byproduct hydrogen peroxide extracellularly where it can be utilized by the peroxidase domain.

The peroxidase domain is likely to confer additional biological functions. Depending upon the co-substrate, peroxidases can participate in a variety of reactions including halogenation such as the generation of hypochlorous acid (HOCl) by myeloperoxidase and the iodination of tyrosine to form thyroxin by thyroid peroxidase. Peroxidases have also been documented to participate in the metabolism of polyunsaturated fatty acids, and in the chemical modification of tyrosine in collagen (by sea urchin ovoperoxidase). Although not wanting to be bound by this statement, it is believed that the predicted transmembrane nature of duox2 facilitates its function in the formation or modification of extracellular matrix or basement membrane. Since the extracellular matrix plays an important role in tumor cell growth, invasion and metastasis, it is believed that the duox type enzymes play a pathogenic role in such conditions.

In addition to the nucleotide sequences described above, the present invention also provides vectors containing these nucleotide sequences and fragments thereof or conservative substitutions thereof, cells transfected with these vectors which produce the proteins comprising SEQ ID NO: 2 and SEQ ID NO: 4 and fragments thereof or conservative substitutions thereof, and antibodies to these proteins and fragments thereof. The present invention also provides methods for stimulating cellular proliferation by administering vectors, or cells containing vectors, encoded for production of the proteins comprising SEQ ID NO: 2, SEQ ID NO: 4, and fragments thereof. The nucleotides and antibodies of the present invention are useful for the detection, localization and measurement of the nucleic acids encoding for the production of the proteins of the present invention, and also for the detection, localization and measurement of the proteins of the present invention. These nucleotides and antibodies can be combined with other reagents in kits for the purposes of detection, localization and measurement. These kits are useful for diagnosis and prognosis of conditions involving cellular proliferation associated with production of reactive oxygen intermediates.

The present invention solves the problems described above by providing a composition comprising the nucleotide sequence SEQ ID NO: 1 and fragments thereof and conservative substitutions thereof. The present invention also provides a composition comprising the nucleotide sequence SEQ ID NO: 3 and fragments thereof and conservative substitutions thereof. The present invention provides a composition comprising the protein SEQ ID NO: 2, and fragments and conservative substitutions thereof, encoded by the nucleotide sequence SEQ ID NO: 1 and fragments and conservative substitutions thereof The present invention provides a composition comprising the protein SEQ ID NO: 4 and fragments and conservative substitutions thereof, encoded by the nucleotide sequence SEQ ID NO: 3 and fragments and conservative substitutions thereof. Preferred protein fragments include, but are not limited to, SEQ ID NO: 31 and SEQ ID NO: 32.

The present invention also provides vectors containing the nucleotide sequences SEQ ID NO: 1, and SEQ ID NO: 3 or fragments thereof The present invention also provides cells transfected with these vectors.

In addition, the present invention provides cells stably transfected with the nucleotide sequence SEQ ID NO: 1 or fragments thereof. The present invention also provides cells stably transfected with the nucleotide sequence SEQ ID NO: 3 or fragments thereof.

The present invention provides cells stably transfected with the nucleotide sequence SEQ ID NO: 1 or fragments or conservative substitutions thereof, which produce the protein SEQ ID NO: 2 or fragments or conservative substitutions thereof. In addition, the present invention provides cells stably transfected with the nucleotide sequence SEQ ID NO: 3 or fragments or conservative substitutions thereof which produce the protein SEQ ID NO: 4 or fragments or conservative substitutions thereof.

The present invention provides a method for stimulating growth by administering cells stably transfected with the nucleotide sequence SEQ ID NO: 1 or fragments or conservative substitutions thereof which produce the protein SEQ ID NO: 2 or fragments or conservative substitutions thereof. The present invention also provides a method for stimulating growth by administering cells stably transfected with the nucleotide sequence SEQ ID NO: 3 or fragments or conservative substitutions thereof, which produce the protein SEQ ID NO: 4 or fragments or conservative substitutions thereof.

Specifically, the present invention provides a method for stimulating tumor formation by administering cells stably transfected with the nucleotide sequence SEQ ID NO: 1 or fragments thereof, which produce the protein SEQ ID NO: 2 or fragments thereof. The present invention also provides a method for stimulating tumor formation by administering cells stably transfected with the nucleotide sequence SEQ ID NO: 3 or fragments thereof, which produce the protein SEQ ID NO: 4 or fragments thereof. The present invention may also be used to develop anti-sense nucleotide sequences to SEQ ID NO: 1 and SEQ ID NO: 3, or fragments thereof. These anti-sense molecules may be used to interfere with translation of nucleotide sequences, such as SEQ ID NO: 1, and SEQ ID NO: 3, or fragments thereof, that encode for proteins such as SEQ ID NO: 2, SEQ ID NO: 4, or fragments thereof. Administration of these anti-sense molecules, or vectors encoding for anti sense molecules, to humans and animals, would interfere with production of proteins such as SEQ ID NO: 2, SEQ ID NO: 4, or fragments thereof, thereby decreasing production of ROIs and inhibiting cellular proliferation. These methods are useful in producing animal models for use in study of tumor development, cuticle formation and vascular growth, and for study of the efficacy of treatments for affecting tumor growth, vascular growth and cuticle formation in vivo.

The present invention also provides a method for high throughput screening of drugs and chemicals which modulate the proliferative activity of the enzymes of the present invention or fragments or conservative substitutions thereof, thereby affecting cell division, metabolic activity, cuticle formation, fibrosis and other biological functions involving oxidative reactions. Combinatorial chemical libraries may be screened for chemicals which modulate the proliferative activity or oxidative activity of these enzymes. Drugs and chemicals may be evaluated based on their ability to modulate the enzymatic activity of the expressed or endogenous proteins, including those represented SEQ ID NO: 2 and SEQ ID NO: 4 or fragments or conservative substitutions thereof. Endogenous proteins may be obtained from many different tissues or cells, such as colon cells. Drugs may also be evaluated based on their ability to bind to the expressed or endogenous proteins represented by SEQ ID NO: 2 and SEQ ID NO: 4 or fragments or conservative substitutions thereof Enzymatic activity may be NADPH- or NADH-dependent superoxide generation catalyzed by the holoprotein. Enzymatic activity may also be NADPH- or NADH-dependent diaphorase activity catalyzed by either the holoprotein or the flavoprotein domain.

By flavoprotein domain, is meant approximately the C-terminal half of the enzymes shown in SEQ ID NO: 2 and SEQ ID NO: 4, or fragments or conservative substitutions thereof, (approximately the C-terminal 265 amino acids). This fragment of gp91phox has NADPH-dependent reductase activity towards cytochrome c, nitrobluetetrazolium and other dyes. Expressed proteins or fragments thereof can be used for robotic screens of existing combinatorial chemical libraries. While not wanting to be bound by the following statement, it is believed that the NADPH or NADH binding site and the FAD binding site are useful for evaluating the ability of drugs and other compositions to bind to the duox enzymes or fragments or conservative substitutions thereof, or to modulate their enzymatic activity. The use of the holoprotein or the C-terminal half or end regions are preferred for developing a high throughput drug screen. Additionally, the N-terminal one-third of the duox domain (the peroxidase domain) may also be used to evaluate the ability of drugs and other compositions to inhibit the peroxidase activity, and for further development of a high throughput drug screen.

The present invention also provides antibodies directed to the oxidative enzymes such as SEQ ID NO: 2 and SEQ ID NO: 4 and fragments or conservative substitutions thereof. Preferred protein fragments include, but are not limited to, SEQ ID NO: 31 and SEQ ID NO: 32. The antibodies of the present invention are useful for a variety of purposes including localization, detection and measurement of the proteins SEQ ID NO: 2 and SEQ ID NO: 4 and fragments or conservative substitutions thereof. The antibodies may be employed in kits to accomplish these purposes. These antibodies may also be linked to cytotoxic agents for selected killing of cells. The term antibody is meant to include any class of antibody such as IgG, IgM and other classes. The term antibody also includes a completely intact antibody and also fragments thereof, including but not limited to Fab fragments and Fab+Fc fragments.

The present invention also provides the nucleotide sequences SEQ ID NO: 1 and SEQ ID NO:. 3 and fragments or conservative substitutions thereof. These nucleotides are useful for a variety of purposes including localization, detection, and measurement of messenger RNA involved in synthesis of the proteins represented as SEQ ID NO: 2 and SEQ ID NO: 4 and fragments or conservative substitutions thereof. These nucleotides may also be used in the construction of labeled probes for the localization, detection, and measurement of nucleic acids such as messenger RNA or alternatively for the isolation of larger nucleotide sequences containing the nucleotide sequences shown in SEQ ID NO: 1, and SEQ ID NO: 3 or fragments or conservative substitutions thereof. These nucleotide sequences may be used to isolate homologous strands from other species using techniques known to one of ordinary skill in the art. These nucleotide sequences may also be used to make probes and complementary strands.

Most particularly, the present invention involves a method for modulation of growth by modifying the proteins represented as SEQ ID NO: 2 and SEQ ID NO: 4 or fragments or conservative substitutions thereof.

The term "mitogenic regulators" is used herein to mean any molecule that acts to affect cell division.

The term "animal" is used herein to mean humans and nonhuman animals of both sexes.

The terms "a", "an" and "the" as used herein are defined to mean one or more and include the plural unless the context is inappropriate.

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above; individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

When the peptides are relatively short in length (i.e., less than about 50 amino acids), they are often synthesized using standard chemical peptide synthesis techniques. Solid phase synthesis in which the C-terminal amino acid of the sequence is attached to an insoluble support followed by sequential addition of the remaining amino acids in the sequence is a preferred method for the chemical synthesis of the antigenic epitopes described herein. Techniques for solid phase synthesis are known to those skilled in the art.

Alternatively, the antigenic epitopes described herein are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

One of skill in the art will recognize that after chemical synthesis, biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

The genetic constructs of the present invention include coding sequences for different proteins, fragments thereof, and peptides. The genetic constructs also include epitopes or domains chosen to permit purification or detection of the expressed protein, Such epitopes or domains include DNA sequences encoding the glutathione binding domain from glutathione S-transferase, hexa-histidine, thioredoxin, hemagglutinin antigen, maltose binding protein, and others commonly known to one of skill in the art. The preferred genetic construct includes the nucleotide sequences of SEQ ID NO: 1 and SEQ ID NO: 3 or fragments or conservative substitutions thereof. It is to be understood that additional or alternative nucleotide sequences may be included in the genetic constructs in order to encode for the following: a) multiple copies of the desired proteins, fragments thereof, or peptides; b) various combinations of the desired proteins, fragments thereof, or peptides; and c) conservative modifications of the desired proteins, fragments thereof, or peptides, and combinations thereof. Still another preferred protein of the present invention is human duox2 (SEQ ID NO: 2) protein, and fragments or conservative substitutions thereof, as encoded by SEQ ID NO: 1 and fragments or conservative substitutions thereof. Another preferred protein of the present invention is Ce Duox 1 (SEQ ID NO:4) protein and fragments or conservative substitutions thereof, as encoded by SEQ ID NO: 3 and fragments or conservative substitutions thereof. The nucleotide sequences of the present invention may also be employed to hybridize to nucleic acids such as DNA or RNA nucleotide sequences under high stringency conditions which permit detection, for example, of alternately spliced messages.

The genetic construct is expressed in an expression system such as in NIH 3T3 cells using recombinant sequences in a pcDNA-3 vector (Invitrogen, Carlsbad, Calif.) to produce a recombinant protein. Preferred expression systems include but are not limited to Cos-7 cells, insect cells using recombinant baculovirus, and yeast. It is to be understood that other expression systems known to one of skill in the art may be used for expression of the genetic constructs of the present invention. A preferred protein of the present invention is referred to herein as human duox2, or fragments or conservative substitutions thereof, which has the amino acid sequence set forth in SEQ ID NO:2, or an amino acid sequence having amino acid substitutions as defined in the definitions that do not significantly alter the function of the recombinant protein in an adverse manner. Another preferred protein of the present invention is Ce Duox 1 (SEQ ID NO: 4) or fragments or conservative substitutions thereof, as encoded by SEQ ID NO: 3 and fragments or conservative substitutions thereof.

Terminology

As described herein, the term "human duox2" refers to a protein comprising an amino acid sequence as set forth in SEQ ID NO:2, or a fragment or conservative substitution thereof, and encoded by the nucleotide sequence as set forth in SEQ ID NO:1, or a fragment or conservative substitution thereof Ce duox refers to duox from *C. elegans* or a fragment or conservative substitution thereof.

Construction of the Recombinant Gene

The desired gene is ligated into a transfer vector, such as pcDNA3, and the recombinants are used to transform host cells such as Cos-7 cells. It is to be understood that different transfer vectors, host cells, and transfection methods may be employed as commonly known to one of ordinary skill in the art. Two desired genes for use in transfection are shown in SEQ ID NO: 1, and SEQ ID NO: 3. For example, lipofectamine-mediated transfection and in vivo homologous recombination is used to introduce the duox1 gene into NIH 3T3 cells.

The synthetic gene is cloned and the recombinant construct containing duox gene is produced and grown in confluent monolayer cultures of a Cos-7 cell line. The expressed recombinant protein is then purified, preferably using affinity chromatography techniques, and its purity and specificity determined by known methods.

A variety of expression systems may be employed for expression of the recombinant protein. Such expression methods include, but are not limited to the following: bacterial expression systems, including those utilizing *E. coli* and *Bacillus subtilis;* virus systems; yeast expression systems; cultured insect and mammalian cells; and other expression systems known to one of ordinary skill in the art.

Transfection of Cells

It is to be understood that the vectors of the present invention may be transfected into any desired cell or cell line. Both in vivo and in vitro transfection of cells are contemplated as part of the present invention. Preferred cells for transfection include but are not limited to the following: fibroblasts (possibly to enhance wound healing and skin formation), granulocytes (possible benefit to increase function in a compromised immune system as seen in AIDS, and aplastic anemia), muscle cells, neuroblasts, stem cells, bone marrow cells, osteoblasts, B lymphocytes, and T lymphocytes.

Cells may be transfected with a variety of methods known to one of ordinary skill in the art and include but are not limited to the following: electroporation, gene gun, calcium phosphate, lipofectamine, and fugene, as well as adenoviral transfection systems.

Host cells transfected with the nucleic acids represented in SEQ ID NO: 1, and SEQ ID NO: 3, or fragments or conservative substitutions thereof, are used to express the proteins SEQ ID NO: 2 and SEQ ID NO: 4, respectively, or fragments or conservative substitutions thereof.

These expressed proteins are used to raise antibodies. These antibodies may be used for a variety of applications including but not limited to immunotherapy against cancers expressing one of the duox proteins, for affecting cuticle formation, and for detection, localization and measurement of the proteins shown in SEQ ID NO: 2 and SEQ ID NO: 4, or fragments or conservative substitutions thereof.

Purification and Characterization of the Expressed Protein

The proteins of the present invention can be expressed as a fusion protein with a poly histidine component, such as a hexa histidine, and purified by binding to a metal affinity column using nickel or cobalt affinity matrices. The protein can also be expressed as a fusion protein with glutathione S-transferase and purified by affinity chromatography using a glutathione agarose matrix. The protein can also be purified by immunoaffinity chromatography by expressing it as a fusion protein, for example with hemagglutinin antigen. The expressed or naturally occurring protein can also be purified by conventional chromatographic and purification methods which include anion and cation exchange chromatography, gel exclusion chromatography, hydroxylapatite chromatography, dye binding chromatography, ammonium sulfate precipitation, precipitation in organic solvents or other techniques commonly known to one of skill in the art.

Methods of Assessing Activity of Expressed Proteins

Different methods are available for assessing the activity of the expressed proteins of the present invention, including, but not limited to, the proteins represented as SEQ ID NO: 2 and SEQ ID NO: 4, substituted analogs thereof, and fragments or conservative substitutions thereof.

1. Assays of the Holoprotein and Fragments thereof for Superoxide Generation:

A. General Considerations.

These assays are useful in assessing efficacy of drugs designed to modulate the activity of the enzymes of the present invention. The holoprotein may be expressed in COS-7 cells, NIH 3T3 cells, insect cells (using baculoviral technology) or other cells using methods known to one of skill in the art. Membrane fractions or purified protein are used for the assay. The assay may require or be augmented by other cellular proteins such as p47phox, p67phox, and Rac1, as well as potentially other unidentified factors (e.g., kinases or other regulatory proteins).

B. Cytochrome C Reduction.

NADPH or NADH is used as the reducing substrate, in a concentration of about 100 μM. Reduction of cytochrome c is monitored spectrophotometrically by the increase in absorbance at 550 nm, assuming an extinction coefficient of 21 mM$^{-1}$ cm$^{-1}$. The assay is performed in the absence and presence of about 10 μg superoxide dismutase. The superoxide-dependent reduction is defined as cytochrome c reduction in the absence of superoxide dismutase minus that in the presence of superoxide dismutase (Uhlinger et al. (1991) *J. Biol. Chem.* 266, 20990–20997). Acetylated cytochrome c may also be used, since the reduction of acetylated cytochrome c is thought to be exclusively via superoxide.

C. Nitroblue Tetrazolium Reduction.

For nitroblue tetrazolium (NBT) reduction, the same general protocol is used, except that NBT is used in place of cytochrome c. In general, about 1 mL of filtered 0.25% nitrotetrazolium blue (Sigma, St. Louis, Mo.) is added in Hanks buffer without or with about 600 Units of superoxide dismutase (Sigma) and samples are incubated at approximately 37° C. The oxidized NBT is clear, while the reduced NBT is blue and insoluble. The insoluble product is collected by centrifugation, and the pellet is re-suspended in about 1 mL of pyridine (Sigma) and heated for about 10 minutes at 100° C. to solubilize the reduced NBT. The concentration of reduced NBT is determined by measuring the absorbance at 510 nm, using an extinction coefficient of 11,000 M$^{-1}$ cm$^{-1}$. Untreated wells are used to determine cell number.

D. Luminescence.

Superoxide generation may also be monitored with a chemiluminescence detection system utilizing lucigenin (bis-N-methylpyridinium nitrate, Sigma, St. Louis, Mo.). The sample is mixed with about 100 μM NADPH (Sigma, St. Louis, Mo.) and 10 μM lucigenin (Sigma, St. Louis, Mo.) in a volume of about 150 μL Hanks solution. Luminescence is monitored in a 96-well plate using a LumiCounter (Packard, Downers Grove, Ill.) for 0.5 second per reading at approximately 1 minute intervals for a total of about 5 minutes; the highest stable value in each data set is used for comparisons. As above, superoxide dismutase is added to some samples to prove that the luminescence arises from superoxide. A buffer blank is subtracted from each reading (Ushio-Fukai et al. (1996) *J. Biol. Chem.* 271, 23317–23321).

E. Assays in Intact Cells.

Assays for superoxide generation may be performed using intact cells, for example, the duox-transfected NIH 3T3 cells. In principle, any of the above assays can be used to evaluate superoxide generation using intact cells, for example, the duox-transfected NIH 3T3 cells. NBT reduction is a preferred assay method.

2. Assays of Truncated Proteins Comprised of Approximately the C-Terminal 265 Amino Acid Residues While not wanting to be bound by the following statement, the truncated protein comprised of approximately the C-terminal 265 amino acid residues is not expected to generate superoxide, and therefore, superoxide dismutase is not added in assays of the truncated protein. Basically, a similar assay is established and the superoxide-independent reduction of NBT, cytochrome c, dichlorophenolindophenol, ferricyanide, or another redox-active dye is examined.

Nucleotides and Nucleic Acid Probes

The nucleotide sequences SEQ ID NO: 1 and SEQ ID NO: 3, as well as fragments or conservative substitutions thereof, and PCR primers therefor, may be used, respectively, for localization, detection and measurement of nucleic acids related to SEQ ID NO: 1 and SEQ ID NO: 3, as well as fragments or conservative substitutions thereof SEQ ID NO 1 is also known as a nucleotide sequence encoding human duox2 in this application. SEQ ID NO: 3 is also known as a nucleotide sequence encoding Ce duox 1 in this application.

The nucleotide sequences SEQ ID NO: 1, SEQ ID NO: 3, as well as fragments or conservative substitutions thereof, may be used to create probes to isolate larger nucleotide sequences containing the nucleotide sequences SEQ ID NO: 1, SEQ ID NO: 3, respectively. The nucleotide sequences SEQ ID NO: 1, SEQ ID NO: 3, as well as fragments or conservative substitutions thereof, may also be used to create probes to identify and isolate duox proteins in other species.

The nucleic acids described herein include messenger RNA coding for production of SEQ ID NO: 2, SEQ ID NO: 4, and fragments thereof. Such nucleic acids include but are not limited to cDNA probes. These probes may be labeled in a variety of ways known to one of ordinary skill in the art. Such methods include but are not limited to isotopic and non-isotopic labeling. These probes may be used for in situ hybridization for localization of nucleic acids such as mRNA encoding for SEQ ID NO: 2, and SEQ ID NO: 4, and fragments or conservative substitutions thereof. Localization may be performed using is situ hybridization at both ultrastructural and light microscopic levels of resolution using techniques known to one of ordinary skill in the art.

These probes may also be employed to detect and quantitate nucleic acids and mRNA levels using techniques known to one of ordinary skill in the art including but not limited to solution hybridization.

Antibody Production

The proteins shown in SEQ ID NO: 2, SEQ ID NO: 4 SEQ ID NO: 31 and SEQ ID NO: 32, or fragments or conservative substitutions thereof, are combined with a pharmaceutically acceptable carrier or vehicle to produce a pharmaceutical composition and administered to animals for the production of polyclonal antibodies using methods known to one of ordinary skill in the art. The preferred animals for antibody production are rabbits and mice. Other animals may be employed for immunization with these proteins or fragments thereof. Such animals include, but are not limited to the following; sheep, horses, pigs, donkeys, cows, monkeys and rodents such as guinea pigs and rats.

The terms "pharmaceutically acceptable carrier or pharmaceutically acceptable vehicle" are used herein to mean any liquid including but not limited to water or saline, oil, gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The pharmaceutical compositions may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The pharmaceutical composition may be administered through different routes, such as oral, including buccal and sublingual, rectal, parenteral, aerosol, nasal, intramuscular, subcutaneous, intradermal, and topical. The pharmaceutical composition of the present invention may be administered in different forms, including but not limited to solutions, emulsions and suspensions, microspheres, particles, microparticles, nanoparticles, and liposomes. It is expected that from about 1 to 7 dosages may be required per immunization regimen. Initial injections may range from about 0.1 µg to 1 mg, with a preferred range of about 1 µg to 800 µg, and a more preferred range of from approximately 25 µg to 500 µg. Booster injections may range from 0.1 µg to 1 mg, with a preferred range of approximately 1 µg to 800 µg, and a more preferred range of about 10 µg to 500 µg.

The volume of administration will vary depending on the route of administration and the size of the recipient. For example, intramuscular injections may range from about 0.1 ml to 1.0 ml.

The pharmaceutical composition may be stored at temperatures of from about 4° C. to −100° C. The pharmaceutical composition may also be stored in a lyophilized state at different temperatures including room temperature. The pharmaceutical composition may be sterilized through conventional means known to one of ordinary skill in the art. Such means include, but are not limited to filtration, radiation and heat. The pharmaceutical composition of the present invention may also be combined with bacteriostatic agents, such as thimerosal, to inhibit bacterial growth.

Adjuvants

A variety of adjuvants known to one of ordinary skill in the art may be administered in conjunction with the protein in the pharmaceutical composition. Such adjuvants include, but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins: membrane lipids; or combinations thereof.

Monoclonal antibodies can be produced using hybridoma technology in accordance with methods well known to those skilled in the art. The antibodies are useful as research or diagnostic reagents or can be used for passive immunization. The composition may optionally contain an adjuvant.

The polyclonal and monoclonal antibodies useful as research or diagnostic reagents may be employed for detection and measurement of SEQ ID NO: 2, SEQ ID NO: 4, SEQ ID NO: 31 and SEQ ID NO: 32, and fragments or conservative substitutions thereof. Such antibodies may be used to detect these proteins in a biological sample, including but not limited to samples such as cells, cellular extracts, tissues, tissue extracts, biopsies, tumors, and biological fluids. Such detection capability is useful for detection of disease related to these proteins to facilitate diagnosis and prognosis and to suggest possible treatment alternatives.

Detection may be achieved through the use of immunocytochemistry, ELISA, radioimmunoassay or other assays as commonly known to one of ordinary skill in the art. The duox proteins, including the hduox2 and Ce-duox proteins of the present invention, or fragments or conservative substitutions thereof, may be labeled through commonly known approaches, including but not limited to the following: radiolabeling, dyes, magnetic particles, biotin-avidin, fluorescent molecules, chemiluminescent molecules and systems, ferritin, colloidal gold, and other methods known to one of skill in the art of labeling proteins.

Administration of Antibodies

The antibodies directed to the proteins shown as SEQ ID NO: 2, SEQ ID NO: 4, SEQ ID NO: 31, SEQ ID NO: 32, or directed to fragments or conservative substitutions thereof, may also be administered directly to humans and animals in a passive immunization paradigm. Antibodies directed to extracellular portions of SEQ ID NO: 2, and SEQ ID NO: 4, bind to these extracellular epitopes. Attachment of labels to these antibodies facilitates localization and visualization of sites of binding. Attachment of molecules such as ricin or other cytotoxins to these antibodies helps to selectively damage or kill cells expressing SEQ ID NO: 2, and SEQ ID NO: 4, or fragments thereof.

Kits

The present invention includes kits useful with the antibodies, nucleic acids, nucleic acid probes, labeled antibodies, labeled proteins or fragments thereof for detection, localization and measurement of SEQ ID NO: 1, SEQ ID NO: 2, SEQ ID NO: 3, SEQ ID NO: 4, or combinations and fragments or conservative substitutions thereof.

Kits may be used for immunocytochemistry, in situ hybridization, solution hybridization, radioimmunoassay, ELISA, Western blots, quantitative PCR, and other assays for the detection, localization and measurement of these nucleic acids, proteins or fragments thereof using techniques known to one of skill in the art.

The nucleotide sequences shown in SEQ ID NO: 1, and SEQ ID NO: 3, or fragments thereof, may also be used under high stringency conditions to detect alternately spliced messages related to SEQ ID NO: 1, and SEQ ID NO: 3, or fragments thereof, respectively.

The diagnostic kits may measure or detect the relative expression of the duox proteins described herein (i.e. human duox1 and/or human duox2 and ce-duox).

Fragments of SEQ ID NO: 1, and SEQ ID NO: 3, containing the relevant hybridizing sequence can be synthesized onto the surface of a chip array. RNA samples, e.g., from tumors, are then fluorescently tagged and hybridized onto the chip for detection. This approach may be used diagnostically to characterize tumor types and to tailor treatments and/or provide prognostic information. Such prognostic information may have predictive value concerning disease progression and life span, and may also affect choice of therapy.

The present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Cloning of cDNA for Human Duox 2

A 535-base portion of an expressed sequence tag (EST zc92h03.r1; Genbank accession no. W52750) from human pancreatic islet was identified using the amino-acid sequence of human gp91phox as a query in a Blast search. The bacterial strain #595758 containing the EST sequence zc92h03.r1 in the pBluescript SK-vector was purchased from ATCC (Rockville, Md.). The DNA was sequenced using primers to T7 and T3 vector promoters as well as sequence-specific internal primers. The EST encoded a 440 amino acid partial cDNA exhibiting 24.4% identity to gp91phox, including a stop codon corresponding to the C-terminus of gp91phox. 5'- and 3'-RACE were carried out using human adult pancreas mRNA (Clontech, Palo Alto, Calif.) with the 5' RACE kit for Rapid Amplification of cDNA Ends version 2.0 (Gibco BRL, Gaithersburg, Md.). PCR was done with specific primers: 5'-RACE: Primer 1, 5'-GAAGTGGTGGGAGGCGAAGACATA-3' (SEQ ID NO:5); Primer 2, 5'-CCTGTCATACCTGGGACG-GTCTGG-3' (SEQ ID NO:6); Primer 3, 5'-GAGCACAGT-GAGATGCCTGTTCAG-3' (SEQ ID NO:7); Primer 4, 5'-GGAAGGCAGCAGAGAGCAATGATG-3' (SEQ ID NO:8); Primer 5, 5'-AGGTGGGATGCGGATGTTGAG-3' (SEQ ID NO:9) (for nested PCR); 3'-RACE Primer 6, 5'-ACATCTGCGAGCGGCACTTCCAGA-3' (SEQ ID NO:10); Primer 7, 5'-AGCTCGTCAACAGGCAGGAC-CGAGC-3' (SEQ ID NO:11); Primer 8, 5'-TCTCCATCA-GAATCCACCTTAGGC-3' (SEQ ID NO:12) (for nested PCR). To complete the sequence, 5'-RACE was carried out using human thyroid Marathon-ready cDNA (Clontech, Palo Alto, Calif.) with primer 3 and adapter primer AP1, and primer 5 and adapter primer AP2. These procedures resulted in an additional 3.7 kb 5' region and a 1.5 kb 3' region.

The cDNA for h-Duox2 showed a 4647 base pair open reading frame (Genebank #AF267981) that is predicted to encode a protein of 1548 amino acids (175 kDa), and contained a consensus Kozak sequence, GGC<u>ATG</u>C (SEQ ID NO: 13), at the translation start codon. The Duox2 cDNA sequence is a larger form of a gp91phox homolog previously identified as an NADPH-oxidase in thyroid and termed p138$^{Tox}$; the latter sequence did not contain the a peroxidase homology domain (Dupuy et al., 1999). h-Duox1 and h-Duox2 were 77% identical at the amino acid level.

EXAMPLE 2

Identification of Genes for Ce-Duox1 and Ce-Duox2, Cloning of the cDNA for Ce-Duox1

A BLAST search using the cDNA sequence of human gp91phox identified two putative homologues (Genbank #s AF043697 and AF003130) in the genomic sequence of *C. elegans,* both near the end of chromosome I and separated by ~6 Kb. Based on the gene sequence, PCR primers were designed to amplify two overlapping portions of the Ce-Duox1 gene, one extending from the 5' end and one extending from the 3' end. Primers were 5'-ATTCGTCGACAAAT-GCGCTCAAAACATGTGCTGT-3' (SEQ ID NO: 14) and 5'-AACTTTGTGGATCAAAGTTAGCG-3' (SEQ ID NO: 15) for the 5' region, and 5'-TTGGATTAGCATTTTGC-TATGGAA-3' (SEQ ID NO: 16) 5'-GAGCGGCCGC-GAACGTTTCAAAGCGATGTGCA-3' (SEQ ID NO: 17) for the 3' region. PCR was carried out using a random primed *C. elegans* cDNA library in 1ACT (obtained from R. Barstead, Oklahoma Medical Research Foundation) under the following conditions: denaturation at 95° C. for 30 seconds; annealing at 59° C. for 30 seconds; extension at 72° C. for 1 minute. The 5' piece and the 3' piece were digested with Dra III and ligated to produce the full length Ce-Duox1 cDNA. The full length Ce-Duox1 cDNA was inserted into the pBluescript SK-vector and was sequenced using T7 and T3 vector primers and sequence specific primers.

Figure 2A:
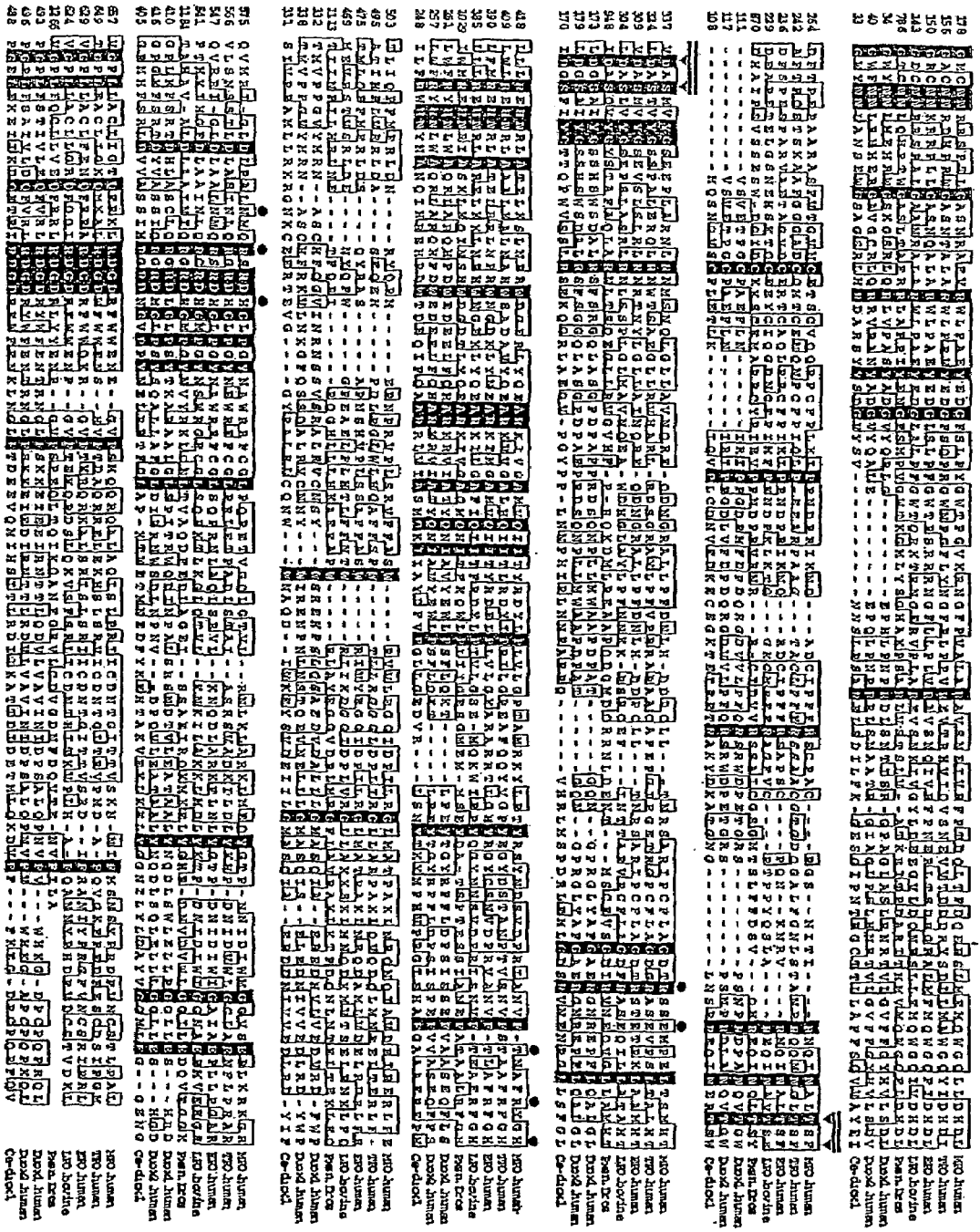
FIG. 2. Comparison of the peroxidase domains of h-Duox, Ce-Duox1 and some known peroxidases. A) Sequence alignments of human MPO (SEQ ID NO: 33), human TPO (SEQ ID NO: 34), human EPO (SEQ ID NO: 35), bovine LPO (residues 61 to 620 of SEQ ID NO: 36). Drosophila Pxsn-dors (SEQ ID NO: 37), human Doux1 (SEQ ID NO: 38), human Doux2 (residues 40–574 of SEQ ID NO: 31) and C. elegans Ce-Doux1 (residues 33–566 of SEQ ID NO: 32). Abbreviations are: MPO, myeloperoxidase; TPO, thyroid peroxidase; EPO, eosinophil peroxidase; LPO, lactoperoxidase, Pxsn.dros, Drosophila peroxidasin. Residues which are conserved among all 7 proteins are shown with black boxes, while those matching a derived consensus sequence are shown in line boxes. Filled circles indicate residues which are proposed to provide contacts with the heme, based on the crystal structure of canine myeloperoxidase (Zeng and Feima, 1992). The superscripted double bar indicates residues comprising a calcium binding region, and filled triangles indicate residues which appear in the crystal structure to bind directly to the calcium ion.

Duox Homologs in C. elegans A BLAST search of the C. elegans genomic database using as a query the protein sequence of gp91phox identified two homologous genes contained in cosmids F56C11 and F53G12. The Ce-Duox1 conceptual transcript (Genebank #AF043697) is predicted to be 8197 bp before splicing, to contain 19 exons, and to encode a protein of 1506 amino acids. Cloning of the cDNA for Ce-Duox1 (Genebank #AF229855) revealed a cDNA of 4491 bp (1497 amino acids), which differed somewhat from the conceptual cDNA obtained from the gene structure due to inaccuracies in the predicted intron-exon junctions. The second transcript, Ce-Duox2 (Genebank #AF043697), is predicted to be 5308 bp before splicing, to contain 16 exons, and to encode a 1313 amino acid protein. Alignment by homology of the genomic sequences of Ce-Duox1 and Ce-Duox2 identified two new exons 5' of the first predicted exon of Duox2 that were highly homologous to the second and third exons of Duox1, but an exon of Duox2 homologous to exon1 of Duox1 could not be identified by homology. The predicted amino acid sequences of both Ce-Duox1 and Ce-Duox2 show approximately 30% identity with h-Duox1 and h-Duox2 (FIGS. 1 and 2A). Ce-Duox1 also contains the same domains as h-Duox1/2 (see below) and is roughly the same size. However, Ce-Duox2 contains a stop codon which should eliminate the extreme C-terminal portion of the protein, which includes a segment of the pyridine nucleotide binding site. Thus, while Ce-Duox2 should contain intact peroxidase and calmodulin-like domains, it is not predicted to encode a functioning NADPH-oxidase domain (see FIG. 1). Except for this C-terminal region, Ce-Duox2 is 94% identical to Ce-Duox1 at the amino acid level. Both Ce-Duox1 and Ce-Duox2 are located near the end of chromosome I, separated by only 6 kb and in opposite orientations. The high degree of sequence identity and retention of intron structure (data not shown), as well as the location of both near the end of a chromosome are consistent with a recent gene duplication.

EXAMPLE 3

Analysis of Primary Structure; Domain Organization and Sequence Comparisons among gp91phox, h-Duox2, Ce-Duox1 and Ce-Duox2.

Export signal sequences were predicted according to Nielsen et al., 1997. Transmembrane alpha helices were predicted according to Sonnhammer et al., 1998. Both methods are available on the internet at the Center for Biological Sequence Analysis (http://www.cbs.dtu.dk/services/). Multiple sequence alignments phylogenetic analysis were carried out using the clustal method, using Megalign software (DNASTAR).

The domain structure and transmembrane regions in gp91phox, h-Duox1, hDuox2, Ce-Duox1 and Ce-Duox2 are diagrammed in FIG. 1. Duox enzymes are homologous to gp91phox in their C-termini (see http://www.biochem.emory.edu/Lambeth/gp91_homology.pdf for an alignment of these regions). Nox1 (Suh et al., 1999), which is the same size as gp91phox, is more closely related to gp91phox (54% identical) than is the NADPH-oxidase domain of hDuox1 or hDuox2 (~26 % identical to gp91phox). However, h-Duox1 and hDuox2 are more closely related to Ce-Duox1 within the NADPH-oxidase domain (~39% identical). Within the putative FAD binding regions and NADPH binding regions, homologs share considerably higher homology, ranging from 60% to 90%, depending on the region. This includes the canonical dinucleotide binding helix GXGXXP (SEQ ID NO: 18). In gp91phox, Nox1, h-Duox1, and h-Duox2 this sequence is followed by F, which is present in many NADPH-specific flavoproteins, while in the C. elegans proteins, F is conservatively replaced with Y.

Duox proteins have additional regions that are not present in gp91phox. A central region contains two EF hand calcium binding sequences, as indicated in FIG. 1. The canonical residues involved in calcium ligation are well conserved in h-Duox1 and h-Duox2, but are poorly conserved in Ce-Duox1 and Ce-Duox2, suggesting that the function of this region may have evolved away from calcium binding in nematodes.

Figure 2B:
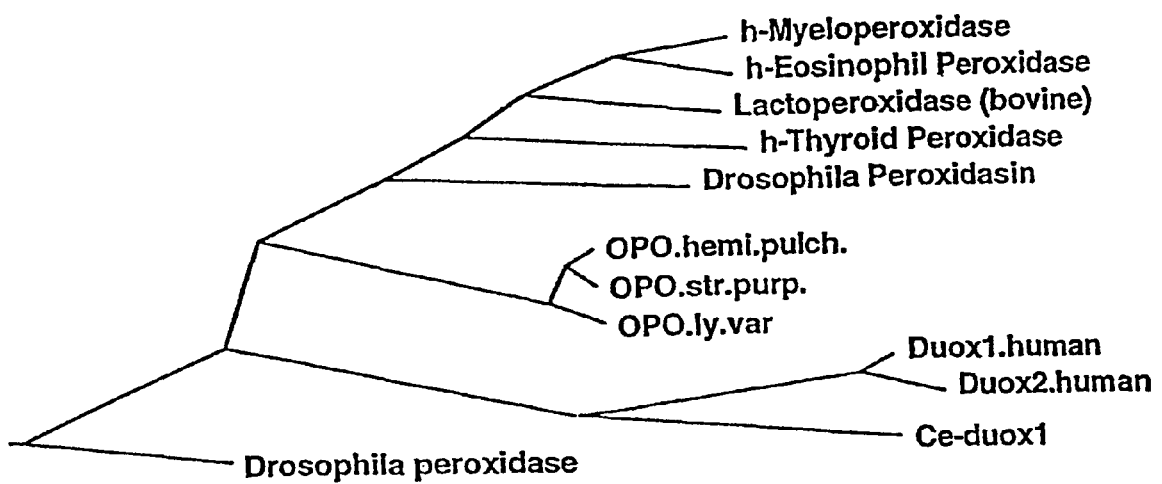
Figure 3:
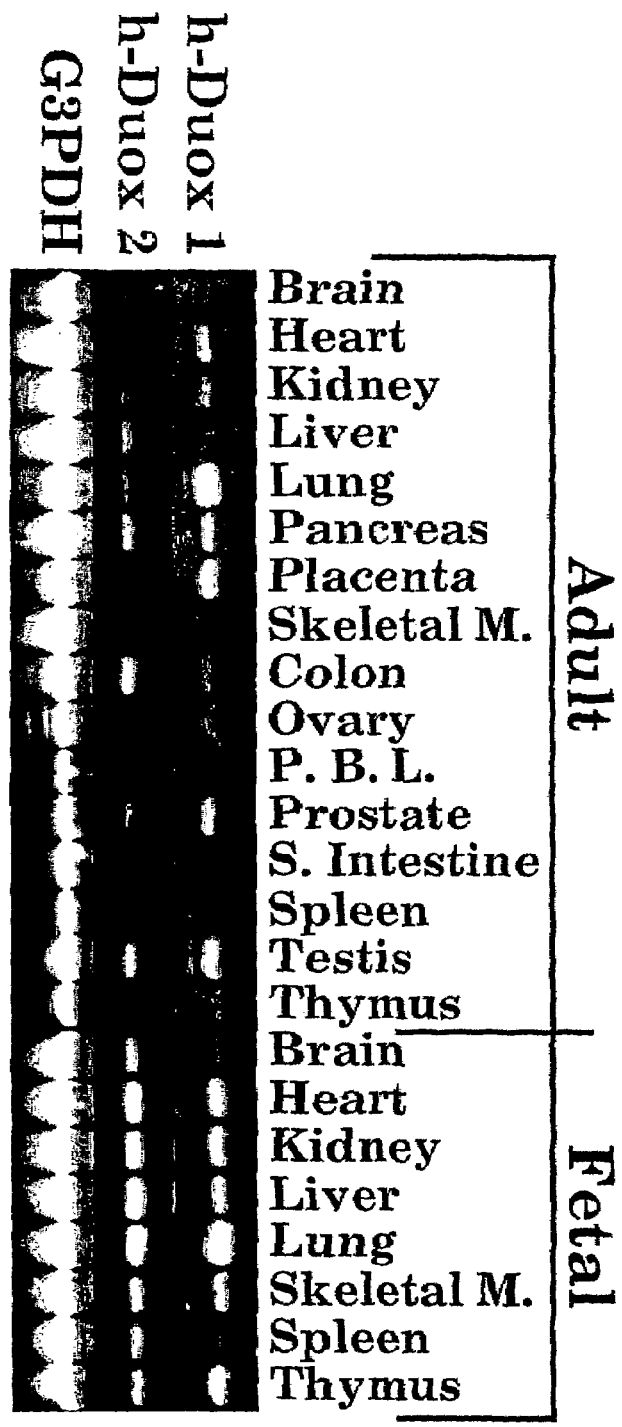
FIG. 3. Tissue expression of mRNA for h-Duox. mRNA for h-Duox1, h-Duox2 and glyceraldehyde 3-phosphate dehydrogenase was detected by RT-PCR.

Surprisingly, the N-terminal third of Duox proteins is homologous to peroxidases including myeloperoxidase, eosinophil peroxidase, thyroid peroxidase, lactoperoxidase and sea urchin ovoperoxidases (FIGS. 2A and 2B). Overall, the identity with peroxidases within the entire region is approximately 20%, but sub-regions show considerably higher homology. The Duox enzymes represent a distinct group within the peroxidase family (FIG. 2B), and phylogenetically, this group is marginally more closely related to sea urchin ovoperoxidases. Within the peroxidase homology region, only 2 of the 12 cysteine residues involved in the six intra-chain disulfide bonds, which are conserved in the four homologous mammalian peroxidases, are present in Duox proteins (not shown). In addition, the asparagine-linked glycosylation sites found in MPO are not present in Ce-Duox1 or Ce-Duox2. A calcium binding site in MPO (aspartate 263 and residues 335 to 341, superior double bar in FIG. 2A) (Zeng and Fenna, 1992) is well conserved in the Duox family proteins, including 3 of the 4 candidate calcium liganding residues (filled triangles).

The extreme N-terminal 21 amino acids of Ce-Duox1 contains a secretory signal peptide sequence (FIG. 1), implying that the N-terminal peroxidase domain is in a compartment that is transmembrane to the cytosol (e.g., extracellular or within a secretory vesicle). In addition, hydropathy plots reveal that the proteins contain a highly hydrophobic region corresponding to the N-terminal third of gp91phox. This region can be modelled as a cluster of 6 transmembrane alpha helices, as indicated in FIG. 1. An additional transmembrane helical region is present between the peroxidase homology domain and the calmodulin-like domain.

EXAMPLE 4

PCR Detection of mRNA for Human Duox, Tissue Distribution of h-Duox mRNA.

Based on the cloned h-Duox1 and hDuox2 cDNA sequence, we designed specific primers (Duox1: 5'-GCAGGACATCAACCCTGCACTCTC-3' (SEQ ID NO:19); 5'-CTGCCATCTACCACACGGATCTGC-3' (SEQ ID NO:20); Duox2: 5'-GCCCTCAACCTAAGCAGCTCACAACTG-3' (SEQ ID NO:21); 5'-GAGCACAGTGAGATGCCTGTTCAG-3') (SEQ ID NO:22) which were used to determine the tissue expression patterns of Duox1 and Duox2 using Human Multiple Tissue PCR Panels and human thyroid gland Marathon-Ready cDNA (Clontech, Palo Alto, Calif.). PCR conditions were: 95° C. for 30 s, 65° C. for 20 s, 72° C. for 30 s, 35 cycles.

h-Duox1 mRNA was distributed among a variety of adult tissues, with highest expression in lung and thyroid, but with significant expression also seen in placenta, testis, and prostate with detectable expression in pancreas and heart. h-Duox1 mRNA was also widely expressed in fetal tissues, where it was abundant in lung. In addition, we observed significant expression in a variety of fetal tissues and in adult colon, with detectable expression in kidney, liver, lung, pancreas, prostate and testis.

h-Duox2 mRNA was distributed among a variety of adult tissues, with highest expression in colon, testis, pancreas and thyroid. h-Duox2mRNA was also widely expressed in fetal tissues, where it was abundant in lung, liver, kidney, and heart, and thyroid. We also observed significant expression in fetal skeletal muscle and thymus.

EXAMPLE5

RNA Interference (RNAi) in *C. elegans* Phenotypes of *C. elegans* RNAi Ce-Duox Animals To gain insights regarding the biological function of Duox enzymes, we used the reverse genetic tool, RNA interference (RNAi), to "knock out" Duox in *C. elegans* (Fire et al., 1998). This technique involves injection of double stranded RNA (dsRNA) encoding a segment of Ce-Duox1 or Ce-Duox2 into gonads of *C. elegans* wild type hermaphrodites. Injected animals were then allowed to lay eggs, the harvested eggs were allowed to develop, and the progeny were observed for phenotypes. This procedure specifically diminishes or eliminates the expression of the gene of interest.

RNA was transcribed from either pBluescript.Duox2, pBluescript.E17Duox1 or pBluescript.E 18+19Duox1. For pBluescript.Duox2, Exon 10 of Ce-Duox2 was amplified by PCR from genomic DNA using the forward primer 5'-GCTAGAGCTCTTCAGTTTGCTATGGAATTGGC-3' (SEQ ID NO:23) and reverse primer 5'-CATAAAGGAT-GAGGAGAATTCTGTG-3' (SEQ ID NO:24). The 457-bp fragment generated was digested with SstI and EcoRI and subcloned into pBluescript. For pBluescript.E17Duox1, Exon 17 of Duox1 was amplified by PCR from genomic DNA using the forward primer 5'-GCTAGAGCTCGGC-TACTACTACGTTGTTGGACC-3' (SEQ ID NO:25) and the reverse primer 5'-GACTGAAGGACTTGTG-GAACGTCTGAGTGAC-3' (SEQ ID NO:26). The 659 bp fragment generated was digested with SstI and EcoRI and sub cloned into pBluescript. For pBluescript.E18+19Duox1, Exons 18 and 19 of Ce-Duox1 were amplified by PCR from a randomly primed *C. elegans* cDNA library (obtained from R. Barstead, Oklahoma Medical Research Foundation) using the forward primer 5'-GCTAGAGCTCACATTTGC-GAGAAGCACTTCCG-3' (SEQ ID NO: 27) and the reverse primer 5'-GTGTGAATTCAGCGATGTGCAAATGAAG-GAGC-3' (SEQ ID NO: 28). The 266 bp fragment generated was digested with SstI and EcoRI and subcloned into pBluescript. Plasmids were linearized with either Sst1 or EcoR1 and transcription was carried out using T3 and T7 RNA polymerase (Promega) in separate reactions. Sense and antisense single-stranded RNAs were combined in equal concentrations, and incubated for 10 min at 68° C. followed by a 30 min incubation at 37° C. to form double stranded RNA (dsRNA). dsRNAs were injected into the gonads of N2 hermaphrodite *C. elegans* as described in detail in the following paragraph. Injected animals were allowed to recover and lay eggs for ~20 h after injection, transferred to individual plates, and allowed to lay eggs for a second 24 h period. The F1 progeny resulting from this second period of egg laying were evaluated. Phenotypes were observed in >90% of F1 animals.

Phenotypes of *C. elegans* RNAi Ce-Duox Animal dsRNA corresponding to three distinct regions of Ce-Duox1 and Duox2 were used in separate experiments. The first two correspond to regions of identity between Ce-Duox1 and Ce-Duox2 and are predicted to block the expression of both forms of Duox. The third dsRNA corresponds to the extreme C-terminus of Ce-Duox1, which does not have a counterpart in Ce-Duox2, and therefore blocks only the expression of Ce-Duox1. All three dsRNA forms resulted in the same range of phenotypes. In replicate experiments, the percentage of animals exhibiting any given phenotype was somewhat variable, probably due to differences in amount of RNAi or site of injection. However, in a typical experiment, greater than 90% of the animals were affected by one or more phenotypes. In a typical experiment, phenotypes included the presence of large superficial blisters (~50% of animals) and short or "dumpy" animals (~35% of animals), and animals with retained eggs or larvae (not shown). In addition, while wild type animals showed a dark appearance, more than 80% of RNAi animals were translucent. Around half of RNAi animals showed an inability to move on plates in a normal serpentine manner: affected animals were either completely paralyzed or moved only the anterior region, clearing a localized swath of *E. coli* in the vicinity of the head.

Similar phenotypes in *C. elegans* have been described previously and are associated with mutations in the collagen biosynthetic pathway (Levy et al., 1993; Kramer, 1997; Johnstone, 2000). Several genes that encode cuticle collagens, when mutated, result in Bli ("blister"), Dpy ("dumpy", short fat worm), Rol ("roller", helical motion instead of a flat, sinusoidal motion), or Sqt ("squat", generally rollers as larvae and dumpy as adults) phenotypes. The genetics of this process are complex, since for some genes, different mutations in the same gene give rise to different phenotypes, and sometimes the phenotypes are combined (e.g. "dumpy roller") in nematodes, collagen along with several other proteins provide the major components of cuticle, an extracellular matrix which acts as an exoskeleton.

In a global analysis of expression of all *C. elegans* genes using oligonucleotide arrays (Hill et al., 2000), Ce-Duox1 was expressed at low levels (consistent with its exclusive expression in hypodermal cells) in a stage-specific manner. Expression occurred in a cyclic pattern peaking during the embryonic stage and at 36 hours, corresponding to the peak expression of other genes (Johnstone, I. L., 2000) related to collagen/cuticle biosynthesis (col-14, dpy-2, -7, -10, and sqt-3). A second set of collagen/cuticle-related genes (bli-1, -2, col-2, -6, -17, -35, -36, -37, -41, dyp-13, sqt-1, and rol-6, -8) also show peak expression at 36 hours. No significant expression of Ce-Duox2 was seen at any stage. Thus, these data are consistent with a function of Ce-Duox1 in cuticle biogenesis.

EXAMPLE 6

Generations of Transgenic Nematodes to Study Ce-Duox1 Expression

DNA from pPD96.62PRODuox1B was mixed with myo-3-GFP DNA (kindly provided by A. Fire, Carnegie Institute of Embryology, Baltimore, Md.) and injected into wild type or rol-6(su1006) young adult hermaphrodites (Mello and Fire, 1995). Transformants were identified by screening the F1 progeny under a fluorescence dissecting microscope for green body wall muscle. These green glowing animals were stained for β-galactosidase expression, as described below. Although pPD96.62 was expected to have driven both n-galactosidase and green fluorescent protein (GFP) expression, no fluorescence was observed outside of body wall muscle (the site of expression of the marker Myo-3-GFP). pPD96.62PRODuox1B was prepared as follows: a 3389 bp fragment was amplified by long range PCR from C. elegans genomic DNA using the forward primer 5'-AGTC-GAAGCTTAGCATGTCAAAGTCCGGAGTTCAGT-3' (SEQ ID NO:29) and the reverse primer 5'-CTAGTGGATC-CGCATTGCTCGTGCGCCTTAGAGTTT-3' (SEQ ID NO:30). The fragment included the start methionine of Ce-Duox1 and 5' untranslated sequence. The fragment was digested with HindIII and BamHI and then subcloned into pPD96.62. This construct results in the Ce-Duox1 promoter region (3389 bp) and the start methionine being inserted 5' of E. coli lacZ gene fused to the green fluorescence protein (GFP) reported gene.

β-Galactosidase Staining

Staining was used to detect expression of the gfp:lacZ fusion protein in transgenic worms carrying pPD96.62PRODuox1B. Reagent preparation and fixation were performed as described by Fire (1993). Vectors also incorporated a nuclear localization peptide at the N-terminus of β-galactosidase. This allows predominant staining in the nuclei of expressing cells and facilitates their identification. Nematodes were placed into individual wells of an eight well microscope slide with ~15 μl of distilled water and dried under vacuum for 2–3 min. Acetone was continuously dripped onto the dried animals for 2 min. The slide was placed in an uncovered humidity chamber, but kept dry. 10 μl of β-galactosidase stain (Fire, 1993) was layered onto each well as soon as the acetone had completely evaporated and the lid to the humidity chamber was replaced. The nematodes were then incubated at room temperature for several hours, washed several items in phosphate buffered saline, and then observed with a compound microscope.

Cellular Expression of Ce-Duox1

The cellular location of Ce-Duox1 in C. elegans was determined by double staining with antibodies to Ce-Duox1 and to myosin A (a marker for body wall muscle cells). Ce-Duox1 was seen in larval animals in the hypodermal layer of cells immediately overlying the myosin A-containing muscle cells, and was only faintly detectable in hypodermal cells that did not overlie muscle quadrants. In adult animals, Ce-Duox1 was poorly detected (not shown). The strong signal seen in larval animals was eliminated using anti-Ce-Duox1 antibody that had been preincubated with Ce-Duox1 peptide.

EXAMPLE 7

Antibody Production and Purification

A 16 amino acid peptide corresponding to residues 340–355 of Ce-Duox1 was synthesized by the Emory Microchemical Facility and coupled using gluteraldehyde to keyhole limpet hemocyanin (KLH). Rabbit antibody was prepared against KLH-conjugated peptide by Lampire Biological Laboratories (Pipersville, Pa.) using standard protocols. Peptide (30 mg) was coupled to 1 ml of Affi-Gel 10 (Bio-Rad) for antibody immunopurification; 2 ml of serum was dialyzed against PBS and was loaded onto the Affi-Gel column preequilibrated with PBS. The column was washed with 10 ml PBS containing 1M NaCl. 0.5 ml factions of antibody were eluted with 0.1M glycine-HCl (pH 2.4) and were immediately neutralized with TRIS, pH 9. Fractions containing the highest concentration of protein were used in immunofluorescence experiments.

EXAMPLE 8

Western Blot

Nematodes were washed with M9 buffer, suspended in 0.5 ml sonication buffer (10 mM Tris HCl, pH 7.4, 1 mM EDTA, 1 mM phenylmethanesulfonyl fluoride), and sonicated 4×20 s. Protein was determined with the Bradford assay using bovine serum albumin as a standard. 10 μg of whole animal extract was loaded onto a 10% SDS-page gel which was then transferred to Immobilon-P membrane (Millipore). The blot was blocked for 1 hour in a solution of 5% nonfat powdered milk and 0.05% Tween in PBS. The antibody to Ce-Duox1 was added in a 1 to 2000 dilution, incubated overnight, and the membrane was washed 3 times for 15 min with blocking solution. The blot was then developed using the SuperSignal Chemiluminescent Kit from Pierce (Rockford, Ill.). A western blot of C. elegans protein extract showed a single band with a molecular weight of ~180,000 (data not shown).

EXAMPLE 9

Indirect Inmmunofluorescence

Inmmunofluorescence staining of C. elegans was carried out as in Benian et al., 1996. Mouse antibody to Myosin A was a gift from D. Miller (Miller et al., 1983). Goat anti-rabbit rhodamine-conjugated antibody and goat anti-mouse FITC-conjugated antibody were used as secondary antibodies for the detection of Ce-Duox1 and Myosin A respectively. To determine non-specific binding of the Ce-Duox1 antibody, a 10 fold molar excess of Ce-Duox1 peptide was added to neutralize the antibody. Microscopy was carried out using Zeiss 510 laser scanning confocal microscope.

EXAMPLE 10

Preparation of Dityrosine Standard

Dityrosine standard was synthesized and purified as in Abdelrahim et al., 1997 with minor modifications. Reaction products were dissolved in acidified methanol, were filtered, and directly applied to the CP-11 cellulose phosphate, eliminating the rotary evaporation step. Samples with absorption properties characteristic of dityrosine were pooled and freeze dried. For mass spectrometry, the 1 ml of dityrosine standard (0.77 mg/ml) was added to 1 ml of methanol:water (1:1) in 0.1% acetic acid.

Analysis of Dityrosine and Trityrosine

Nematodes were washed with M9 buffer, suspended in 0.5 ml sonication buffer (10 mM Tris HCl, pH 7.4, 1 mM EDTA, 1 mM phenylmethanesulfonyl fluoride), and sonicated 4×20 s. Protein was determined with the Bradford assay using bovine serum albumin as a standard. Whole worm extracts were lyophilized and resuspended in 6 N HCl. Samples were hydrolyzed for 24 h at 110° C. under vacuum, dried under vacuum and resuspended in the mobile phase for analysis by high performance liquid chromatography (HPLC) on a C18 column (0.46×26 cm, Fisher) using a Dionex AGP-1 HPLC instrument. The mobile phase consisted of 0.1 M $KH_2PO_4$ adjusted to pH 3.8 with 0.1 M phosphoric acid at a flow rate of 1 ml/min. The column eluent was monitored by fluorescence with an excitation 305–395 nm bandpass filter and an emission filter at 450 nm with a bandpass of 40 nm. To verify the identity of dityrosine, authentic dityrosine standard was added to some samples and an increase in the intensity of the putative dityrosine band was observed (data not shown).

Spectroscopic Properties of Di- and Trityrosine

HPLC purified samples of dityrosine and trityrosine from both *C. elegans* extracts and peroxidase domain cross-linking reactions were lyophilized and resolubilized in either 0.1 M HCl (3 ml) or 0.1 M NaOH (3 ml). Fluorescence excitation and emission spectra were obtained with a Perkin-Elmer LS-5B Luminescence Spectrometer.

Mass Spectrometry

Mass spectrometry was preformed on a PE sciex API 3000 triple quadrupole mass spectrometer equipped with a turboionspray source. Dried dityrosine standard (20 mg) was reconstituted in 200 µl of $H_2O$. A 50 µl aliquot of this was diluted to a final volume of 1 ml with 950 µl of 5 mM ammonium acetate in MeOH and 1% acetic acid. This solution infused at a flow rate of 5 µl min$^{-1}$. The ionspray needle was held at +550V and −4500V for positive and negative ion analysis, respectively. These experiments identified the singly protonated (positive ion mode) and deprotonated (negative ion mode) species of the standard to be m/z 361.3 and 359.3 respectively as predicted.

Standard and total protein acid hydrolysate from *C. elegans* were analyzed by reverse phase LC-MS/MS. A 50 µl volume of sample was injected onto a 15 cm×2.1 mm Supelco Discovery C18 column at a flow rate of 300 µl min$^{-1}$. Solvent A was 99:1 $H_2O$/acetic acid and solvent B was 99:1 MeOH/acetic acid both containing 5 mM ammonium acetate. The column was directly infused into the ion source of the mass spectrometer operating in positive ion mode. The column was pre-equilibrated with 100% A for 6 min followed by sample injection. The column was then washed with 100% A for 4 min and eluted with a 1 min linear gradient to 100% B, followed by a 4 min wash with 100% B. For these experiments both the precursor ions (as above for dityrosine; m/z 540.4/538.4 for trityrosine) and structurally distinctive breakdown ions were monitored. The transitions monitored for dityrosine were the neutral loss of both carboxyl groups, the neutral loss of both carboxyl groups and one amino group, and the neutral loss of both carboxyl groups and both amino groups (m/z 269.4, 252.2, and 235.0 respectively). For trityrosine, the transitions monitored were the neutral loss of a carboxyl groups, the neutral loss of a carboxyl group and one amino group, the neutral loss of two C-termini, and the neutral loss of two carboxyl groups and two amino groups (m/z 494.3, 477.2, 448.2, and 431.2 respectively).

Absence of Tyrosine Cross-linking in RNAi Nematodes

Cross-linking of collagen and other cuticle proteins in nematodes occurs through di- and tri-tyrosine linkages which bridge and stabilize the proteinaceous structure (Fetterer et al., 1993; Fetterer and Rhoads, 1990). Because peroxidases such as sea urchin ovoperoxidase and human myeloperoxidase carry out this reaction (Malanik and Ledvina, 1979; LaBella et al., 1968; Deits et al., 1984), we hypothesized that the function of Ce-Duox1 is to generate tyrosine cross-links, and that the defective cuticle in the Ce-Duox RNAi animals is due to an inability to form tyrosine cross-links. A role for an unknown peroxidase in tyrosine cross-linking in Ascaris was previously suggested based on studies in which tyrosine cross-linking activity was inhibited using the peroxidase inhibitors 4-amino-2,3,4 aminotriazole, phenylhydrazine, and N-acetyl tyrosine (Fetterer et al., 1993). We therefore examined the wild-type and Ce-Duox1 RNAi knockout animals for di- and tri-tyrosine linkages. An HPLC profile of an acid hydrolysate of the wild-type *C. elegans* revealed a first large peak which was identified as dityrosine based on comparison with authentic standard and mass spectral analysis, and the second peak is identified as trityrosine based on its migration on HPLC relative to dityrosine and mass spectral analysis. Based on peak areas and assuming equivalent ionization, dityrosine and tyrosine were present in a ratio of 1:200 in adult wild-type animals. In addition, the fluorescence excitation/emission maxima were determined at alkaline and acidic pH and were in good agreement with previously reported values (Jacob, et al. 1996). Neither the dityrosine nor the trityrosine peaks were detected in hydrolysates of Ce-Duox RNAi nematodes.

EXAMPLE 11

Participation of Duox in Cuticle Biogenesis, Ultrastructural Analysis

The similarity in phenotypes among animals defective in collagen and cuticle biosynthesis compared with the RNAi Duox animals suggested that Duox participates in cuticle biogenesis. To confirm this hypothesis, electron microscopy was carried out on wild-type and RNAi animals.

Wild type or RNAi blistered adult *C. elegans* were collected and washed first with M9 buffer and then with 0.1 M cacodylate buffer (pH 7.4). Animals were pelleted, added to 1 ml of 0.8% glutaraldeyde, 0.7% osmium tetroxide, 0.1 M cacodylate pH 7.4 and incubated on ice for 1.5 hours with occasional mixing. The animals were washed with 0.1 M cacodylate buffer, transferred to a glass depression slide and cut in half with a 23 gauge needle. Bisected animals were transferred into a tube containing 1 ml of fresh fixative (0.8% glutaraldeyde, 0.7% osmium tetroxide, 0.1 M cacodylate pH 7.4) and incubated on ice for 2 hrs. After washing with 0.1 M cacodylate buffer, the bisected animals were fixed overnight on ice in 1% osmium tetroxide in 0.1 M cacodylate buffer. Animals were washed several times in 0.1 M cacodylate buffer, dehydrated using graded alcohols through propylene oxide, infiltrated and embedded in Embed-812 (Electron Microscopy Sciences, Ft. Washington, Pa.). The animals were teased into parallel arrangement with an eyelash probe prior to polymerization at 60° C. for 16 hours. Sections (0.5 mm) were evaluated for orientation and ultrasections (800 Å thick) were collected on 200 mesh copper grids, stained with uranyl acetate and lead citrate, and cross sections were examined with a Philips EM201 electron microscope.

Ultrastructural analysis revealed that cuticle of RNAi Duox animals was grossly abnormal In normal animals three cuticle layers were seen clearly: the cortical (outer), median and basal (inner) layer, as described previously (Cox, G. N., et al., 1981). The median layer is composed of struts connecting the cortical and basal layers, with a fluid-filled space between these layers. The RNAi animals frequently showed separation between the cortical and the basal layers, with marked expansion of the fluid cavity and broken and distended struts that were still visible on these layers. These separations occurred mainly over bundles of muscle fiber and are likely to account for the formation of the blisters observed using light microscopy. Thus, the cuticle structure was severely affected in RNAi Duox animals.

EXAMPLE 12

Construction of Duox Peroxidase Domain Expression Plasmids

The polymerase chain reaction was used to amplify the peroxidase domains of h-Duox (amino acid residues 1–593, SEQ ID NO:31) and Ce-Duox (amino acid residues 1–590, SEQ ID NO:32) from the cloned full length sequences. The primers were designed to introduce an N-terminal BamH I site and a C-terminal Not I site. PCR products were digested with BamH I and Not I and ligated into the pET-32a(+) vector from Novogen (Madison, Wis.). Plasmids were transformed into BL21(DE3) cells containing the chloramphenicol-resistant plasmid pT-groE (Yasukawa, et al., 1995), which expresses the chaperonins groES and groEL from the T7 promoter. The pT-groE expression vector in BL21(DE3) cells was a generous gift from Dr. Lee-Ho Wang (University of Texas Health Science Center, Houston, Tex.) and Dr. Shunsuke Ishii (Institute of Physical and Chemical Research, Ibaraki, Japan). LB-agar plates containing both ampicillin and chloramphenicol were used to isolate colonies.

Expression of Duox Peroxidase Domains

A 0.5 ml LB overnight culture of cells containing plasmid with the peroxidase domain from h-Duox or Ce-Duox was used to inoculate 50 ml of modified TB medium (Sandhu et al., 1993) containing 0.5 mM d-aminolevulinic acid, 100 mg/ml ampicillin and 25 mg/ml chloramphenicol in a 250 ml flask. Bacteria were grown at 37° C. in a shaker at 200 RPM until the cell density measured 0.7 OD at 600 nm. Isopropyl-b-D-thiogalactopyranoside (1 mM) was added and the culture was continued at 25° C. for 24 hours at 150 RPM. Cells were pelleted at 4,500×g and resuspended in PBS containing 4-(2-aminoethyl)benzenesulfonyl fluoride (2 nM), bestatin (130 nM), trans-epoxysuccinyl-L-leucyl-amido(4-guanidino)butane (1.4 nM) leupeptin (1 nM) and aprotinin (0.3 nM). The cell suspension was then sonicated on ice.

Biochemical Activities of the Expressed Peroxidase Domains of Ce-Duox1 and h-Duox1

The peroxidase domains of Ce-Duox (residues 1–590, SEQ ID NO:32) and h-Duox1 (residues 1–593, SEQ ID NO:31) were expressed in *E. coli*, as described above. A lysate from these cells was analyzed for peroxidase activity. The results showed that the lysates from *E. coli*, expressing both the human and the *C. elegans* peroxidase-homology domains from Duox, demonstrated peroxidase activity towards TMB, a well-characterized peroxidase substrate. The activity was inhibited by the peroxidase inhibitor aminobenzohydrazide. Lysates from *E. coli* expressing the peroxidase domains of h-Duox and Ce-Duox, but not those from vector control cells, also catalyzed the cross-linking of tyrosine ethyl ester. Two major fluorescent products were seen, as were also seen in hydrolysates of cuticle protein; peak 1 was identified by co-chromatography with authentic material and mass spectral analysis as dityrosine, while peak 2 was identified as tri-tyrosine by mass spectral analysis as above.

EXAMPLE 13

Activity Assays

The 3,3', 5,5'-tetramethylbenzidine (TMB) liquid substrate system (Sigma, St. Louis, Mo.) was used to assay peroxidase activity (Holland et al., 1974). To 1 ml aliquots of the TMB substrate system 100 mg of lysate protein from cells expressing either the human Duox1 peroxidase domain, Ce-Duox1 peroxidase domain or a vector control was added. The peroxidase reactions were performed in triplicate and activity was monitored at 655 nm with a Beckman DU640B spectrophotometer. Some samples contained 30 mM aminobenzoic acid hydrazide, a peroxidase inhibitor (Kettle et al 1995).

To assay tyrosine cross-linking, tyrosine ethyl ester (20 mM) was dissolved in 10 ml of PBS buffer supplemented with 80 ml of 3% $H_2O_2$. To 1 ml aliquots, 100 mg of *E. coli* lysate protein was added, samples were incubated for 1 hour, and the reaction was quenched using an equal volume of 12 M HCl. Samples were analyzed for di- and tri-tyrosine as above.

NADPH-Dependent Superoxide Generation Assay

In one embodiment of the present invention, NIH 3T3 cells stably transfected with the human duox2 gene (SEQ ID NO:1) are analyzed for superoxide generation using the lucigenin (Bis-N-methylpyridinium luminescence assay (Sigma, St. Louis, Mo., Li et al. (1998) *J. Biol. Chem.* 273, 2015–2023). Cells are washed with cold HANKS' solution and homogenized on ice in HANKS' buffer containing 15% sucrose using a Dounce homogenizer. Cell lysates are frozen immediately in a dry ice/ethanol bath. For the assay, 30 μg of cell lysate is mixed with 200 μM NADPH and 500 μM lucigenin. Luminescence is monitored using a LumiCounter (Packard) at three successive one minute intervals and the highest value is used for comparison. Protein concentration is determined by the Bradford method.

Superoxide generation is monitored in lysates from some of the stably transfected cell lines and was compared with superoxide generation by the untransfected NIH 3T3 cell lysates. The results are show that the transfected cells possess the highest degree of morphological changes by microscopic examination corresponding to the highest degree of superoxide generation. The luminescent signal is inhibited by superoxide dismutase and the general flavoprotein inhibitor diphenylene iodonium, but is unaffected by added recombinant human p47phox, p67phox and Rac1 (GTP-γS), which are essential cytosolic factors for the phagocyte respiratory-burst oxidase.

In an alternate embodiment of the present invention, cells that are stably transfected with hduox2 (YA28) or with empty vector (NEF2) are grown in 10 cm tissue culture plates in medium containing DMEM, 10% calf serum, 100 units/ml penicillin, 100 μg/ml streptomycin, and 1 μg/ml puromycin to approximately 80% confluency. Cells (five tissue culture plates of each cell type) are washed briefly with 5 ml phosphate buffered saline (PBS) then dissociated from the plates with PBS containing 5 mM EDTA. Cells are pelleted by centrifuging briefly at 1000×g.

To permeabilize the cells, freeze thaw lysis is carried out followed by passage of the cell material through a small bore needle. The supernatant is removed and the cells frozen on dry ice for 15 minutes. After cells thaw, 200 μl lysis buffer (HANKS' Buffered Salt Solution—HBBS) containing a mixture of protease inhibitors from Sigma (Catalog #P2714) is added. Cells on ice are passed through an 18 guage needle 10 times and 200 μl of HBSS buffer containing 34% sucrose was added to yield a final concentration of 17% sucrose.

Sucrose appears to enhance stability upon storage. The combination of freeze-thawing and passage through a needle results in lysis of essentially all of the cells, and this material is referred to as the "cell lysate."

The cell lysates are assayed for protein concentration using the BioRad protein assay system. Cell lysates are assayed for NADPH-dependent chemiluminescence by combining HBSS buffer, arachidonic acid, and 0.01–1 μg protein in assay plates (96 well plastic plates). The reaction is initiated by adding 1.5 mM NADPH and 75 μM lucigenin to the assay mix to give a final concentration of 200 μM NADPH and 10 μM lucigenin, and the chemiluminescence is monitored immediately. The final assay volume is about 150 μl. The optimal arachidonic acid concentration is between about 50–100 μM. A Packard Lumicount luminometer is used to measure chemiluminescence of the reaction between lucigenin and superoxide at 37° C. The plate is monitored continuously for 60 minutes and the maximal relative luminescence unit (RLU) value for each sample is plotted. Results show that the presence of NaCl or KCl within a concentration range of 50–150 μM is important for optimal activity. $MgCl_2$ (1–5 mM) further enhances activity by about 2-fold. This cell-free assay for duox2 NADPH-oxidase activity is useful for screening modulators (inhibitors or stimulators) of the duox2 enzyme. The assay may also be used to detect and duox NADPH-oxidase activity in general and to screen for modulators (inhibitors or stimulators) of the duox family of enzymes.

Nitro Blue Tetrazolium Reduction by Superoxide Generated by NIH 3T3 Cells Transfected with the Duox2 cDNA (SEQ ID NO:1)

Superoxide generation by intact cells is monitored by using superoxide dismutase-sensitive reduction of nitroblue tetrazolium. NEF2 (vector alone control), YA26 (duox2 (SEQ ID NO:1)-transfected) and YA28 (duox2 (SEQ ID NO:1)-transfected) cells are plated in six well plates at 500,000 cells per well. About 24 hours later, medium is removed from cells and the cells are washed once with 1 mL Hanks solution (Sigma, St. Louis, Mo.). About 1 mL of filtered 0.25% Nitro blue tetrazolium (NBT, Sigma) is added in Hanks without or with 600 units of superoxide dismutase (Sigma) and cells are incubated at 37° C. in the presence of 5% $CO_2$. After 8 minutes the cells are scraped and pelleted at more than 10,000 g. The pellet is re-suspended in 1 mL of pyridine (Sigma) and heated for 10 minutes at 100° C. to solubilize the reduced NBT. The concentration of reduced NBT is determined by measuring the absorbance at 510 nm, using an extinction coefficient of 11,000 $M^{-1}$ $cm^{-1}$. Some wells are untreated and used to determine cell number.

The data indicate that the duox2 (SEQ ID NO:1)-transfected cells generated significant quantities of superoxide. Because superoxide dismutase is not likely to penetrate cells, superoxide must be generated extracellularly. The amount of superoxide generated by these cells is about 5–10% of that generated by activated human neutrophils.

EXAMPLE 14

Modification of Intracellular Components in Duox2 Transfected Cells

To test whether superoxide generated by duox2 can affect intracellular "targets", aconitase activity in control and duox-transfected cell lines is monitored using methods as described in Suh et al. (1999) Nature 401, 79–82. Aconitase contains a four-iron-sulphur cluster that is highly susceptible to modification by superoxide, resulting in a loss of activity, and has been used as a reporter of intra-cellular superoxide generation. Aconitnase activity is determined as described in Gardner et al. (1995) J. Biol. Chem. 270, 13399–13405. Acotinase activity is significantly diminished in all three duox-transfected cell lines designated YA26, YA28 and YA212 as compared to the transfected control. Approximately 50% of the aconitase in these cells is mitochondrial, based on differential centrifugation, and the cytosolic and mitochondrial forms are both affected. Control cytosolic and mitochondrial enzymes that do not contain iron-sulfur centres are not affected. Superoxide generated in duox2-transfected cells is therefore capable of reacting with and modifying intracellular components.

EXAMPLE 15

Tumor Generation in Nude Mice Receiving Cells Transfected with the Human Duox2 cDNA (SEQ ID NO:1)

About $2\times10^6$ NIH 3T3 cells (either hduox2-transfected with SEQ ID NO:1 or cells transfected using empty vector) are injected subdermally into the lateral aspect of the neck of 4–5 week old nude mice. Three to six mice are injected for each of three duox1-transfected cell lines, and 3 mice are injected with the cells transfected with empty vector (control). After 2 to 3 weeks, mice are sacrificed. The tumors are fixed in 10% formalin and characterized by histological analysis. Tumors averaged 1.5×1×1 cm in size and show histology typical of sarcoma type tumors. In addition, tumors appear to be highly vascularized with superficial capillaries. Eleven of twelve mice injected with duox2 gene-transfected cells develop tumors, while none of the three control animals develop tumors.

In another study, 15 mice are injected with duox2-transfected NIH 3T3 cells. Of the 15 mice injected, 14 show large tumors within 17 days of injection, and tumors show expression of duox1 mRNA. Histologically, the tumors resemble fibrosarcomas and are similar to ras-induced tumors. Thus, ras and duox2 are similarly potent in their ability to induce tumorigenicity of NIH 3T3 cells in athymic mice.

EXAMPLE 16

Demonstration of the Role of Duox2 in Non-Cancerous Growth

A role in normal growth is demonstrated in rat aortic vascular smooth-muscle cells by using antisense to rat duox2. Transfection with the antisense DNA results in a decrease in both superoxide generation and serum-dependent growth. Duox2 is therefore implicated in normal growth in this cell type.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. An isolated protein capable of producing superoxide or having peroxidase activity, wherein the protein comprises the amino acid sequence of SEQ ID NO:2, a fragment thereof, producing superoxide or having peroxidase activity or an addition thereto, a deletion thereof, or a conservative substitution thereof of no more than about 5% of the amino acid sequence, wherein the isolated protein is capable of producing superoxide, has peroxidase activity, reactions, or a combination thereof.

2. The isolated protein of claim 1 wherein the conservative substitution comprises substitution of
   a) alanine, serine, or threonine for each other;
   b) aspartic acid or glutamic acid for each other;
   c) asparagine or glutamine for each other;
   d) arginine or lysine for each other;
   e) isoleucine, leucine, methionine, or valine for each other; and
   f) phenylalanine, tyrosine, or tryptophan for each other.

3. An isolated protein comprising the amino acid sequence of SEQ ID NO:2 or a fragment thereof, wherein the isolated protein is capable of producing superoxide, has peroxidase activity, or a combination thereof.

4. An isolated nucleotide sequence encoding the protein, of claim 1.

5. An isolated nucleotide sequence encoding the protein of claim 3.

6. The isolated nucleotide sequence of claim 5, comprising SEQ ID NO: 1.

7. A vector comprising the nucleotide sequence of claim 5.

8. A vector comprising the nucleotide sequence of claim 4.

9. An isolated host cell comprising the vector of claim 7.

10. An isolated host cell comprising the vector of claim 8.

11. The isolated protein of claim 3, wherein the protein comprises the amino acid sequence according to SEQ ID NO:2.

12. A vector comprising the nucleotide sequence of claim 6.

13. An isolated host cell comprising the vector of claim 12.

14. The isolated host cell of claim 13, wherein the host cell is a eukaryotic cell.

15. The isolated host cell of claim 13, wherein the host cell is a prokaryotic cell.

16. The isolated protein of claim 3, wherein the protein comprises amino acids 1283–1548 of SEQ LID NO:2.

17. The isolated protein of claim 3, wherein the protein comprises amino acids 1–593 of SEQ ID NO:2.

18. The isolated host cell of claim 9, wherein the host cell is a eukaryotic cell.

19. The isolated host cell of claim 9, wherein the host cell is a prokaryotic cell.

20. The isolated host cell of claim 10, wherein the host cell is a eukaryotic cell.

21. The isolated host cell of claim 10, wherein the host cell is a prokaryotic cell.

* * * * *

SEQUENCE LISTING

<160> NUMBER OF SEQ ID NOS: 39

<210> SEQ ID NO 1
<211> LENGTH: 6375
<212> TYPE: DNA
<213> ORGANISM: Homo sapiens
<220> FEATURE:
<221> NAME/KEY: CDS
<222> LOCATION: (204)..(4850)

<400> SEQUENCE: 1

| | |
|---|---|
| ggtctgtcct gagccgacac ctgcacagtg gcgagaccaa ggacccagag agaaaggtga | 60 |
| gagtgcagcc ggggaggctg aggatcggcg gagctggaag agtgagggtg aaggcaagaa | 120 |
| gtagagcaca gaagcaaaga ttttaagagg aaagaagaca tttgaaccca acaccaccct | 180 |

```
aaaccacagg ctgcagggtt ggc atg ctc cgt gca aga cca gag gca ctg atg      233
                         Met Leu Arg Ala Arg Pro Glu Ala Leu Met
                           1               5                  10 ctc ctg gga gct ctt ctg act gga tcc ctg ggt cca tcg ggc agt cag        281
Leu Leu Gly Ala Leu Leu Thr Gly Ser Leu Gly Pro Ser Gly Ser Gln
                15                  20                  25 gac gca ctc tca ctg ccc tgg gaa gtg cag cgc tat gac ggc tgg ttt        329
Asp Ala Leu Ser Leu Pro Trp Glu Val Gln Arg Tyr Asp Gly Trp Phe
            30                  35                  40 aac aac ctg agg cac cac gag cgt ggt gct gtt ggc tgc cgg ttg cag        377
Asn Asn Leu Arg His His Glu Arg Gly Ala Val Gly Cys Arg Leu Gln
        45                  50                  55 cgc cgc gta cca gcc aat tac gcc gac ggt gtg tat cag gct ctg gag        425
Arg Arg Val Pro Ala Asn Tyr Ala Asp Gly Val Tyr Gln Ala Leu Glu
    60                  65                  70 gag ccg cag ctg ccc aac ccg cgc cgg ctc agc aac gca gcc acg cgg        473
Glu Pro Gln Leu Pro Asn Pro Arg Arg Leu Ser Asn Ala Ala Thr Arg
75                  80                  85                  90 ggc ata gcc ggc ctg ccg tcg ctc cac aac cgc acc gta ctg ggg gtc        521
Gly Ile Ala Gly Leu Pro Ser Leu His Asn Arg Thr Val Leu Gly Val
                95                 100                 105 ttc ttt ggc tac cat gtt ctt tcc gac gtg gtg agc gtg gaa acg ccc        569
Phe Phe Gly Tyr His Val Leu Ser Asp Val Val Ser Val Glu Thr Pro
            110                 115                 120 ggt tgc ccc gcc gag ttc ctc aac atc cgc atc cca cct gga gac ctc        617
Gly Cys Pro Ala Glu Phe Leu Asn Ile Arg Ile Pro Pro Gly Asp Leu
        125                 130                 135 gtg ttc gac ccc gac cag cgc ggg gac gtg gtg ctg ccc ttc cag agg        665
Val Phe Asp Pro Asp Gln Arg Gly Asp Val Val Leu Pro Phe Gln Arg
    140                 145                 150 agc cgc tgg gac ccc gag acc gga cgg agt ccc agc aac ccc cgg gac        713
Ser Arg Trp Asp Pro Glu Thr Gly Arg Ser Pro Ser Asn Pro Arg Asp
155                 160                 165                 170 ctg gcc aac cag gtg acg ggc tgg ctg gac ggc agc gcc atc tat ggc        761
Leu Ala Asn Gln Val Thr Gly Trp Leu Asp Gly Ser Ala Ile Tyr Gly
                175                 180                 185 tcc tcg cac tcc tgg agc gac gcg ctg cgg agc ttc tcg ggg gga cag        809
Ser Ser His Ser Trp Ser Asp Ala Leu Arg Ser Phe Ser Gly Gly Gln
            190                 195                 200 ctg gcg tcg ggg ccc gac ccc gct ttc ccc cga gac tcg cag aac ccc        857
Leu Ala Ser Gly Pro Asp Pro Ala Phe Pro Arg Asp Ser Gln Asn Pro
        205                 210                 215 ctg ctc atg tgg gcg gcg ccc gac ccc gcc acc ggg cag aac ggg ccc        905
Leu Leu Met Trp Ala Ala Pro Asp Pro Ala Thr Gly Gln Asn Gly Pro
```

```
            220                 225                 230
cgg ggg ctg tac gcc ttc ggg gca gag aga ggg aac cgg gaa ccc ttc    953
Arg Gly Leu Tyr Ala Phe Gly Ala Glu Arg Gly Asn Arg Glu Pro Phe
235                 240                 245                 250 ctg cag gcg ctg ggc ctg ctc tgg ttc cgc tac cac aac ctg tgg gcg   1001
Leu Gln Ala Leu Gly Leu Leu Trp Phe Arg Tyr His Asn Leu Trp Ala
                255                 260                 265 cag agg ctg gcc cgc cag cac cca gac tgg gag gac gag gag ctg ttc   1049
Gln Arg Leu Ala Arg Gln His Pro Asp Trp Glu Asp Glu Glu Leu Phe
            270                 275                 280 cag cac gca cgc aag agg gtc atc gcc acc tac cag aac atc gct gtg   1097
Gln His Ala Arg Lys Arg Val Ile Ala Thr Tyr Gln Asn Ile Ala Val
        285                 290                 295 tat gag tgg ctg ccc agc ttc ctg cag aaa aca ctc ccg gag tat aca   1145
Tyr Glu Trp Leu Pro Ser Phe Leu Gln Lys Thr Leu Pro Glu Tyr Thr
    300                 305                 310 gga tac cgt cct ttc cta gac ccc agc atc tcc ccg gaa ttt gtg gtg   1193
Gly Tyr Arg Pro Phe Leu Asp Pro Ser Ile Ser Pro Glu Phe Val Val
315                 320                 325                 330 gcc tct gag cag ttc ttc tct acc atg gtg ccc cct ggt gtc tac atg   1241
Ala Ser Glu Gln Phe Phe Ser Thr Met Val Pro Pro Gly Val Tyr Met
                335                 340                 345 aga aat gcc agc tgt cat ttc cgg aag gtc ctg aac aag ggt ttt caa   1289
Arg Asn Ala Ser Cys His Phe Arg Lys Val Leu Asn Lys Gly Phe Gln
            350                 355                 360 agc tcc caa gct ctc agg gtc tgc aac aac tac tgg att cgg gag aac   1337
Ser Ser Gln Ala Leu Arg Val Cys Asn Asn Tyr Trp Ile Arg Glu Asn
        365                 370                 375 ccc aat ctg aac agt acc cag gag gtg aat gag ctg ctg ctg gga atg   1385
Pro Asn Leu Asn Ser Thr Gln Glu Val Asn Glu Leu Leu Leu Gly Met
    380                 385                 390 gcc tcc cag att tcg gag ttg gag gac aac ata gtg gtt gaa gat ctg   1433
Ala Ser Gln Ile Ser Glu Leu Glu Asp Asn Ile Val Val Glu Asp Leu
395                 400                 405                 410 agg gat tac tgg cct ggc cct ggc aaa ttc tcc cgt aca gac tat gtg   1481
Arg Asp Tyr Trp Pro Gly Pro Gly Lys Phe Ser Arg Thr Asp Tyr Val
                415                 420                 425 gcc agc agc atc caa cgt ggc cga gat atg ggg ctg ccc agc tat agc   1529
Ala Ser Ser Ile Gln Arg Gly Arg Asp Met Gly Leu Pro Ser Tyr Ser
            430                 435                 440 cag gcc ctg ctg gcc ttt ggg ctg gac atc cca agg aac tgg agt gat   1577
Gln Ala Leu Leu Ala Phe Gly Leu Asp Ile Pro Arg Asn Trp Ser Asp
        445                 450                 455 ctc aac cct aat gtg gac ccc cag gtg ctg gag gcc aca gct gcc ctg   1625
Leu Asn Pro Asn Val Asp Pro Gln Val Leu Glu Ala Thr Ala Ala Leu
    460                 465                 470 tac aac cag gac cta tcc cag cta gag ctg ctc ctt ggg ggc ctc ctg   1673
Tyr Asn Gln Asp Leu Ser Gln Leu Glu Leu Leu Leu Gly Gly Leu Leu
475                 480                 485                 490 gag agc cat ggg gac cct gga ccc ctg ttc agt gcc att gtc ctc gac   1721
Glu Ser His Gly Asp Pro Gly Pro Leu Phe Ser Ala Ile Val Leu Asp
                495                 500                 505 cag ttt gta cgg ctg cgg gat ggt gac cgc tac tgg ttt gag aac acc   1769
Gln Phe Val Arg Leu Arg Asp Gly Asp Arg Tyr Trp Phe Glu Asn Thr
            510                 515                 520 agg aat ggg ctg ttc tcc aag aag gag att gaa gac atc cga aat acc   1817
Arg Asn Gly Leu Phe Ser Lys Lys Glu Ile Glu Asp Ile Arg Asn Thr
        525                 530                 535 acc ctg cgg gac gtg ctg gtc gct gtt atc aac att gac ccc agt gcc   1865
```

```
                                                        -continued

Thr Leu Arg Asp Val Leu Val Ala Val Ile Asn Ile Asp Pro Ser Ala
540                 545                 550 ctg cag ccc aat gtc ttt gtc tgg cat aaa ggt gca ccc tgc cct caa      1913
Leu Gln Pro Asn Val Phe Val Trp His Lys Gly Ala Pro Cys Pro Gln
555                 560                 565                 570 cct aag cag ctc aca act gac ggc ctg ccc cag tgt gca ccc ctg act      1961
Pro Lys Gln Leu Thr Thr Asp Gly Leu Pro Gln Cys Ala Pro Leu Thr
            575                 580                 585 gtg ctt gac ttc ttt gaa ggc agc agc cct ggt ttt gcc atc acc atc      2009
Val Leu Asp Phe Phe Glu Gly Ser Ser Pro Gly Phe Ala Ile Thr Ile
            590                 595                 600 att gct ctc tgc tgc ctt ccc tta gtg agt ctg ctt ctc tct gga gtg      2057
Ile Ala Leu Cys Cys Leu Pro Leu Val Ser Leu Leu Leu Ser Gly Val
            605                 610                 615 gtg gcc tat ttc cgg ggc cga gaa cac aag aag cta caa aag aaa ctc      2105
Val Ala Tyr Phe Arg Gly Arg Glu His Lys Lys Leu Gln Lys Lys Leu
            620                 625                 630 aaa gag agc gtg aag aag gaa gca gcc aaa gat gga gtg cca gcg atg      2153
Lys Glu Ser Val Lys Lys Glu Ala Ala Lys Asp Gly Val Pro Ala Met
635                 640                 645                 650 gag tgg cca ggc ccc aag gag agg agc agt ccc atc atc atc cag ctg      2201
Glu Trp Pro Gly Pro Lys Glu Arg Ser Ser Pro Ile Ile Ile Gln Leu
            655                 660                 665 ctg tca gac agg tgt ctg cag gtc ctg aac agg cat ctc act gtg ctc      2249
Leu Ser Asp Arg Cys Leu Gln Val Leu Asn Arg His Leu Thr Val Leu
            670                 675                 680 cgt gtg gtc cag ctg cag cct ctg cag cag gtc aac ctc atc ctg tcc      2297
Arg Val Val Gln Leu Gln Pro Leu Gln Gln Val Asn Leu Ile Leu Ser
            685                 690                 695 aac aac cga gga tgc cgc acc ctg ctg ctc aag atc cct aag gag tat      2345
Asn Asn Arg Gly Cys Arg Thr Leu Leu Leu Lys Ile Pro Lys Glu Tyr
700                 705                 710 gac ctg gtg ctg ctg ttt agt tct gaa gag gaa cgg ggc gcc ttt gtg      2393
Asp Leu Val Leu Leu Phe Ser Ser Glu Glu Glu Arg Gly Ala Phe Val
715                 720                 725                 730 cag cag cta tgg gac ttc tgc gtg cgc tgg gct ctg ggc ctc cat gtg      2441
Gln Gln Leu Trp Asp Phe Cys Val Arg Trp Ala Leu Gly Leu His Val
            735                 740                 745 gct gag atg agc gag aag gag cta ttt agg aag gct gtg aca aag cag      2489
Ala Glu Met Ser Glu Lys Glu Leu Phe Arg Lys Ala Val Thr Lys Gln
            750                 755                 760 cag cgg gaa cgc atc ctg gag atc ttc ttc aga cac ctt ttt gct cag      2537
Gln Arg Glu Arg Ile Leu Glu Ile Phe Phe Arg His Leu Phe Ala Gln
            765                 770                 775 gtg ctg gac atc aac cag gcc gac gca ggg acc ctg ccc ctg gac tcc      2585
Val Leu Asp Ile Asn Gln Ala Asp Ala Gly Thr Leu Pro Leu Asp Ser
780                 785                 790 tcc cag aag gtg cgg gag gcc ctg acc tgc gag ctg agc agg gcc gag      2633
Ser Gln Lys Val Arg Glu Ala Leu Thr Cys Glu Leu Ser Arg Ala Glu
795                 800                 805                 810 ttt gcc gag tcc ctg ggc ctc aag ccc cag gac atg ttt gtg gag tcc      2681
Phe Ala Glu Ser Leu Gly Leu Lys Pro Gln Asp Met Phe Val Glu Ser
            815                 820                 825 atg ttc tct ctg gct gac aag gat ggc aat ggc tac ctg tcc ttc cga      2729
Met Phe Ser Leu Ala Asp Lys Asp Gly Asn Gly Tyr Leu Ser Phe Arg
            830                 835                 840 gag ttc ctg gac atc ctg gtg gtc ttc atg aaa ggc tcc cca gag gat      2777
Glu Phe Leu Asp Ile Leu Val Val Phe Met Lys Gly Ser Pro Glu Asp
            845                 850                 855
```

-continued

| | | |
|---|---|---|
| aag tcc cgt cta atg ttt acc atg tat gac ctg gat gag aat ggc ttc<br>Lys Ser Arg Leu Met Phe Thr Met Tyr Asp Leu Asp Glu Asn Gly Phe<br>860                         865                     870 | 2825 |
| ctc tcc aag gac gaa ttc ttc acc atg atg cga tcc ttc atc gag atc<br>Leu Ser Lys Asp Glu Phe Phe Thr Met Met Arg Ser Phe Ile Glu Ile<br>875                         880                     885                  890 | 2873 |
| tcc aac aac tgc ctg tcc aag gcc cag ctg gcc gag gtg gtg gag tct<br>Ser Asn Asn Cys Leu Ser Lys Ala Gln Leu Ala Glu Val Val Glu Ser<br>                  895                     900                     905 | 2921 |
| atg ttc cgg gag tcg gga ttc cag gac aag gag gag ctg aca tgg gag<br>Met Phe Arg Glu Ser Gly Phe Gln Asp Lys Glu Glu Leu Thr Trp Glu<br>910                         915                     920 | 2969 |
| gat ttt cac ttc atg ctg cgg gac cat gac agc gag ctc cgc ttc acg<br>Asp Phe His Phe Met Leu Arg Asp His Asp Ser Glu Leu Arg Phe Thr<br>925                         930                     935 | 3017 |
| cag ctc tgt gtc aaa ggt gga ggt gga ggt gga aat ggt att aga gat<br>Gln Leu Cys Val Lys Gly Gly Gly Gly Gly Gly Asn Gly Ile Arg Asp<br>940                         945                     950 | 3065 |
| atc ttt aaa caa aac atc agc tgt cga gtc tcg ttc atc act cgg aca<br>Ile Phe Lys Gln Asn Ile Ser Cys Arg Val Ser Phe Ile Thr Arg Thr<br>955                         960                     965                  970 | 3113 |
| cct ggg gag cgc tcc cac ccc cag gga ctg ggg ccc cct gtc cca gaa<br>Pro Gly Glu Arg Ser His Pro Gln Gly Leu Gly Pro Pro Val Pro Glu<br>                  975                     980                     985 | 3161 |
| gcc cca gag ctg gga ggc cct gga ctg aag aag agg ttt ggc aaa aag<br>Ala Pro Glu Leu Gly Gly Pro Gly Leu Lys Lys Arg Phe Gly Lys Lys<br>                  990                     995                    1000 | 3209 |
| gca gca gtg ccc act ccc cgg ctg tac aca gag gcg ctg caa gag<br>Ala Ala Val Pro Thr Pro Arg Leu Tyr Thr Glu Ala Leu Gln Glu<br>          1005                     1010                     1015 | 3254 |
| aag atg cag cga ggc ttc cta gcc caa aag ctg cag cag tac aag<br>Lys Met Gln Arg Gly Phe Leu Ala Gln Lys Leu Gln Gln Tyr Lys<br>          1020                     1025                     1030 | 3299 |
| cgc ttc gtg gag aac tac cgg agg cac atc gtg tgt gtg gca atc<br>Arg Phe Val Glu Asn Tyr Arg Arg His Ile Val Cys Val Ala Ile<br>          1035                     1040                     1045 | 3344 |
| ttc tcg gcc atc tgt gtt ggc gtg ttt gca gat cgt gct tac tac<br>Phe Ser Ala Ile Cys Val Gly Val Phe Ala Asp Arg Ala Tyr Tyr<br>          1050                     1055                     1060 | 3389 |
| tat ggc ttt gcc ttg cca ccc tcg gac att gca cag acc acc ctc<br>Tyr Gly Phe Ala Leu Pro Pro Ser Asp Ile Ala Gln Thr Thr Leu<br>          1065                     1070                     1075 | 3434 |
| gtg ggc atc atc ctg tca cga ggc acg gcg gcc agc gtc tcc ttc<br>Val Gly Ile Ile Leu Ser Arg Gly Thr Ala Ala Ser Val Ser Phe<br>          1080                     1085                     1090 | 3479 |
| atg ttc tct tat atc ttg ctc acc atg tgc cgc aac ctc ata acc<br>Met Phe Ser Tyr Ile Leu Leu Thr Met Cys Arg Asn Leu Ile Thr<br>          1095                     1100                     1105 | 3524 |
| ttc ctg cga gag act ttc ctc aac cgc tat gtg cct ttt gat gcc<br>Phe Leu Arg Glu Thr Phe Leu Asn Arg Tyr Val Pro Phe Asp Ala<br>          1110                     1115                     1120 | 3569 |
| gca gtg gac ttc cac cgc tgg atc gcc atg gct gct gtt gtc ctg<br>Ala Val Asp Phe His Arg Trp Ile Ala Met Ala Ala Val Val Leu<br>          1125                     1130                     1135 | 3614 |
| gcc att ttg cac agt gct ggc cac gca gtc aat gtc tac atc ttc<br>Ala Ile Leu His Ser Ala Gly His Ala Val Asn Val Tyr Ile Phe<br>          1140                     1145                     1150 | 3659 |
| tca gtc agc cca ctc agc ctg ctg gcc tgc ata ttc ccc aac gtc<br>Ser Val Ser Pro Leu Ser Leu Leu Ala Cys Ile Phe Pro Asn Val<br>          1155                     1160                     1165 | 3704 |

-continued

| | |
|---|---|
| ttt gtg aat gat ggg tcc aag ctt ccc cag aag ttc tat tgg tgg<br>Phe Val Asn Asp Gly Ser Lys Leu Pro Gln Lys Phe Tyr Trp Trp<br>1170                          1175                         1180 | 3749 |
| ttc ttc cag acc gtc cca ggt atg aca ggt gtg ctt ctg ctc ctg<br>Phe Phe Gln Thr Val Pro Gly Met Thr Gly Val Leu Leu Leu Leu<br>1185                          1190                         1195 | 3794 |
| gtc ctg gcc atc atg tat gtc ttc gcc tcc cac cac ttc cgc cgc<br>Val Leu Ala Ile Met Tyr Val Phe Ala Ser His His Phe Arg Arg<br>1200                          1205                         1210 | 3839 |
| cgc agc ttc cgg ggc ttc tgg ctg acc cac cac ctc tac atc ctg<br>Arg Ser Phe Arg Gly Phe Trp Leu Thr His His Leu Tyr Ile Leu<br>1215                          1220                         1225 | 3884 |
| ctc tat gcc ctg ctc atc atc cat ggc agc tat gct ctg atc cag<br>Leu Tyr Ala Leu Leu Ile Ile His Gly Ser Tyr Ala Leu Ile Gln<br>1230                          1235                         1240 | 3929 |
| ctg ccc act ttc cac atc tac ttc ctg gtc ccg gca atc atc tat<br>Leu Pro Thr Phe His Ile Tyr Phe Leu Val Pro Ala Ile Ile Tyr<br>1245                          1250                         1255 | 3974 |
| gga ggt gac aag ctg gtg agc ctg agc cgg aag aag gtg gag atc<br>Gly Gly Asp Lys Leu Val Ser Leu Ser Arg Lys Lys Val Glu Ile<br>1260                          1265                         1270 | 4019 |
| agc gtg gtg aag gcg gag ctg ctg ccc tca gga gtg acc tac ctg<br>Ser Val Val Lys Ala Glu Leu Leu Pro Ser Gly Val Thr Tyr Leu<br>1275                          1280                         1285 | 4064 |
| caa ttc cag agg ccc caa ggc ttt gag tac aag tca gga cag tgg<br>Gln Phe Gln Arg Pro Gln Gly Phe Glu Tyr Lys Ser Gly Gln Trp<br>1290                          1295                         1300 | 4109 |
| gtg cgg atc gcc tgc ctg gct ctg ggg acc acc gag tac cac ccc<br>Val Arg Ile Ala Cys Leu Ala Leu Gly Thr Thr Glu Tyr His Pro<br>1305                          1310                         1315 | 4154 |
| ttc aca ctg acc tcc gcg ccc cat gag gac aca ctc agc ctg cac<br>Phe Thr Leu Thr Ser Ala Pro His Glu Asp Thr Leu Ser Leu His<br>1320                          1325                         1330 | 4199 |
| atc cgg gca gtg ggg ccc tgg acc act cgc ctc agg gag atc tac<br>Ile Arg Ala Val Gly Pro Trp Thr Thr Arg Leu Arg Glu Ile Tyr<br>1335                          1340                         1345 | 4244 |
| tca tcc cca aag ggc aat ggc tgt gct gga tac cca aag ctg tac<br>Ser Ser Pro Lys Gly Asn Gly Cys Ala Gly Tyr Pro Lys Leu Tyr<br>1350                          1355                         1360 | 4289 |
| ctt gat gga ccg ttt gga gag ggc cat cag gag tgg cat aaa ttt<br>Leu Asp Gly Pro Phe Gly Glu Gly His Gln Glu Trp His Lys Phe<br>1365                          1370                         1375 | 4334 |
| gag gtg tca gtg ttg gtg gga ggg ggc att ggg gtc acc ccc ttt<br>Glu Val Ser Val Leu Val Gly Gly Gly Ile Gly Val Thr Pro Phe<br>1380                          1385                         1390 | 4379 |
| gcc tcc atc ctc aaa gac ctg gtc ttc aag tca tcc ttg ggc agc<br>Ala Ser Ile Leu Lys Asp Leu Val Phe Lys Ser Ser Leu Gly Ser<br>1395                          1400                         1405 | 4424 |
| caa atg ctg tgt aag aag atc tac ttc atc tgg gtg aca cgg acc<br>Gln Met Leu Cys Lys Lys Ile Tyr Phe Ile Trp Val Thr Arg Thr<br>1410                          1415                         1420 | 4469 |
| cag cgt cag ttt gag tgg ctg gct gac atc atc caa gag gtg gag<br>Gln Arg Gln Phe Glu Trp Leu Ala Asp Ile Ile Gln Glu Val Glu<br>1425                          1430                         1435 | 4514 |
| gag aac gac cac cag gac ctg gtg tct gtg cac att tat gtc acc<br>Glu Asn Asp His Gln Asp Leu Val Ser Val His Ile Tyr Val Thr<br>1440                          1445                         1450 | 4559 |
| cag ctg gct gag aag ttc gac ctc agg acc acc atg cta tac atc<br>Gln Leu Ala Glu Lys Phe Asp Leu Arg Thr Thr Met Leu Tyr Ile | 4604 |

-continued

```
              1455                1460                1465
tgc gag cgg   cac ttc cag   aaa gtg ctg   aac cgg agt   ctg ttc acg        4649
Cys Glu Arg   His Phe Gln   Lys Val Leu   Asn Arg Ser   Leu Phe Thr
         1470                    1475                1480 ggc ctg cgc   tcc atc acc   cac ttt ggc   cgt ccc ccc   ttc gag ccc        4694
Gly Leu Arg   Ser Ile Thr   His Phe Gly   Arg Pro Pro   Phe Glu Pro
         1485                    1490                1495 ttc ttc aac   tcc ctg cag   gag gtc cac   cca cag gtg   cgc aag atc        4739
Phe Phe Asn   Ser Leu Gln   Glu Val His   Pro Gln Val   Arg Lys Ile
         1500                    1505                1510 ggg gtg ttc   agc tgc ggc   cct cca gga   atg acc aag   aat gta gag        4784
Gly Val Phe   Ser Cys Gly   Pro Pro Gly   Met Thr Lys   Asn Val Glu
         1515                    1520                1525 aag gcc tgt   cag ctc gtc   aac agg cag   gac cga gcc   cac ttc atg        4829
Lys Ala Cys   Gln Leu Val   Asn Arg Gln   Asp Arg Ala   His Phe Met
         1530                    1535                1540 cac cac tat   gag aac ttc tga gcctgtcctc cctggctgct gcttccagta             4880
His His Tyr   Glu Asn Phe
         1545 tcctgccttc tcttctgtgc acctaagttg cccagccctg ctggcaatct ctccatcaga         4940
atccacctta ggcctcagct ggagggctgc agagcccctc ccaatattgg gagaatattg         5000
acccagacaa ttatacaaat gagaaaaggc aggagactat gttctacaat gcagtgcat          5060
gatgattata agtccacctg tttatcaacg gcaccattcc tgcagccctc cagacttcct         5120
gcccttagca agtgcgcaac cagtcaggat ctcccaaaga agataaagac cactcctcac         5180
cccagctcaa gccatggcag gcgtggcaag caaagtgggg aggagacagt ccctgcttgt         5240
gacaagtgtg gaggtgaaaa ggtcaatagt gcttgtctcc gatagctccc cacatctcta         5300
attgacttcc acaaaatcga tgcgttgctt tggtatttgc ttggactgac atttgaggga         5360
ggaggaggct gggatcctct ggctgagaat ctcctcagag cccagtgcag aagctgtgat         5420
gcttagaacc tggacagccc gactgcctca actctgtctc caggtctatt ccctccagct         5480
ccaaaaggag cagccctact tctacccctt cccgtcccca agtgtcagc aactttgagg          5540
agggcaccag gaaacaaaga tgccttccca gccctgatat tcttgatgtc accagtgata         5600
cccactgccc tgacccctgg gcaggcccct tctgcatct actggagtgg tccctgggct          5660
cttggggctg aaggattcca gcctctctgc cagatattca gtactcgatc tcaattcccc         5720
tcttccacaa gagttgggtg accagctgtc ctagtttgcc caggactctc cctgttttag         5780
cactgaaagt ctcttgcccc aggaaacccc atcagtccca ggcagattgg gacagctggt         5840
caccttacgc aagagccagg ctgaaacatc ccctccatac tcagctcttt aacttttctt         5900
ttccttttc atcgggctct ttcctaaaaa gctgagctgt aaaatatttt acatcgaggt          5960
ataataaata atcatgtaca tgttttacca ccacccaggt caagacatag aatgtttcaa         6020
catttccatc accccagaaa ctccccttgt acccccttcc cttcgtctcc cctagctcct         6080
agaagcaacc actgatgtga tttctaccaa atccagtttt ggtcctacta aatatactct         6140
tttgagactg gcctcttta ctcaccataa tgcctttgta attcatccat gctgttgtgt          6200
gtatcagcag tttgttcctt ttcattgctg agtagtattc tattgtagag atgtaccaca         6260
gtttgtttat tcttctgttg atggacgttt gggttgtttc taattttgaa tgattataaa         6320
taaaaattct gtgagtgttc ttgtaaaaaa aaaaaaaaaa aaaaaaaaa aaaaa               6375
```

<210> SEQ ID NO 2
<211> LENGTH: 1548

-continued

```
<212> TYPE: PRT
<213> ORGANISM: Homo sapiens

<400> SEQUENCE: 2

Met Leu Arg Ala Arg Pro Glu Ala Leu Met Leu Leu Gly Ala Leu Leu
1               5                   10                  15

Thr Gly Ser Leu Gly Pro Ser Gly Ser Gln Asp Ala Leu Ser Leu Pro
            20                  25                  30

Trp Glu Val Gln Arg Tyr Asp Gly Trp Phe Asn Asn Leu Arg His His
        35                  40                  45

Glu Arg Gly Ala Val Gly Cys Arg Leu Gln Arg Val Pro Ala Asn
    50                  55                  60

Tyr Ala Asp Gly Val Tyr Gln Ala Leu Glu Glu Pro Gln Leu Pro Asn
65                  70                  75                  80

Pro Arg Arg Leu Ser Asn Ala Ala Thr Arg Gly Ile Ala Gly Leu Pro
                85                  90                  95

Ser Leu His Asn Arg Thr Val Leu Gly Val Phe Phe Gly Tyr His Val
            100                 105                 110

Leu Ser Asp Val Val Ser Val Glu Thr Pro Gly Cys Pro Ala Glu Phe
        115                 120                 125

Leu Asn Ile Arg Ile Pro Pro Gly Asp Leu Val Phe Asp Pro Asp Gln
130                 135                 140

Arg Gly Asp Val Val Leu Pro Phe Gln Arg Ser Arg Trp Asp Pro Glu
145                 150                 155                 160

Thr Gly Arg Ser Pro Ser Asn Pro Arg Asp Leu Ala Asn Gln Val Thr
                165                 170                 175

Gly Trp Leu Asp Gly Ser Ala Ile Tyr Gly Ser Ser His Ser Trp Ser
            180                 185                 190

Asp Ala Leu Arg Ser Phe Ser Gly Gly Gln Leu Ala Ser Gly Pro Asp
        195                 200                 205

Pro Ala Phe Pro Arg Asp Ser Gln Asn Pro Leu Leu Met Trp Ala Ala
210                 215                 220

Pro Asp Pro Ala Thr Gly Gln Asn Gly Pro Arg Gly Leu Tyr Ala Phe
225                 230                 235                 240

Gly Ala Glu Arg Gly Asn Arg Glu Pro Phe Leu Gln Ala Leu Gly Leu
                245                 250                 255

Leu Trp Phe Arg Tyr His Asn Leu Trp Ala Gln Arg Leu Ala Arg Gln
            260                 265                 270

His Pro Asp Trp Glu Asp Glu Leu Phe Gln His Ala Arg Lys Arg
        275                 280                 285

Val Ile Ala Thr Tyr Gln Asn Ile Ala Val Tyr Glu Trp Leu Pro Ser
290                 295                 300

Phe Leu Gln Lys Thr Leu Pro Glu Tyr Thr Gly Tyr Arg Pro Phe Leu
305                 310                 315                 320

Asp Pro Ser Ile Ser Pro Glu Phe Val Val Ala Ser Glu Gln Phe Phe
                325                 330                 335

Ser Thr Met Val Pro Gly Val Tyr Met Arg Asn Ala Ser Cys His
            340                 345                 350

Phe Arg Lys Val Leu Asn Lys Gly Phe Gln Ser Ser Gln Ala Leu Arg
        355                 360                 365

Val Cys Asn Asn Tyr Trp Ile Arg Glu Asn Pro Asn Leu Asn Ser Thr
370                 375                 380

Gln Glu Val Asn Glu Leu Leu Leu Gly Met Ala Ser Gln Ile Ser Glu
385                 390                 395                 400
```

-continued

```
Leu Glu Asp Asn Ile Val Val Glu Asp Leu Arg Asp Tyr Trp Pro Gly
                405                 410                 415

Pro Gly Lys Phe Ser Arg Thr Asp Tyr Val Ala Ser Ser Ile Gln Arg
            420                 425                 430

Gly Arg Asp Met Gly Leu Pro Ser Tyr Ser Gln Ala Leu Leu Ala Phe
        435                 440                 445

Gly Leu Asp Ile Pro Arg Asn Trp Ser Asp Leu Asn Pro Asn Val Asp
    450                 455                 460

Pro Gln Val Leu Glu Ala Thr Ala Leu Tyr Asn Gln Asp Leu Ser
465                 470                 475                 480

Gln Leu Glu Leu Leu Leu Gly Gly Leu Leu Glu Ser His Gly Asp Pro
            485                 490                 495

Gly Pro Leu Phe Ser Ala Ile Val Leu Asp Gln Phe Val Arg Leu Arg
        500                 505                 510

Asp Gly Asp Arg Tyr Trp Phe Glu Asn Thr Arg Asn Gly Leu Phe Ser
    515                 520                 525

Lys Lys Glu Ile Glu Asp Ile Arg Asn Thr Thr Leu Arg Asp Val Leu
530                 535                 540

Val Ala Val Ile Asn Ile Asp Pro Ser Ala Leu Gln Pro Asn Val Phe
545                 550                 555                 560

Val Trp His Lys Gly Ala Pro Cys Pro Gln Pro Lys Gln Leu Thr Thr
            565                 570                 575

Asp Gly Leu Pro Gln Cys Ala Pro Leu Thr Val Leu Asp Phe Phe Glu
        580                 585                 590

Gly Ser Ser Pro Gly Phe Ala Ile Thr Ile Ala Leu Cys Cys Leu
    595                 600                 605

Pro Leu Val Ser Leu Leu Ser Gly Val Val Ala Tyr Phe Arg Gly
    610                 615                 620

Arg Glu His Lys Lys Leu Gln Lys Lys Leu Lys Glu Ser Val Lys Lys
625                 630                 635                 640

Glu Ala Ala Lys Asp Gly Val Pro Ala Met Glu Trp Pro Gly Pro Lys
            645                 650                 655

Glu Arg Ser Ser Pro Ile Ile Ile Gln Leu Leu Ser Asp Arg Cys Leu
        660                 665                 670

Gln Val Leu Asn Arg His Leu Thr Val Leu Arg Val Val Gln Leu Gln
    675                 680                 685

Pro Leu Gln Gln Val Asn Leu Ile Leu Ser Asn Asn Arg Gly Cys Arg
    690                 695                 700

Thr Leu Leu Leu Lys Ile Pro Lys Glu Tyr Asp Leu Val Leu Leu Phe
705                 710                 715                 720

Ser Ser Glu Glu Glu Arg Gly Ala Phe Val Gln Leu Trp Asp Phe
            725                 730                 735

Cys Val Arg Trp Ala Leu Gly Leu His Val Ala Glu Met Ser Glu Lys
            740                 745                 750

Glu Leu Phe Arg Lys Ala Val Thr Lys Gln Gln Arg Glu Arg Ile Leu
        755                 760                 765

Glu Ile Phe Phe Arg His Leu Phe Ala Gln Val Leu Asp Ile Asn Gln
    770                 775                 780

Ala Asp Ala Gly Thr Leu Pro Leu Asp Ser Gln Lys Val Arg Glu
785                 790                 795                 800

Ala Leu Thr Cys Glu Leu Ser Arg Ala Glu Phe Ala Glu Ser Leu Gly
            805                 810                 815
```

```
Leu Lys Pro Gln Asp Met Phe Val Glu Ser Met Phe Ser Leu Ala Asp
        820                 825                 830

Lys Asp Gly Asn Gly Tyr Leu Ser Phe Arg Glu Phe Leu Asp Ile Leu
        835                 840                 845

Val Val Phe Met Lys Gly Ser Pro Glu Asp Lys Ser Arg Leu Met Phe
    850                 855                 860

Thr Met Tyr Asp Leu Asp Glu Asn Gly Phe Leu Ser Lys Asp Glu Phe
865             870                 875                 880

Phe Thr Met Met Arg Ser Phe Ile Glu Ile Ser Asn Asn Cys Leu Ser
                885                 890                 895

Lys Ala Gln Leu Ala Glu Val Glu Ser Met Phe Arg Glu Ser Gly
            900                 905                 910

Phe Gln Asp Lys Glu Glu Leu Thr Trp Glu Asp Phe His Phe Met Leu
            915                 920                 925

Arg Asp His Asp Ser Glu Leu Arg Phe Thr Gln Leu Cys Val Lys Gly
    930                 935                 940

Gly Gly Gly Gly Gly Asn Gly Ile Arg Asp Ile Phe Lys Gln Asn Ile
945                 950                 955                 960

Ser Cys Arg Val Ser Phe Ile Thr Arg Thr Pro Gly Glu Arg Ser His
                965                 970                 975

Pro Gln Gly Leu Gly Pro Pro Val Pro Glu Ala Pro Glu Leu Gly Gly
            980                 985                 990

Pro Gly Leu Lys Lys Arg Phe Gly Lys Lys Ala Ala Val Pro Thr Pro
            995                 1000                1005

Arg Leu Tyr Thr Glu Ala Leu Gln Glu Lys Met Gln Arg Gly Phe
    1010                1015                1020

Leu Ala Gln Lys Leu Gln Gln Tyr Lys Arg Phe Val Glu Asn Tyr
    1025                1030                1035

Arg Arg His Ile Val Cys Val Ala Ile Phe Ser Ala Ile Cys Val
    1040                1045                1050

Gly Val Phe Ala Asp Arg Ala Tyr Tyr Tyr Gly Phe Ala Leu Pro
    1055                1060                1065

Pro Ser Asp Ile Ala Gln Thr Thr Leu Val Gly Ile Ile Leu Ser
    1070                1075                1080

Arg Gly Thr Ala Ala Ser Val Ser Phe Met Phe Ser Tyr Ile Leu
    1085                1090                1095

Leu Thr Met Cys Arg Asn Leu Ile Thr Phe Leu Arg Glu Thr Phe
    1100                1105                1110

Leu Asn Arg Tyr Val Pro Phe Asp Ala Ala Val Asp Phe His Arg
    1115                1120                1125

Trp Ile Ala Met Ala Ala Val Val Leu Ala Ile Leu His Ser Ala
    1130                1135                1140

Gly His Ala Val Asn Val Tyr Ile Phe Ser Val Ser Pro Leu Ser
    1145                1150                1155

Leu Leu Ala Cys Ile Phe Pro Asn Val Phe Val Asn Asp Gly Ser
    1160                1165                1170

Lys Leu Pro Gln Lys Phe Tyr Trp Trp Phe Phe Gln Thr Val Pro
    1175                1180                1185

Gly Met Thr Gly Val Leu Leu Leu Leu Val Leu Ala Ile Met Tyr
    1190                1195                1200

Val Phe Ala Ser His His Phe Arg Arg Arg Ser Phe Arg Gly Phe
    1205                1210                1215

Trp Leu Thr His His Leu Tyr Ile Leu Leu Tyr Ala Leu Leu Ile
```

| | | | | | | | | | |
|---|---|---|---|---|---|---|---|---|---|
| | | 1220 | | | 1225 | | | 1230 | |

Ile His Gly Ser Tyr Ala Leu Ile Gln Leu Pro Thr Phe His Ile
1235                    1240                    1245

Tyr Phe Leu Val Pro Ala Ile Ile Tyr Gly Gly Asp Lys Leu Val
1250                    1255                    1260

Ser Leu Ser Arg Lys Lys Val Glu Ile Ser Val Val Lys Ala Glu
1265                    1270                    1275

Leu Leu Pro Ser Gly Val Thr Tyr Leu Gln Phe Gln Arg Pro Gln
1280                    1285                    1290

Gly Phe Glu Tyr Lys Ser Gly Gln Trp Val Arg Ile Ala Cys Leu
1295                    1300                    1305

Ala Leu Gly Thr Thr Glu Tyr His Pro Phe Thr Leu Thr Ser Ala
1310                    1315                    1320

Pro His Glu Asp Thr Leu Ser Leu His Ile Arg Ala Val Gly Pro
1325                    1330                    1335

Trp Thr Thr Arg Leu Arg Glu Ile Tyr Ser Ser Pro Lys Gly Asn
1340                    1345                    1350

Gly Cys Ala Gly Tyr Pro Lys Leu Tyr Leu Asp Gly Pro Phe Gly
1355                    1360                    1365

Glu Gly His Gln Glu Trp His Lys Phe Glu Val Ser Val Leu Val
1370                    1375                    1380

Gly Gly Gly Ile Gly Val Thr Pro Phe Ala Ser Ile Leu Lys Asp
1385                    1390                    1395

Leu Val Phe Lys Ser Ser Leu Gly Ser Gln Met Leu Cys Lys Lys
1400                    1405                    1410

Ile Tyr Phe Ile Trp Val Thr Arg Thr Gln Arg Gln Phe Glu Trp
1415                    1420                    1425

Leu Ala Asp Ile Ile Gln Glu Val Glu Asn Asp His Gln Asp
1430                    1435                    1440

Leu Val Ser Val His Ile Tyr Val Thr Gln Leu Ala Glu Lys Phe
1445                    1450                    1455

Asp Leu Arg Thr Thr Met Leu Tyr Ile Cys Glu Arg His Phe Gln
1460                    1465                    1470

Lys Val Leu Asn Arg Ser Leu Phe Thr Gly Leu Arg Ser Ile Thr
1475                    1480                    1485

His Phe Gly Arg Pro Pro Phe Glu Pro Phe Asn Ser Leu Gln
1490                    1495                    1500

Glu Val His Pro Gln Val Arg Lys Ile Gly Val Phe Ser Cys Gly
1505                    1510                    1515

Pro Pro Gly Met Thr Lys Asn Val Glu Lys Ala Cys Gln Leu Val
1520                    1525                    1530

Asn Arg Gln Asp Arg Ala His Phe Met His His Tyr Glu Asn Phe
1535                    1540                    1545

<210> SEQ ID NO 3
<211> LENGTH: 4494
<212> TYPE: DNA
<213> ORGANISM: Caenorhabditis elegans
<220> FEATURE:
<221> NAME/KEY: CDS
<222> LOCATION: (1)..(4494)

<400> SEQUENCE: 3 atg cgc tca aaa cat gtg ctg tac ata gct ata ctg ttc agt tca att    48
Met Arg Ser Lys His Val Leu Tyr Ile Ala Ile Leu Phe Ser Ser Ile
1               5                   10                  15

-continued

| | |
|---|---|
| ttt gga ggg aaa gga atc caa caa aat gag gaa ttt caa aga tac gac<br>Phe Gly Gly Lys Gly Ile Gln Gln Asn Glu Glu Phe Gln Arg Tyr Asp<br>20            25              30 | 96 |
| gga tgg tac aac aat ctg gcg aat agt gaa tgg ggt tct gct gga agt<br>Gly Trp Tyr Asn Asn Leu Ala Asn Ser Glu Trp Gly Ser Ala Gly Ser<br>35              40              45 | 144 |
| cgg ctg cat aga gat gca cgt tcc tac tac tca gac ggt gta tat tca<br>Arg Leu His Arg Asp Ala Arg Ser Tyr Tyr Ser Asp Gly Val Tyr Ser<br>50              55              60 | 192 |
| gtg aat aac tca ctt ccg tcc gcc cgt gaa ctc tcc gat ata cta ttc<br>Val Asn Asn Ser Leu Pro Ser Ala Arg Glu Leu Ser Asp Ile Leu Phe<br>65              70              75              80 | 240 |
| aaa gga gag tcc ggt ata cct aat aca aga gga tgc acg act tta ttg<br>Lys Gly Glu Ser Gly Ile Pro Asn Thr Arg Gly Cys Thr Thr Leu Leu<br>85              90              95 | 288 |
| gca ttt ttc agt caa gta gtt gct cat gaa ata atg caa tca aat gga<br>Ala Phe Phe Ser Gln Val Val Ala His Glu Ile Met Gln Ser Asn Gly<br>100             105             110 | 336 |
| gta tcc tgt cca cta gag aca ctt aaa att caa gta ccc cta tgt gat<br>Val Ser Cys Pro Leu Glu Thr Leu Lys Ile Gln Val Pro Leu Cys Asp<br>115             120             125 | 384 |
| aat gta ttt gat aaa gaa tgt gag gga aag aca gaa atc cca ttt aca<br>Asn Val Phe Asp Lys Glu Cys Glu Gly Lys Thr Glu Ile Pro Phe Thr<br>130             135             140 | 432 |
| cgt gcc aaa tac gat aaa gca act gga aat ggg ctc aac tca cct cga<br>Arg Ala Lys Tyr Asp Lys Ala Thr Gly Asn Gly Leu Asn Ser Pro Arg<br>145             150             155             160 | 480 |
| gaa caa atc aat gaa cgg act tca tgg att gat gga tca ttc atc tat<br>Glu Gln Ile Asn Glu Arg Thr Ser Trp Ile Asp Gly Ser Phe Ile Tyr<br>165             170             175 | 528 |
| ggt acc acc cag cca tgg gtg tcc tca tta aga tct ttc aaa caa ggg<br>Gly Thr Thr Gln Pro Trp Val Ser Ser Leu Arg Ser Phe Lys Gln Gly<br>180             185             190 | 576 |
| cgg ttg gct gaa ggt gta cct gga tat cca cca ctt aac aac cca cat<br>Arg Leu Ala Glu Gly Val Pro Gly Tyr Pro Pro Leu Asn Asn Pro His<br>195             200             205 | 624 |
| att cca ttg aat aac ccc gct ccg cca caa gta cat cga ttg atg agt<br>Ile Pro Leu Asn Asn Pro Ala Pro Pro Gln Val His Arg Leu Met Ser<br>210             215             220 | 672 |
| cca gat aga tta ttt atg ttg gga gac tcg cgt gtg aat gag aat cca<br>Pro Asp Arg Leu Phe Met Leu Gly Asp Ser Arg Val Asn Glu Asn Pro<br>225             230             235             240 | 720 |
| ggt ctt ctc tca ttt ggt ctg atc ctc ttc cgt tgg cat aac tac aat<br>Gly Leu Leu Ser Phe Gly Leu Ile Leu Phe Arg Trp His Asn Tyr Asn<br>245             250             255 | 768 |
| gca aat caa atc cat cga gaa cat cct gac tgg aca gac gaa caa atc<br>Ala Asn Gln Ile His Arg Glu His Pro Asp Trp Thr Asp Glu Gln Ile<br>260             265             270 | 816 |
| ttc cag gca gca cgt cgt ttg gtg att gca tct atg cag aag att att<br>Phe Gln Ala Ala Arg Arg Leu Val Ile Ala Ser Met Gln Lys Ile Ile<br>275             280             285 | 864 |
| gca tat gac ttt gtt cca ggg ctg tta ggt gaa gac gtt cgt ttg tca<br>Ala Tyr Asp Phe Val Pro Gly Leu Leu Gly Glu Asp Val Arg Leu Ser<br>290             295             300 | 912 |
| aac tac acc aaa tac atg cca cat gtt cca cct gga atc tcg cat gct<br>Asn Tyr Thr Lys Tyr Met Pro His Val Pro Pro Gly Ile Ser His Ala<br>305             310             315             320 | 960 |
| ttt gga gca gcc gcc ttc agg ttc cct cac tca att gtg cca cca gca<br>Phe Gly Ala Ala Ala Phe Arg Phe Pro His Ser Ile Val Pro Pro Ala | 1008 |

-continued

```
                       325                 330                 335
atg ctt ctg aga aaa cga gga aat aaa tgt gaa ttc cgg acg gaa gtt      1056
Met Leu Leu Arg Lys Arg Gly Asn Lys Cys Glu Phe Arg Thr Glu Val
            340                 345                 350 ggt gga tat cct gca ttg aga ttg tgc cag aat tgg tgg aat gcg cag      1104
Gly Gly Tyr Pro Ala Leu Arg Leu Cys Gln Asn Trp Trp Asn Ala Gln
        355                 360                 365 gat att gta aag gag tac agt gtg gat gag att att ctt gga atg gca      1152
Asp Ile Val Lys Glu Tyr Ser Val Asp Glu Ile Ile Leu Gly Met Ala
    370                 375                 380 agc cag ata gct gaa cga gat gat aac ata gta gtt gaa gat ctt cgt      1200
Ser Gln Ile Ala Glu Arg Asp Asp Asn Ile Val Val Glu Asp Leu Arg
385                 390                 395                 400 gat tac atc ttc gga cca atg cat ttc tct cgt ttg gat gtt gtt gct      1248
Asp Tyr Ile Phe Gly Pro Met His Phe Ser Arg Leu Asp Val Val Ala
                405                 410                 415 tca tca ata atg aga gga agg gac aat gga gta cca ccg tat aat gaa      1296
Ser Ser Ile Met Arg Gly Arg Asp Asn Gly Val Pro Pro Tyr Asn Glu
            420                 425                 430 ttg aga aga aca ttc gga ctt gcg cca aag aca tgg gag aca atg aat      1344
Leu Arg Arg Thr Phe Gly Leu Ala Pro Lys Thr Trp Glu Thr Met Asn
        435                 440                 445 gaa gac ttt tac aag aag cat act gca aag gtg gag aag ttg aaa gag      1392
Glu Asp Phe Tyr Lys Lys His Thr Ala Lys Val Glu Lys Leu Lys Glu
    450                 455                 460 ttg tat gga ggc aat att tta tat ttg gat gct tat gta gga gga atg      1440
Leu Tyr Gly Gly Asn Ile Leu Tyr Leu Asp Ala Tyr Val Gly Gly Met
465                 470                 475                 480 ctg gaa gga ggt gaa aat ggg cct gga gag ttg ttc aaa gaa atc ata      1488
Leu Glu Gly Gly Glu Asn Gly Pro Gly Glu Leu Phe Lys Glu Ile Ile
                485                 490                 495 aag gat caa ttc acc cgt att cgt gat gga gat aga ttc tgg ttt gag      1536
Lys Asp Gln Phe Thr Arg Ile Arg Asp Gly Asp Arg Phe Trp Phe Glu
            500                 505                 510 aat aaa ttg aat gga tta ttc act gat gaa gaa gtt caa atg att cat      1584
Asn Lys Leu Asn Gly Leu Phe Thr Asp Glu Glu Val Gln Met Ile His
        515                 520                 525 agt att aca ctt cga gat att atc aaa gca acc acc gat atc gat gag      1632
Ser Ile Thr Leu Arg Asp Ile Ile Lys Ala Thr Thr Asp Ile Asp Glu
    530                 535                 540 aca atg ctt cag aag gat gta ttc ttc ttc aag gaa ggt gac ccg tgc      1680
Thr Met Leu Gln Lys Asp Val Phe Phe Phe Lys Glu Gly Asp Pro Cys
545                 550                 555                 560 ccg caa cca ttc caa gtg aac aca act gga ctt gaa cca tgt gtt cca      1728
Pro Gln Pro Phe Gln Val Asn Thr Thr Gly Leu Glu Pro Cys Val Pro
                565                 570                 575 ttt atg caa tca act tat tgg act gat aat gac acc act tat gtt ttc      1776
Phe Met Gln Ser Thr Tyr Trp Thr Asp Asn Asp Thr Thr Tyr Val Phe
            580                 585                 590 acc cta att gga tta gca tgt gtg cca tta att tgc tat gga att ggc      1824
Thr Leu Ile Gly Leu Ala Cys Val Pro Leu Ile Cys Tyr Gly Ile Gly
        595                 600                 605 cga tac ttg gtt aat cgt cgc att gct att ggc cac aac agt gct tgt      1872
Arg Tyr Leu Val Asn Arg Arg Ile Ala Ile Gly His Asn Ser Ala Cys
    610                 615                 620 gac agc cta act act gac ttt gca aat gat gat tgt ggc gcg aag gga      1920
Asp Ser Leu Thr Thr Asp Phe Ala Asn Asp Asp Cys Gly Ala Lys Gly
625                 630                 635                 640 gat att tat ggt gta aat gct ttg gaa tgg ctt caa gaa gag tac ata      1968
```

```
                                      -continued

Asp Ile Tyr Gly Val Asn Ala Leu Glu Trp Leu Gln Glu Tyr Ile
            645                 650                 655 cga cag gtc agg ata gaa ata gaa aac acc acg ttg gca gta aag aag    2016
Arg Gln Val Arg Ile Glu Ile Glu Asn Thr Thr Leu Ala Val Lys Lys
            660                 665                 670 cca cgc ggt gga atc ctt cga aaa att cgt ttt gaa act gga cag aag    2064
Pro Arg Gly Gly Ile Leu Arg Lys Ile Arg Phe Glu Thr Gly Gln Lys
            675                 680                 685 att gag tta ttc cac tct atg ccg aat cca tca gca atg cac gga cca    2112
Ile Glu Leu Phe His Ser Met Pro Asn Pro Ser Ala Met His Gly Pro
        690                 695                 700 ttt gta ctt ctg tct caa aag aat aat cat cat ttg gtg ata aga ttg    2160
Phe Val Leu Leu Ser Gln Lys Asn Asn His His Leu Val Ile Arg Leu
705                 710                 715                 720 tcg tct gat aga gat tta tct aaa ttt ttg gat caa att aga cag gcg    2208
Ser Ser Asp Arg Asp Leu Ser Lys Phe Leu Asp Gln Ile Arg Gln Ala
                725                 730                 735 gct agt gga atc aat gca gag gtt atc ata aag gat gag gag aat tct    2256
Ala Ser Gly Ile Asn Ala Glu Val Ile Ile Lys Asp Glu Glu Asn Ser
            740                 745                 750 att ctc tta tcc caa gca atc aca aaa gaa cgc cgt caa gac cga ctg    2304
Ile Leu Leu Ser Gln Ala Ile Thr Lys Glu Arg Arg Gln Asp Arg Leu
            755                 760                 765 gac ctg ttc ttc cgt gaa gcc tac gca aaa gca ttc aat gat agt gaa    2352
Asp Leu Phe Phe Arg Glu Ala Tyr Ala Lys Ala Phe Asn Asp Ser Glu
            770                 775                 780 ctt caa gat tcg gaa act tca ttt gac tca tca aat gat gat ata tta    2400
Leu Gln Asp Ser Glu Thr Ser Phe Asp Ser Ser Asn Asp Asp Ile Leu
785                 790                 795                 800 aat gag aca ata tct cgt gag gaa ctg gca agt gca atg gga atg aaa    2448
Asn Glu Thr Ile Ser Arg Glu Glu Leu Ala Ser Ala Met Gly Met Lys
                805                 810                 815 gcg aat aat gag ttt gtg aag aga atg ttc gcg atg att gca aaa cat    2496
Ala Asn Asn Glu Phe Val Lys Arg Met Phe Ala Met Ile Ala Lys His
            820                 825                 830 aat gag gat tcg ctc agt ttc aat gag ttt ttg aca gtc ttg aga gag    2544
Asn Glu Asp Ser Leu Ser Phe Asn Glu Phe Leu Thr Val Leu Arg Glu
            835                 840                 845 ttt gtt aat gct cct caa aag caa aaa ctg caa act cta ttc aaa atg    2592
Phe Val Asn Ala Pro Gln Lys Gln Lys Leu Gln Thr Leu Phe Lys Met
850                 855                 860 tgt gat ttg gag gga aag aac aag gta ctc cga aag gat ctc gcg gaa    2640
Cys Asp Leu Glu Gly Lys Asn Lys Val Leu Arg Lys Asp Leu Ala Glu
865                 870                 875                 880 ctc gtc aag tcc ctc aat caa acc gct gga gtt cac att act gaa agt    2688
Leu Val Lys Ser Leu Asn Gln Thr Ala Gly Val His Ile Thr Glu Ser
                885                 890                 895 gtg cag ctt cga tta ttc aat gaa gtg ttg cac tat gca gga gtg agc    2736
Val Gln Leu Arg Leu Phe Asn Glu Val Leu His Tyr Ala Gly Val Ser
            900                 905                 910 aat gat gcc aag tac ctg act tac gac gat ttc aat gct ctg ttc tcg    2784
Asn Asp Ala Lys Tyr Leu Thr Tyr Asp Asp Phe Asn Ala Leu Phe Ser
            915                 920                 925 gat ata cct gac aag caa cca gtt gga ctg ccg ttc aat cga aag aac    2832
Asp Ile Pro Asp Lys Gln Pro Val Gly Leu Pro Phe Asn Arg Lys Asn
        930                 935                 940 tat cag cca agt att gga gaa aca tct tct ctg aac tca ttt gcc gtc    2880
Tyr Gln Pro Ser Ile Gly Glu Thr Ser Ser Leu Asn Ser Phe Ala Val
945                 950                 955                 960
```

-continued

| | |
|---|---|
| gtg gat cga tcc atc aac agt tca gca ccg cta act ttg atc cac aaa<br>Val Asp Arg Ser Ile Asn Ser Ser Ala Pro Leu Thr Leu Ile His Lys<br>              965                      970                   975 | 2928 |
| gtt tca gcg ttc ttg gag acc tat cgc caa cac gtt ttc att gtc ttc<br>Val Ser Ala Phe Leu Glu Thr Tyr Arg Gln His Val Phe Ile Val Phe<br>              980                      985                   990 | 2976 |
| tgc ttt gtt gcc atc aat ctt gtt ctt ttc ttc gaa cgg ttt tgg cat<br>Cys Phe Val Ala Ile Asn Leu Val Leu Phe Phe Glu Arg Phe Trp His<br>              995                    1000                 1005 | 3024 |
| tat cgt tac atg gcg gaa aac agg gat ctc cga cga gta atg gga<br>Tyr Arg Tyr Met Ala Glu Asn Arg Asp Leu Arg Arg Val Met Gly<br>        1010                  1015                  1020 | 3069 |
| gct gga atc gct att act cgt ggt gcc gcg gga gcc ttg tca ttt<br>Ala Gly Ile Ala Ile Thr Arg Gly Ala Ala Gly Ala Leu Ser Phe<br>        1025                  1030                  1035 | 3114 |
| tgc atg gcg ttg ata ttg ctg aca gtt tgt aga aac ata atc aca<br>Cys Met Ala Leu Ile Leu Leu Thr Val Cys Arg Asn Ile Ile Thr<br>        1040                  1045                  1050 | 3159 |
| ctt ctt cga gag aca gtc att gcg cag tat att cca ttt gac tcg<br>Leu Leu Arg Glu Thr Val Ile Ala Gln Tyr Ile Pro Phe Asp Ser<br>        1055                  1060                  1065 | 3204 |
| gct att gcg ttc cac aag atc gtt gcg ctc ttt gcg gct ttc tgg<br>Ala Ile Ala Phe His Lys Ile Val Ala Leu Phe Ala Ala Phe Trp<br>        1070                  1075                  1080 | 3249 |
| gcc act ctt cac acc gtt gga cat tgt gtc aat ttc tat cac gtt<br>Ala Thr Leu His Thr Val Gly His Cys Val Asn Phe Tyr His Val<br>        1085                  1090                  1095 | 3294 |
| gga act caa agt caa gaa ggt ctt gct tgt ctc ttt cag gaa gca<br>Gly Thr Gln Ser Gln Glu Gly Leu Ala Cys Leu Phe Gln Glu Ala<br>        1100                  1105                  1110 | 3339 |
| ttc ttt gga tcc aac ttc ctt cct tca atc agt tac tgg ttc ttc<br>Phe Phe Gly Ser Asn Phe Leu Pro Ser Ile Ser Tyr Trp Phe Phe<br>        1115                  1120                  1125 | 3384 |
| agc aca att aca ggt ctg aca gga att gca ttg gtc gct gtc atg<br>Ser Thr Ile Thr Gly Leu Thr Gly Ile Ala Leu Val Ala Val Met<br>        1130                  1135                  1140 | 3429 |
| tgc atc att tat gtt ttc gcg tta cca tgt ttc att aag aga gct<br>Cys Ile Ile Tyr Val Phe Ala Leu Pro Cys Phe Ile Lys Arg Ala<br>        1145                  1150                  1155 | 3474 |
| tat cac gca ttc cgg ctc aca cat ctt ctc aat att gcc ttt tac<br>Tyr His Ala Phe Arg Leu Thr His Leu Leu Asn Ile Ala Phe Tyr<br>        1160                  1165                  1170 | 3519 |
| gca ctt act ctt ctt cat ggg ctt cca aag ttg ttg gat tct ccc<br>Ala Leu Thr Leu Leu His Gly Leu Pro Lys Leu Leu Asp Ser Pro<br>        1175                  1180                  1185 | 3564 |
| aaa ttt ggc tac tac gtt gtt ggt ccc atc gtg tta ttt gta att<br>Lys Phe Gly Tyr Tyr Val Val Gly Pro Ile Val Leu Phe Val Ile<br>        1190                  1195                  1200 | 3609 |
| gat cgc ata att ggt ttg atg caa tat tac aaa aaa tta gaa att<br>Asp Arg Ile Ile Gly Leu Met Gln Tyr Tyr Lys Lys Leu Glu Ile<br>        1205                  1210                  1215 | 3654 |
| gta aac gca gaa atc ctt cca tca gat att ata tac atc gag tac<br>Val Asn Ala Glu Ile Leu Pro Ser Asp Ile Ile Tyr Ile Glu Tyr<br>        1220                  1225                  1230 | 3699 |
| cgt cgt cca aga gag ttt aaa tat aaa tca gga caa tgg gtt act<br>Arg Arg Pro Arg Glu Phe Lys Tyr Lys Ser Gly Gln Trp Val Thr<br>        1235                  1240                  1245 | 3744 |
| gta tca tca cca tca ata tca tgt acc ttt aat gaa tct cac gca<br>Val Ser Ser Pro Ser Ile Ser Cys Thr Phe Asn Glu Ser His Ala<br>        1250                  1255                  1260 | 3789 |

```
ttc tcg att gcc tca agt cca cag gat gag aat atg aag ttg tat      3834
Phe Ser Ile Ala Ser Ser Pro Gln Asp Glu Asn Met Lys Leu Tyr
    1265                1270                1275 ata aaa gca gtt gga cca tgg aca tgg aag ttg aga agc gaa ttg      3879
Ile Lys Ala Val Gly Pro Trp Thr Trp Lys Leu Arg Ser Glu Leu
1280                1285                1290 ata aga tca ttg aat aca gga tcg cca ttt cca tta atc cat atg      3924
Ile Arg Ser Leu Asn Thr Gly Ser Pro Phe Pro Leu Ile His Met
    1295                1300                1305 aaa gga cca tat ggt gat ggt aac caa gaa tgg atg gat tat gaa      3969
Lys Gly Pro Tyr Gly Asp Gly Asn Gln Glu Trp Met Asp Tyr Glu
1310                1315                1320 gtt gca ata atg gtt gga gca gga atc gga gtg act cca tat gca      4014
Val Ala Ile Met Val Gly Ala Gly Ile Gly Val Thr Pro Tyr Ala
    1325                1330                1335 tcg aca ctt gtt gat ctt gta caa cga aca tca agt gac tca ttt      4059
Ser Thr Leu Val Asp Leu Val Gln Arg Thr Ser Ser Asp Ser Phe
1340                1345                1350 cac aga gtt cgt tgc cgt aaa gta tat ttc cta tgg gtg tgc tca      4104
His Arg Val Arg Cys Arg Lys Val Tyr Phe Leu Trp Val Cys Ser
    1355                1360                1365 act cac aag aac tat gaa tgg ttt gtg gat gtg ctc aag aac gtg      4149
Thr His Lys Asn Tyr Glu Trp Phe Val Asp Val Leu Lys Asn Val
1370                1375                1380 gaa gac caa gca agg tcg gga att ttg gag aca cat atc ttt gtc      4194
Glu Asp Gln Ala Arg Ser Gly Ile Leu Glu Thr His Ile Phe Val
    1385                1390                1395 act cag acg ttc cac aag ttt gat ttg aga act act atg ctt tac      4239
Thr Gln Thr Phe His Lys Phe Asp Leu Arg Thr Thr Met Leu Tyr
1400                1405                1410 att tgc gag aag cac ttc cgt gcc acc aac tca gga att tca atg      4284
Ile Cys Glu Lys His Phe Arg Ala Thr Asn Ser Gly Ile Ser Met
    1415                1420                1425 ttt act ggt ctc cac gct aag aac cat ttc gga cgg ccc aac ttc      4329
Phe Thr Gly Leu His Ala Lys Asn His Phe Gly Arg Pro Asn Phe
1430                1435                1440 aaa gct ttc ttc caa ttt att cag agt gaa cat aag gag caa tcc      4374
Lys Ala Phe Phe Gln Phe Ile Gln Ser Glu His Lys Glu Gln Ser
    1445                1450                1455 aaa atc gga gtg ttc agt tgt gga cct gta aac ttg aat gaa agt      4419
Lys Ile Gly Val Phe Ser Cys Gly Pro Val Asn Leu Asn Glu Ser
1460                1465                1470 ata gct gaa gga tgt gca gat gcc aac cga caa cga gat gct cct      4464
Ile Ala Glu Gly Cys Ala Asp Ala Asn Arg Gln Arg Asp Ala Pro
    1475                1480                1485 tca ttt gca cat cgc ttt gaa acg ttc taa                          4494
Ser Phe Ala His Arg Phe Glu Thr Phe
1490                1495
```

<210> SEQ ID NO 4
<211> LENGTH: 1497
<212> TYPE: PRT
<213> ORGANISM: Caenorhabditis elegans

<400> SEQUENCE: 4

```
Met Arg Ser Lys His Val Leu Tyr Ile Ala Ile Leu Phe Ser Ser Ile
1               5                   10                  15

Phe Gly Gly Lys Gly Ile Gln Gln Asn Glu Glu Phe Gln Arg Tyr Asp
            20                  25                  30
```

```
Gly Trp Tyr Asn Asn Leu Ala Asn Ser Glu Trp Gly Ser Ala Gly Ser
         35                  40                  45

Arg Leu His Arg Asp Ala Arg Ser Tyr Tyr Ser Asp Gly Val Tyr Ser
     50                  55                  60

Val Asn Asn Ser Leu Pro Ser Ala Arg Glu Leu Ser Asp Ile Leu Phe
 65              70                  75                      80

Lys Gly Glu Ser Gly Ile Pro Asn Thr Arg Gly Cys Thr Thr Leu Leu
             85                  90                  95

Ala Phe Phe Ser Gln Val Val Ala His Glu Ile Met Gln Ser Asn Gly
             100                 105                 110

Val Ser Cys Pro Leu Glu Thr Leu Lys Ile Gln Val Pro Leu Cys Asp
         115                 120                 125

Asn Val Phe Asp Lys Glu Cys Glu Gly Lys Thr Glu Ile Pro Phe Thr
 130                 135                 140

Arg Ala Lys Tyr Asp Lys Ala Thr Gly Asn Gly Leu Asn Ser Pro Arg
 145                 150                 155                 160

Glu Gln Ile Asn Glu Arg Thr Ser Trp Ile Asp Gly Ser Phe Ile Tyr
                 165                 170                 175

Gly Thr Thr Gln Pro Trp Val Ser Ser Leu Arg Ser Phe Lys Gln Gly
             180                 185                 190

Arg Leu Ala Glu Gly Val Pro Gly Tyr Pro Pro Leu Asn Asn Pro His
         195                 200                 205

Ile Pro Leu Asn Asn Pro Ala Pro Pro Gln Val His Arg Leu Met Ser
 210                 215                 220

Pro Asp Arg Leu Phe Met Leu Gly Asp Ser Arg Val Asn Glu Asn Pro
 225                 230                 235                 240

Gly Leu Leu Ser Phe Gly Leu Ile Leu Phe Arg Trp His Asn Tyr Asn
                 245                 250                 255

Ala Asn Gln Ile His Arg Glu His Pro Asp Trp Thr Asp Glu Gln Ile
             260                 265                 270

Phe Gln Ala Ala Arg Arg Leu Val Ile Ala Ser Met Gln Lys Ile Ile
         275                 280                 285

Ala Tyr Asp Phe Val Pro Gly Leu Leu Gly Glu Asp Val Arg Leu Ser
 290                 295                 300

Asn Tyr Thr Lys Tyr Met Pro His Val Pro Pro Gly Ile Ser His Ala
 305                 310                 315                 320

Phe Gly Ala Ala Ala Phe Arg Phe Pro His Ser Ile Val Pro Pro Ala
             325                 330                 335

Met Leu Leu Arg Lys Arg Gly Asn Lys Cys Glu Phe Arg Thr Glu Val
         340                 345                 350

Gly Gly Tyr Pro Ala Leu Arg Leu Cys Gln Asn Trp Trp Asn Ala Gln
         355                 360                 365

Asp Ile Val Lys Glu Tyr Ser Val Asp Glu Ile Ile Leu Gly Met Ala
 370                 375                 380

Ser Gln Ile Ala Glu Arg Asp Asp Asn Ile Val Val Glu Asp Leu Arg
 385                 390                 395                 400

Asp Tyr Ile Phe Gly Pro Met His Phe Ser Arg Leu Asp Val Val Ala
                 405                 410                 415

Ser Ser Ile Met Arg Gly Arg Asp Asn Gly Val Pro Pro Tyr Asn Glu
             420                 425                 430

Leu Arg Arg Thr Phe Gly Leu Ala Pro Lys Thr Trp Glu Thr Met Asn
         435                 440                 445

Glu Asp Phe Tyr Lys Lys His Thr Ala Lys Val Glu Lys Leu Lys Glu
```

-continued

```
        450                 455                 460
Leu Tyr Gly Gly Asn Ile Leu Tyr Leu Asp Ala Tyr Val Gly Gly Met
465                 470                 475                 480

Leu Glu Gly Gly Glu Asn Gly Pro Gly Glu Leu Phe Lys Glu Ile Ile
                485                 490                 495

Lys Asp Gln Phe Thr Arg Ile Arg Asp Gly Asp Arg Phe Trp Phe Glu
                500                 505                 510

Asn Lys Leu Asn Gly Leu Phe Thr Asp Glu Glu Val Gln Met Ile His
                515                 520                 525

Ser Ile Thr Leu Arg Asp Ile Ile Lys Ala Thr Thr Asp Ile Asp Glu
530                 535                 540

Thr Met Leu Gln Lys Asp Val Phe Phe Lys Glu Gly Asp Pro Cys
545                 550                 555                 560

Pro Gln Pro Phe Gln Val Asn Thr Thr Gly Leu Glu Pro Cys Val Pro
                565                 570                 575

Phe Met Gln Ser Thr Tyr Trp Thr Asp Asn Asp Thr Thr Tyr Val Phe
                580                 585                 590

Thr Leu Ile Gly Leu Ala Cys Val Pro Leu Ile Cys Tyr Gly Ile Gly
                595                 600                 605

Arg Tyr Leu Val Asn Arg Arg Ile Ala Ile Gly His Asn Ser Ala Cys
                610                 615                 620

Asp Ser Leu Thr Thr Asp Phe Ala Asn Asp Asp Cys Gly Ala Lys Gly
625                 630                 635                 640

Asp Ile Tyr Gly Val Asn Ala Leu Glu Trp Leu Gln Glu Glu Tyr Ile
                645                 650                 655

Arg Gln Val Arg Ile Glu Ile Glu Asn Thr Thr Leu Ala Val Lys Lys
                660                 665                 670

Pro Arg Gly Gly Ile Leu Arg Lys Ile Arg Phe Glu Thr Gly Gln Lys
                675                 680                 685

Ile Glu Leu Phe His Ser Met Pro Asn Pro Ser Ala Met His Gly Pro
690                 695                 700

Phe Val Leu Leu Ser Gln Lys Asn Asn His His Leu Val Ile Arg Leu
705                 710                 715                 720

Ser Ser Asp Arg Asp Leu Ser Lys Phe Leu Asp Gln Ile Arg Gln Ala
                725                 730                 735

Ala Ser Gly Ile Asn Ala Glu Val Ile Ile Lys Asp Glu Glu Asn Ser
                740                 745                 750

Ile Leu Leu Ser Gln Ala Ile Thr Lys Glu Arg Arg Gln Asp Arg Leu
                755                 760                 765

Asp Leu Phe Phe Arg Glu Ala Tyr Ala Lys Ala Phe Asn Asp Ser Glu
770                 775                 780

Leu Gln Asp Ser Glu Thr Ser Phe Asp Ser Ser Asn Asp Ile Leu
785                 790                 795                 800

Asn Glu Thr Ile Ser Arg Glu Glu Leu Ala Ser Ala Met Gly Met Lys
                805                 810                 815

Ala Asn Asn Glu Phe Val Lys Arg Met Phe Ala Met Ile Ala Lys His
                820                 825                 830

Asn Glu Asp Ser Leu Ser Phe Asn Glu Phe Leu Thr Val Leu Arg Glu
                835                 840                 845

Phe Val Asn Ala Pro Gln Lys Gln Lys Leu Gln Thr Leu Phe Lys Met
                850                 855                 860

Cys Asp Leu Glu Gly Lys Asn Lys Val Leu Arg Lys Asp Leu Ala Glu
865                 870                 875                 880
```

```
Leu Val Lys Ser Leu Asn Gln Thr Ala Gly Val His Ile Thr Glu Ser
            885                 890                 895

Val Gln Leu Arg Leu Phe Asn Glu Val Leu His Tyr Ala Gly Val Ser
            900                 905                 910

Asn Asp Ala Lys Tyr Leu Thr Tyr Asp Asp Phe Asn Ala Leu Phe Ser
            915                 920                 925

Asp Ile Pro Asp Lys Gln Pro Val Gly Leu Pro Phe Asn Arg Lys Asn
            930                 935                 940

Tyr Gln Pro Ser Ile Gly Glu Thr Ser Ser Leu Asn Ser Phe Ala Val
945                 950                 955                 960

Val Asp Arg Ser Ile Asn Ser Ser Ala Pro Leu Thr Leu Ile His Lys
            965                 970                 975

Val Ser Ala Phe Leu Glu Thr Tyr Arg Gln His Val Phe Ile Val Phe
            980                 985                 990

Cys Phe Val Ala Ile Asn Leu Val Leu Phe Phe Glu Arg Phe Trp His
            995                 1000                1005

Tyr Arg Tyr Met Ala Glu Asn Arg Asp Leu Arg Arg Val Met Gly
    1010                1015                1020

Ala Gly Ile Ala Ile Thr Arg Gly Ala Ala Gly Ala Leu Ser Phe
    1025                1030                1035

Cys Met Ala Leu Ile Leu Leu Thr Val Cys Arg Asn Ile Ile Thr
    1040                1045                1050

Leu Leu Arg Glu Thr Val Ile Ala Gln Tyr Ile Pro Phe Asp Ser
    1055                1060                1065

Ala Ile Ala Phe His Lys Ile Val Ala Leu Phe Ala Ala Phe Trp
    1070                1075                1080

Ala Thr Leu His Thr Val Gly His Cys Val Asn Phe Tyr His Val
    1085                1090                1095

Gly Thr Gln Ser Gln Glu Gly Leu Ala Cys Leu Phe Gln Glu Ala
    1100                1105                1110

Phe Phe Gly Ser Asn Phe Leu Pro Ser Ile Ser Tyr Trp Phe Phe
    1115                1120                1125

Ser Thr Ile Thr Gly Leu Thr Gly Ile Ala Leu Val Ala Val Met
    1130                1135                1140

Cys Ile Ile Tyr Val Phe Ala Leu Pro Cys Phe Ile Lys Arg Ala
    1145                1150                1155

Tyr His Ala Phe Arg Leu Thr His Leu Leu Asn Ile Ala Phe Tyr
    1160                1165                1170

Ala Leu Thr Leu Leu His Gly Leu Pro Lys Leu Leu Asp Ser Pro
    1175                1180                1185

Lys Phe Gly Tyr Tyr Val Val Gly Pro Ile Val Leu Phe Val Ile
    1190                1195                1200

Asp Arg Ile Ile Gly Leu Met Gln Tyr Tyr Lys Lys Leu Glu Ile
    1205                1210                1215

Val Asn Ala Glu Ile Leu Pro Ser Asp Ile Ile Tyr Ile Glu Tyr
    1220                1225                1230

Arg Arg Pro Arg Glu Phe Lys Tyr Lys Ser Gly Gln Trp Val Thr
    1235                1240                1245

Val Ser Ser Pro Ser Ile Ser Cys Thr Phe Asn Glu Ser His Ala
    1250                1255                1260

Phe Ser Ile Ala Ser Ser Pro Gln Asp Glu Asn Met Lys Leu Tyr
    1265                1270                1275
```

```
Ile Lys Ala Val Gly Pro Trp Thr Trp Lys Leu Arg Ser Glu Leu
1280            1285                1290

Ile Arg Ser Leu Asn Thr Gly Ser Pro Phe Pro Leu Ile His Met
1295            1300                1305

Lys Gly Pro Tyr Gly Asp Gly Asn Gln Glu Trp Met Asp Tyr Glu
1310            1315                1320

Val Ala Ile Met Val Gly Ala Gly Ile Gly Val Thr Pro Tyr Ala
1325            1330                1335

Ser Thr Leu Val Asp Leu Val Gln Arg Thr Ser Ser Asp Ser Phe
1340            1345                1350

His Arg Val Arg Cys Arg Lys Val Tyr Phe Leu Trp Val Cys Ser
1355            1360                1365

Thr His Lys Asn Tyr Glu Trp Phe Val Asp Val Leu Lys Asn Val
1370            1375                1380

Glu Asp Gln Ala Arg Ser Gly Ile Leu Glu Thr His Ile Phe Val
1385            1390                1395

Thr Gln Thr Phe His Lys Phe Asp Leu Arg Thr Thr Met Leu Tyr
1400            1405                1410

Ile Cys Glu Lys His Phe Arg Ala Thr Asn Ser Gly Ile Ser Met
1415            1420                1425

Phe Thr Gly Leu His Ala Lys Asn His Phe Gly Arg Pro Asn Phe
1430            1435                1440

Lys Ala Phe Phe Gln Phe Ile Gln Ser Glu His Lys Glu Gln Ser
1445            1450                1455

Lys Ile Gly Val Phe Ser Cys Gly Pro Val Asn Leu Asn Glu Ser
1460            1465                1470

Ile Ala Glu Gly Cys Ala Asp Ala Asn Arg Gln Arg Asp Ala Pro
1475            1480                1485

Ser Phe Ala His Arg Phe Glu Thr Phe
1490            1495
```

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
gaagtggtgg gaggcgaaga cata                                        24

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
cctgtcatac ctgggacggt ctgg                                        24

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gagcacagtg agatgcctgt tcag                                    24

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
ggaaggcagc agagagcaat gatg                                    24

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
aggtgggatg cggatgttga g                                       21

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
acatctgcga gcggcacttc caga                                    24

<210> SEQ ID NO 11
<211> LENGTH: 25
<212> TYPE: DNA
<213> ORGANISM: Artificial Sequence
<220> FEATURE:
<223> OTHER INFORMATION: Synthetic primer

<400> SEQUENCE: 11
agctcgtcaa caggcaggac cgagc                                   25

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
tctccatcag aatccacctt aggc                                    24

<210> SEQ ID NO 13
<211> LENGTH: 7
<212> TYPE: DNA
<213> ORGANISM: Artificial Sequence
<220> FEATURE:
<223> OTHER INFORMATION: Synthetic primer

<400> SEQUENCE: 13 ggcatgc                                                        7

<210> SEQ ID NO 14
<211> LENGTH: 34
<212> TYPE: DNA
<213> ORGANISM: Artificial Sequence

```
-continued

<220> FEATURE:
<223> OTHER INFORMATION: Synthetic primer

<400> SEQUENCE: 14
attcgtcgac aaatgcgctc aaaacatgtg ctgt                              34

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
aactttgtgg atcaaagtta gcg                                         23

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
ttggattagc attttgctat ggaa                                        24

<210> SEQ ID NO 17
<211> LENGTH: 32
<212> TYPE: DNA
<213> ORGANISM: Artificial Sequence
<220> FEATURE:
<223> OTHER INFORMATION: Synthetic primer

<400> SEQUENCE: 17
gagcggccgc gaacgtttca aagcgatgtg ca                               32

<210> SEQ ID NO 18
<211> LENGTH: 6
<212> TYPE: PRT
<213> ORGANISM: Artificial Sequence
<220> FEATURE:
<223> OTHER INFORMATION: Binding helix
<220> FEATURE:
<221> NAME/KEY: MISC_FEATURE
<222> LOCATION: (1)..(6)
<223> OTHER INFORMATION: Any "X" = any amino acid

<400> SEQUENCE: 18

Gly Xaa Gly Xaa Xaa Pro
1               5

<210> SEQ ID NO 19
<211> LENGTH: 24
<212> TYPE: DNA
<213> ORGANISM: Artificial Sequence
<220> FEATURE:
<223> OTHER INFORMATION: Synthetic primer

<400> SEQUENCE: 19
gcaggacatc aaccctgcac tctc                                        24

<210> SEQ ID NO 20
<211> LENGTH: 24
<212> TYPE: DNA
<213> ORGANISM: Artificial Sequence
<220> FEATURE:
<223> OTHER INFORMATION: Synthetic primer
```

```
<400> SEQUENCE: 20
ctgccatcta ccacacggat ctgc                                          24

<210> SEQ ID NO 21
<211> LENGTH: 27
<212> TYPE: DNA
<213> ORGANISM: Artificial Sequence
<220> FEATURE:
<223> OTHER INFORMATION: Synthetic primer

<400> SEQUENCE: 21
gccctcaacc taagcagctc acaactg                                       27

<210> SEQ ID NO 22
<211> LENGTH: 24
<212> TYPE: DNA
<213> ORGANISM: Artificial Sequence
<220> FEATURE:
<223> OTHER INFORMATION: Synthetic primer

<400> SEQUENCE: 22
gagcacagtg agatgcctgt tcag                                          24

<210> SEQ ID NO 23
<211> LENGTH: 32
<212> TYPE: DNA
<213> ORGANISM: Artificial Sequence
<220> FEATURE:
<223> OTHER INFORMATION: Synthetic primer

<400> SEQUENCE: 23
gctagagctc ttcagtttgc tatggaattg gc                                 32

<210> SEQ ID NO 24
<211> LENGTH: 25
<212> TYPE: DNA
<213> ORGANISM: Artificial Sequence
<220> FEATURE:
<223> OTHER INFORMATION: Synthetic primer

<400> SEQUENCE: 24
cataaaggat gaggagaatt ctgtg                                         25

<210> SEQ ID NO 25
<211> LENGTH: 33
<212> TYPE: DNA
<213> ORGANISM: Artificial Sequence
<220> FEATURE:
<223> OTHER INFORMATION: Synthetic primer

<400> SEQUENCE: 25
gctagagctc ggctactact acgttgttgg acc                                33

<210> SEQ ID NO 26
<211> LENGTH: 31
<212> TYPE: DNA
<213> ORGANISM: Artificial Sequence
<220> FEATURE:
<223> OTHER INFORMATION: Synthetic primer

<400> SEQUENCE: 26
gactgaagga cttgtggaac gtctgagtga c                                  31

<210> SEQ ID NO 27
```

```
<211> LENGTH: 32
<212> TYPE: DNA
<213> ORGANISM: Artificial Sequence
<220> FEATURE:
<223> OTHER INFORMATION: Synthetic primer

<400> SEQUENCE: 27
gctagagctc acatttgcga gaagcacttc cg                                32

<210> SEQ ID NO 28
<211> LENGTH: 32
<212> TYPE: DNA
<213> ORGANISM: Artificial Sequence
<220> FEATURE:
<223> OTHER INFORMATION: Synthetic primer

<400> SEQUENCE: 28
gtgtgaattc agcgatgtgc aaatgaagga gc                                32

<210> SEQ ID NO 29
<211> LENGTH: 36
<212> TYPE: DNA
<213> ORGANISM: Artificial Sequence
<220> FEATURE:
<223> OTHER INFORMATION: Synthetic primer

<400> SEQUENCE: 29
agtcgaagct tagcatgtca aagtccggag ttcagt                            36

<210> SEQ ID NO 30
<211> LENGTH: 36
<212> TYPE: DNA
<213> ORGANISM: Artificial Sequence
<220> FEATURE:
<223> OTHER INFORMATION: Synthetic primer

<400> SEQUENCE: 30
ctagtggatc cgcattgctc gtgcgcctta gagttt                            36

<210> SEQ ID NO 31
<211> LENGTH: 593
<212> TYPE: PRT
<213> ORGANISM: Homo sapiens

<400> SEQUENCE: 31

Met Leu Arg Ala Arg Pro Glu Ala Leu Met Leu Leu Gly Ala Leu Leu
1               5                   10                  15

Thr Gly Ser Leu Gly Pro Ser Gly Ser Gln Asp Ala Leu Ser Leu Pro
                20                  25                  30

Trp Glu Val Gln Arg Tyr Asp Gly Trp Phe Asn Asn Leu Arg His His
            35                  40                  45

Glu Arg Gly Ala Val Gly Cys Arg Leu Gln Arg Arg Val Pro Ala Asn
        50                  55                  60

Tyr Ala Asp Gly Val Tyr Gln Ala Leu Glu Glu Pro Gln Leu Pro Asn
65                  70                  75                  80

Pro Arg Arg Leu Ser Asn Ala Ala Thr Arg Gly Ile Ala Gly Leu Pro
                85                  90                  95

Ser Leu His Asn Arg Thr Val Leu Gly Val Phe Phe Gly Tyr His Val
                100                 105                 110

Leu Ser Asp Val Val Ser Val Glu Thr Pro Gly Cys Pro Ala Glu Phe
            115                 120                 125

Leu Asn Ile Arg Ile Pro Pro Gly Asp Leu Val Phe Asp Pro Asp Gln
```

-continued

```
            130                 135                 140
Arg Gly Asp Val Val Leu Pro Phe Gln Arg Ser Arg Trp Asp Pro Glu
145                 150                 155                 160

Thr Gly Arg Ser Pro Ser Asn Pro Arg Asp Leu Ala Asn Gln Val Thr
                165                 170                 175

Gly Trp Leu Asp Gly Ser Ala Ile Tyr Gly Ser Ser His Ser Trp Ser
                180                 185                 190

Asp Ala Leu Arg Ser Phe Ser Gly Gln Leu Ala Ser Gly Pro Asp
            195                 200                 205

Pro Ala Phe Pro Arg Asp Ser Gln Asn Pro Leu Leu Met Trp Ala Ala
210                 215                 220

Pro Asp Pro Ala Thr Gly Gln Asn Gly Pro Arg Gly Leu Tyr Ala Phe
225                 230                 235                 240

Gly Ala Glu Arg Gly Asn Arg Glu Pro Phe Leu Gln Ala Leu Gly Leu
                245                 250                 255

Leu Trp Phe Arg Tyr His Asn Leu Trp Ala Gln Arg Leu Ala Arg Gln
                260                 265                 270

His Pro Asp Trp Glu Asp Glu Leu Phe Gln His Ala Arg Lys Arg
            275                 280                 285

Val Ile Ala Thr Tyr Gln Asn Ile Ala Val Tyr Glu Trp Leu Pro Ser
290                 295                 300

Phe Leu Gln Lys Thr Leu Pro Glu Tyr Thr Gly Tyr Arg Pro Phe Leu
305                 310                 315                 320

Asp Pro Ser Ile Ser Pro Glu Phe Val Val Ala Ser Glu Gln Phe Phe
                325                 330                 335

Ser Thr Met Val Pro Pro Gly Val Tyr Met Arg Asn Ala Ser Cys His
                340                 345                 350

Phe Arg Lys Val Leu Asn Lys Gly Phe Gln Ser Ser Gln Ala Leu Arg
            355                 360                 365

Val Cys Asn Asn Tyr Trp Ile Arg Glu Asn Pro Asn Leu Asn Ser Thr
370                 375                 380

Gln Glu Val Asn Glu Leu Leu Leu Gly Met Ala Ser Gln Ile Ser Glu
385                 390                 395                 400

Leu Glu Asp Asn Ile Val Val Glu Asp Leu Arg Asp Tyr Trp Pro Gly
                405                 410                 415

Pro Gly Lys Phe Ser Arg Thr Asp Tyr Val Ala Ser Ile Gln Arg
            420                 425                 430

Gly Arg Asp Met Gly Leu Pro Ser Tyr Gln Ala Leu Leu Ala Phe
            435                 440                 445

Gly Leu Asp Ile Pro Arg Asn Trp Ser Asp Leu Asn Pro Asn Val Asp
450                 455                 460

Pro Gln Val Leu Glu Ala Thr Ala Ala Leu Tyr Asn Gln Asp Leu Ser
465                 470                 475                 480

Gln Leu Glu Leu Leu Leu Gly Gly Leu Leu Glu Ser His Gly Asp Pro
                485                 490                 495

Gly Pro Leu Phe Ser Ala Ile Val Leu Asp Gln Phe Val Arg Leu Arg
                500                 505                 510

Asp Gly Asp Arg Tyr Trp Phe Glu Asn Thr Arg Asn Gly Leu Phe Ser
                515                 520                 525

Lys Lys Glu Ile Glu Asp Ile Arg Asn Thr Thr Leu Arg Asp Val Leu
            530                 535                 540

Val Ala Val Ile Asn Ile Asp Pro Ser Ala Leu Gln Pro Asn Val Phe
545                 550                 555                 560
```

```
Val Trp His Lys Gly Ala Pro Cys Pro Gln Pro Lys Gln Leu Thr Thr
                565                 570                 575

Asp Gly Leu Pro Gln Cys Ala Pro Leu Thr Val Leu Asp Phe Phe Glu
            580                 585                 590

Gly

<210> SEQ ID NO 32
<211> LENGTH: 590
<212> TYPE: PRT
<213> ORGANISM: Caenorhabditis elegans

<400> SEQUENCE: 32

Met Arg Ser Lys His Val Leu Tyr Ile Ala Ile Leu Phe Ser Ser Ile
1               5                   10                  15

Phe Gly Gly Lys Gly Ile Gln Gln Asn Glu Glu Phe Gln Arg Tyr Asp
            20                  25                  30

Gly Trp Tyr Asn Asn Leu Ala Asn Ser Glu Trp Gly Ser Ala Gly Ser
        35                  40                  45

Arg Leu His Arg Asp Ala Arg Ser Tyr Tyr Ser Asp Gly Val Tyr Ser
    50                  55                  60

Val Asn Asn Ser Leu Pro Ser Ala Arg Glu Leu Ser Asp Ile Leu Phe
65                  70                  75                  80

Lys Gly Glu Ser Gly Ile Pro Asn Thr Arg Gly Cys Thr Thr Leu Leu
                85                  90                  95

Ala Phe Phe Ser Gln Val Val Ala His Glu Ile Met Gln Ser Asn Gly
            100                 105                 110

Val Ser Cys Pro Leu Glu Thr Leu Lys Ile Gln Val Pro Leu Cys Asp
        115                 120                 125

Asn Val Phe Asp Lys Glu Cys Glu Gly Lys Thr Glu Ile Pro Phe Thr
    130                 135                 140

Arg Ala Lys Tyr Asp Lys Ala Thr Gly Asn Gly Leu Asn Ser Pro Arg
145                 150                 155                 160

Glu Gln Ile Asn Glu Arg Thr Ser Trp Ile Asp Gly Ser Phe Ile Tyr
                165                 170                 175

Gly Thr Thr Gln Pro Trp Val Ser Ser Leu Arg Ser Phe Lys Gln Gly
            180                 185                 190

Arg Leu Ala Glu Gly Val Pro Gly Tyr Pro Pro Leu Asn Asn Pro His
        195                 200                 205

Ile Pro Leu Asn Asn Pro Ala Pro Pro Gln Val His Arg Leu Met Ser
    210                 215                 220

Pro Asp Arg Leu Phe Met Leu Gly Asp Ser Arg Val Asn Glu Asn Pro
225                 230                 235                 240

Gly Leu Leu Ser Phe Gly Leu Ile Leu Phe Arg Trp His Asn Tyr Asn
                245                 250                 255

Ala Asn Gln Ile His Arg Glu His Pro Asp Trp Thr Asp Glu Gln Ile
            260                 265                 270

Phe Gln Ala Ala Arg Arg Leu Val Ile Ala Ser Met Gln Lys Ile Ile
        275                 280                 285

Ala Tyr Asp Phe Val Pro Gly Leu Leu Gly Glu Asp Val Arg Leu Ser
    290                 295                 300

Asn Tyr Thr Lys Tyr Met Pro His Val Pro Pro Gly Ile Ser His Ala
305                 310                 315                 320

Phe Gly Ala Ala Ala Phe Arg Phe Pro His Ser Ile Val Pro Pro Ala
                325                 330                 335
```

```
Met Leu Leu Arg Lys Arg Gly Asn Lys Cys Glu Phe Arg Thr Glu Val
            340                 345                 350

Gly Gly Tyr Pro Ala Leu Arg Leu Cys Gln Asn Trp Trp Asn Ala Gln
        355                 360                 365

Asp Ile Val Lys Glu Tyr Ser Val Asp Glu Ile Ile Leu Gly Met Ala
    370                 375                 380

Ser Gln Ile Ala Glu Arg Asp Asp Asn Ile Val Val Glu Asp Leu Arg
385                 390                 395                 400

Asp Tyr Ile Phe Gly Pro Met His Phe Ser Arg Leu Asp Val Val Ala
                405                 410                 415

Ser Ser Ile Met Arg Gly Arg Asp Asn Gly Val Pro Pro Tyr Asn Glu
            420                 425                 430

Leu Arg Arg Thr Phe Gly Leu Ala Pro Lys Thr Trp Glu Thr Met Asn
        435                 440                 445

Glu Asp Phe Tyr Lys Lys His Thr Ala Lys Val Glu Lys Leu Lys Glu
    450                 455                 460

Leu Tyr Gly Gly Asn Ile Leu Tyr Leu Asp Ala Tyr Val Gly Gly Met
465                 470                 475                 480

Leu Glu Gly Gly Glu Asn Gly Pro Gly Glu Leu Phe Lys Glu Ile Ile
                485                 490                 495

Lys Asp Gln Phe Thr Arg Ile Arg Asp Gly Asp Arg Phe Trp Phe Glu
            500                 505                 510

Asn Lys Leu Asn Gly Leu Phe Thr Asp Glu Glu Val Gln Met Ile His
        515                 520                 525

Ser Ile Thr Leu Arg Asp Ile Ile Lys Ala Thr Thr Asp Ile Asp Glu
    530                 535                 540

Thr Met Leu Gln Lys Asp Val Phe Phe Phe Lys Glu Gly Asp Pro Cys
545                 550                 555                 560

Pro Gln Pro Phe Gln Val Asn Thr Thr Gly Leu Glu Pro Cys Val Pro
                565                 570                 575

Phe Met Gln Ser Thr Tyr Trp Thr Asp Asn Asp Thr Thr Tyr
            580                 585                 590

<210> SEQ ID NO 33
<211> LENGTH: 559
<212> TYPE: PRT
<213> ORGANISM: Homo sapiens

<400> SEQUENCE: 33

Gly Met Cys Asn Asn Arg Arg Ser Pro Thr Leu Gly Ala Ser Asn Arg
1               5                   10                  15

Ala Phe Val Arg Trp Leu Pro Ala Glu Tyr Glu Asp Gly Phe Ser Leu
            20                  25                  30

Pro Tyr Gly Trp Thr Pro Gly Val Lys Arg Asn Gly Phe Pro Val Ala
        35                  40                  45

Leu Ala Arg Ala Val Ser Asn Glu Ile Val Arg Phe Pro Thr Asp Gln
    50                  55                  60

Leu Thr Pro Asp Gln Glu Arg Ser Leu Met Phe Met Gln Trp Gly Gln
65                  70                  75                  80

Leu Leu Asp His Asp Leu Asp Phe Thr Pro Glu Pro Ala Ala Arg Ala
                85                  90                  95

Ser Phe Val Thr Gly Val Asn Cys Glu Thr Ser Cys Val Gln Gln Pro
            100                 105                 110

Pro Cys Phe Pro Leu Lys Ile Pro Pro Asn Asp Pro Arg Ile Lys Asn
```

-continued

```
                115                 120                 125
Gln Ala Asp Cys Ile Pro Phe Phe Arg Ser Cys Pro Ala Cys Pro Gly
    130                 135                 140

Ser Asn Ile Thr Ile Arg Asn Gln Ile Asn Ala Leu Thr Ser Phe Val
145                 150                 155                 160

Asp Ala Ser Met Val Tyr Gly Ser Glu Glu Pro Leu Ala Arg Asn Leu
                165                 170                 175

Arg Asn Met Ser Asn Gln Leu Gly Leu Leu Ala Val Asn Gln Arg Phe
            180                 185                 190

Gln Asp Asn Gly Arg Ala Leu Leu Pro Phe Asp Asn Leu His Asp Asp
        195                 200                 205

Pro Cys Leu Leu Thr Asn Arg Ser Ala Arg Ile Pro Cys Phe Leu Ala
    210                 215                 220

Gly Asp Thr Arg Ser Ser Glu Met Pro Glu Leu Thr Ser Met His Thr
225                 230                 235                 240

Leu Leu Leu Arg Glu His Asn Arg Leu Ala Thr Glu Leu Lys Ser Leu
                245                 250                 255

Asn Pro Arg Trp Asp Gly Glu Arg Leu Tyr Gln Glu Ala Arg Lys Ile
            260                 265                 270

Val Gly Ala Met Val Gln Ile Ile Thr Tyr Arg Asp Tyr Leu Pro Leu
        275                 280                 285

Val Leu Gly Pro Thr Ala Met Arg Lys Tyr Leu Pro Thr Tyr Arg Ser
    290                 295                 300

Tyr Asn Asp Ser Val Asp Pro Arg Ile Ala Asn Val Phe Thr Asn Ala
305                 310                 315                 320

Phe Arg Tyr Gly His Thr Leu Ile Gln Pro Phe Met Phe Arg Leu Asp
                325                 330                 335

Asn Arg Tyr Gln Pro Met Glu Pro Asn Pro Arg Val Pro Leu Ser Arg
            340                 345                 350

Val Phe Phe Ala Ser Trp Arg Val Leu Glu Gly Gly Ile Asp Pro
        355                 360                 365

Ile Leu Arg Gly Leu Met Ala Thr Pro Ala Lys Leu Asn Arg Gln Asn
    370                 375                 380

Gln Ile Ala Val Asp Glu Ile Arg Glu Arg Leu Phe Glu Gln Val Met
385                 390                 395                 400

Arg Ile Gly Leu Asp Leu Pro Ala Leu Asn Met Gln Arg Ser Arg Asp
                405                 410                 415

His Gly Leu Pro Gly Tyr Asn Ala Trp Arg Arg Phe Cys Gly Leu Pro
            420                 425                 430

Gln Pro Glu Thr Val Gly Gln Leu Gly Thr Val Leu Arg Asn Leu Lys
        435                 440                 445

Leu Ala Arg Lys Leu Met Glu Gln Tyr Gly Thr Pro Asn Asn Ile Asp
    450                 455                 460

Ile Trp Met Gly Gly Val Ser Glu Pro Leu Lys Arg Lys Gly Arg Val
465                 470                 475                 480

Gly Pro Leu Leu Ala Cys Ile Ile Gly Thr Gln Phe Arg Lys Leu Arg
                485                 490                 495

Asp Gly Asp Arg Phe Trp Trp Glu Asn Glu Gly Val Phe Ser Met Gln
            500                 505                 510

Gln Arg Gln Ala Leu Ala Gln Ile Ser Leu Pro Arg Ile Ile Cys Asp
        515                 520                 525

Asn Thr Gly Ile Thr Thr Val Ser Lys Asn Asn Ile Phe Met Ser Asn
    530                 535                 540
```

Ser Tyr Pro Arg Asp Phe Val Asn Cys Ser Thr Leu Pro Ala Leu
545                 550                 555

<210> SEQ ID NO 34
<211> LENGTH: 572
<212> TYPE: PRT
<213> ORGANISM: Homo sapiens

<400> SEQUENCE: 34

Gly Ala Cys Asn Asn Arg Asp His Pro Arg Trp Gly Ala Ser Asn Thr
1               5                   10                  15

Ala Leu Ala Arg Trp Leu Pro Pro Val Tyr Glu Asp Gly Phe Ser Gln
            20                  25                  30

Pro Arg Gly Trp Asn Pro Gly Phe Leu Tyr Asn Gly Phe Pro Leu Pro
        35                  40                  45

Pro Val Arg Glu Val Thr Arg His Val Ile Gln Val Ser Asn Glu Val
    50                  55                  60

Val Thr Asp Asp Arg Tyr Ser Asp Leu Leu Met Ala Trp Gly Gln
65                  70                  75                  80

Tyr Ile Asp His Asp Ile Ala Phe Thr Pro Gln Ser Thr Ser Lys Ala
                85                  90                  95

Ala Phe Gly Gly Gly Ala Asp Cys Gln Met Thr Cys Glu Asn Gln Asn
            100                 105                 110

Pro Cys Phe Pro Ile Gln Leu Pro Glu Glu Ala Arg Pro Ala Ala Gly
        115                 120                 125

Thr Ala Cys Leu Pro Phe Tyr Arg Ser Ser Ala Ala Cys Gly Thr Gly
    130                 135                 140

Asp Gln Gly Ala Leu Phe Gly Asn Leu Ser Thr Ala Asn Pro Arg Gln
145                 150                 155                 160

Gln Met Asn Gly Leu Thr Ser Phe Leu Asp Ala Ser Thr Val Tyr Gly
                165                 170                 175

Ser Ser Pro Ala Leu Glu Arg Gln Leu Arg Asn Trp Thr Ser Ala Glu
            180                 185                 190

Gly Leu Leu Arg Val His Ala Arg Leu Arg Asp Ser Gly Arg Ala Tyr
        195                 200                 205

Leu Pro Phe Val Pro Pro Arg Ala Pro Ala Ala Cys Ala Pro Glu Pro
    210                 215                 220

Gly Ile Pro Gly Glu Thr Arg Gly Pro Cys Phe Leu Ala Gly Asp Gly
225                 230                 235                 240

Arg Ala Ser Glu Val Pro Ser Leu Thr Ala Leu His Thr Leu Trp Leu
                245                 250                 255

Arg Glu His Asn Arg Leu Ala Ala Ala Leu Lys Ala Leu Asn Ala His
            260                 265                 270

Trp Ser Ala Asp Ala Val Tyr Gln Glu Ala Arg Lys Val Val Gly Ala
        275                 280                 285

Leu His Gln Ile Ile Thr Leu Arg Asp Tyr Ile Pro Arg Ile Leu Gly
    290                 295                 300

Pro Glu Ala Phe Gln Gln Tyr Val Gly Pro Tyr Glu Gly Tyr Asp Ser
305                 310                 315                 320

Thr Ala Asn Pro Thr Val Ser Asn Val Phe Ser Thr Ala Ala Phe Arg
                325                 330                 335

Phe Gly His Ala Thr Ile His Pro Leu Val Arg Arg Leu Asp Ala Ser
            340                 345                 350

Phe Gln Glu His Pro Asp Leu Pro Gly Leu Trp Leu His Gln Ala Phe

```
                    355                 360                 365
Phe Ser Pro Trp Thr Leu Leu Arg Gly Gly Leu Asp Pro Leu Ile
        370                 375                 380
Arg Gly Leu Leu Ala Arg Pro Ala Lys Leu Gln Val Gln Asp Gln Leu
385                 390                 395                 400
Met Asn Glu Glu Leu Thr Glu Arg Leu Phe Val Leu Ser Asn Ser Ser
                405                 410                 415
Thr Leu Asp Leu Ala Ser Ile Asn Leu Gln Arg Gly Arg Asp His Gly
            420                 425                 430
Leu Pro Gly Tyr Asn Glu Trp Arg Glu Phe Cys Gly Leu Pro Arg Leu
        435                 440                 445
Glu Thr Pro Ala Asp Leu Ser Thr Ala Ile Ala Ser Arg Ser Val Ala
    450                 455                 460
Asp Lys Ile Leu Asp Leu Tyr Lys His Pro Asp Asn Ile Asp Val Trp
465                 470                 475                 480
Leu Gly Gly Leu Ala Glu Asn Phe Leu Pro Arg Ala Arg Thr Gly Pro
                485                 490                 495
Leu Phe Ala Cys Leu Ile Gly Lys Gln Met Lys Ala Leu Arg Asp Gly
                500                 505                 510
Asp Trp Phe Trp Trp Glu Asn Ser His Val Phe Thr Asp Ala Gln Arg
            515                 520                 525
Arg Glu Leu Glu Lys His Ser Leu Ser Arg Val Ile Cys Asp Asn Thr
        530                 535                 540
Gly Leu Thr Arg Val Pro Met Asp Ala Phe Gln Val Gly Lys Phe Pro
545                 550                 555                 560
Glu Asp Phe Glu Ser Cys Asp Ser Ile Pro Gly Met
                565                 570

<210> SEQ ID NO 35
<211> LENGTH: 566
<212> TYPE: PRT
<213> ORGANISM: Homo sapiens

<400> SEQUENCE: 35

Gly Arg Cys Asn Asn Lys Arg Arg Pro Leu Leu Gly Ala Ser Asn Gln
1               5                   10                  15
Ala Leu Ala Arg Trp Leu Pro Ala Glu Tyr Glu Asp Gly Leu Ser Leu
            20                  25                  30
Pro Phe Gly Trp Thr Pro Ser Arg Arg Asn Gly Phe Leu Leu Pro
        35                  40                  45
Leu Val Arg Ala Val Ser Asn Gln Ile Val Arg Phe Pro Asn Glu Arg
50                  55                  60
Leu Thr Ser Asp Arg Gly Arg Ala Leu Met Phe Met Gln Trp Gly Gln
65                  70                  75                  80
Phe Ile Asp His Asp Leu Asp Phe Ser Pro Glu Ser Pro Ala Arg Val
                85                  90                  95
Ala Phe Thr Ala Gly Val Asp Cys Glu Arg Thr Cys Ala Gln Leu Pro
            100                 105                 110
Pro Cys Phe Pro Ile Lys Ile Pro Pro Asn Asp Pro Arg Ile Lys Asn
        115                 120                 125
Gln Arg Asp Cys Ile Pro Phe Phe Arg Ser Ala Pro Ser Cys Pro Gln
    130                 135                 140
Asn Lys Asn Arg Val Arg Asn Gln Ile Asn Ala Leu Thr Ser Phe Val
145                 150                 155                 160
```

```
Asp Ala Ser Met Val Tyr Gly Ser Glu Val Ser Leu Ser Leu Arg Leu
            165                 170                 175

Arg Asn Arg Thr Asn Tyr Leu Gly Leu Leu Ala Ile Asn Gln Arg Phe
        180                 185                 190

Gln Asp Asn Gly Arg Ala Leu Leu Pro Phe Asp Asn Leu His Asp Asp
            195                 200                 205

Pro Cys Leu Leu Thr Asn Arg Ser Ala Arg Ile Pro Cys Phe Leu Ala
    210                 215                 220

Gly Asp Thr Arg Ser Thr Glu Thr Pro Lys Leu Ala Ala Met His Thr
225                 230                 235                 240

Leu Phe Met Arg Glu His Asn Arg Leu Ala Thr Glu Leu Arg Arg Leu
            245                 250                 255

Asn Pro Arg Trp Asn Gly Asp Lys Leu Tyr Asn Glu Ala Arg Lys Ile
        260                 265                 270

Met Gly Ala Met Val Gln Ile Ile Thr Tyr Arg Asp Phe Leu Pro Leu
            275                 280                 285

Val Leu Gly Lys Ala Arg Ala Arg Arg Thr Leu Gly His Tyr Arg Gly
    290                 295                 300

Tyr Cys Ser Asn Val Asp Pro Arg Val Ala Asn Val Phe Thr Leu Ala
305                 310                 315                 320

Phe Arg Phe Gly His Thr Met Leu Gln Pro Phe Met Phe Arg Leu Asp
            325                 330                 335

Ser Gln Tyr Arg Ala Ser Ala Pro Asn Ser His Val Pro Leu Ser Ser
        340                 345                 350

Ala Phe Phe Ala Ser Trp Arg Ile Val Tyr Glu Gly Ile Asp Pro
            355                 360                 365

Ile Leu Arg Gly Leu Met Ala Thr Pro Ala Lys Leu Asn Arg Gln Asp
    370                 375                 380

Ala Met Leu Val Asp Glu Leu Arg Asp Arg Leu Phe Arg Gln Val Arg
385                 390                 395                 400

Arg Ile Gly Leu Asp Leu Ala Ala Leu Asn Met Gln Arg Ser Arg Asp
            405                 410                 415

His Gly Leu Pro Gly Tyr Asn Ala Trp Arg Arg Phe Cys Gly Leu Ser
        420                 425                 430

Gln Pro Arg Asn Leu Ala Gln Leu Ser Arg Val Leu Lys Asn Gln Asp
    435                 440                 445

Leu Ala Arg Lys Phe Leu Asn Leu Tyr Gly Thr Pro Asp Asn Ile Asp
450                 455                 460

Ile Trp Ile Gly Ala Ile Ala Glu Pro Leu Leu Pro Gly Ala Arg Glu
465                 470                 475                 480

Pro Leu Leu Pro Gly Ala Arg Val Gly Pro Leu Leu Ala Cys Leu Phe
            485                 490                 495

Glu Asn Gln Phe Arg Arg Ala Arg Asp Gly Asp Arg Phe Trp Trp Gln
        500                 505                 510

Lys Arg Gly Val Phe Thr Lys Arg Gln Arg Lys Ala Leu Ser Arg Ile
    515                 520                 525

Ser Leu Ser Arg Ile Ile Cys Asp Asn Thr Gly Ile Thr Thr Val Ser
530                 535                 540

Arg Asp Ile Phe Arg Ala Asn Ile Tyr Pro Arg Gly Phe Val Asn Cys
545                 550                 555                 560

Ser Arg Ile Pro Arg Leu
            565
```

<210> SEQ ID NO 36
<211> LENGTH: 620
<212> TYPE: PRT
<213> ORGANISM: Bos sp.

<400> SEQUENCE: 36

```
Met Trp Val Cys Leu Gln Leu Pro Val Phe Leu Ala Ser Val Thr Leu
1               5                   10                  15

Phe Glu Val Ala Ala Ser Asp Thr Ile Ala Gln Ala Ala Ser Thr Thr
                20                  25                  30

Thr Ile Ser Asp Ala Val Ser Lys Val Lys Ile Gln Val Asn Lys Ala
            35                  40                  45

Phe Leu Asp Ser Arg Thr Arg Leu Lys Thr Thr Leu Gly Asp Cys Asn
    50                  55                  60

Asn Arg Arg Ser Pro Ala Leu Gly Ala Ala Asn Arg Ala Leu Ala Arg
65                  70                  75                  80

Trp Leu Pro Ala Glu Tyr Glu Asp Gly Leu Ala Leu Pro Phe Gly Trp
                85                  90                  95

Thr Gln Arg Lys Thr Arg Asn Gly Phe Arg Val Pro Leu Ala Arg Glu
            100                 105                 110

Val Ser Asn Lys Ile Val Gly Tyr Leu Asp Glu Gly Val Leu Asp
        115                 120                 125

Gln Asn Arg Ser Leu Leu Phe Met Gln Trp Gly Gln Ile Val Asp His
    130                 135                 140

Asp Leu Asp Phe Ala Pro Glu Thr Glu Leu Gly Ser Asn Glu His Ser
145                 150                 155                 160

Lys Thr Gln Cys Glu Glu Tyr Cys Ile Gln Gly Asp Asn Cys Phe Pro
                165                 170                 175

Ile Met Phe Pro Lys Asn Asp Pro Lys Leu Lys Thr Gln Gly Lys Cys
            180                 185                 190

Met Pro Phe Phe Arg Ala Gly Phe Val Cys Pro Thr Pro Pro Tyr Gln
        195                 200                 205

Ser Leu Ala Arg Glu Gln Ile Asn Ala Val Thr Ser Phe Leu Asp Ala
    210                 215                 220

Ser Leu Val Tyr Gly Ser Glu Pro Ser Leu Ala Ser Arg Leu Arg Asn
225                 230                 235                 240

Leu Ser Ser Pro Leu Gly Leu Met Ala Val Asn Gln Glu Ala Trp Asp
                245                 250                 255

His Gly Leu Ala Tyr Leu Pro Phe Asn Asn Lys Lys Pro Ser Pro Cys
            260                 265                 270

Glu Phe Ile Asn Thr Thr Ala Arg Val Pro Cys Phe Leu Ala Gly Asp
        275                 280                 285

Phe Arg Ala Ser Glu Gln Ile Leu Leu Ala Thr Ala His Thr Leu Leu
    290                 295                 300

Leu Arg Glu His Asn Arg Leu Ala Arg Glu Leu Lys Lys Leu Asn Pro
305                 310                 315                 320

His Trp Asn Gly Glu Lys Leu Tyr Gln Glu Ala Arg Lys Ile Leu Gly
                325                 330                 335

Ala Phe Ile Gln Ile Ile Thr Phe Arg Asp Tyr Leu Pro Ile Val Leu
            340                 345                 350

Gly Ser Glu Met Gln Lys Trp Ile Pro Pro Tyr Gln Gly Tyr Asn Asn
        355                 360                 365

Ser Val Asp Pro Arg Ile Ser Asn Val Phe Thr Phe Ala Phe Arg Phe
    370                 375                 380
```

```
Gly His Met Glu Val Pro Ser Thr Val Ser Arg Leu Asp Glu Asn Tyr
385                 390                 395                 400

Gln Pro Trp Gly Pro Glu Ala Glu Leu Pro Leu His Thr Leu Phe Phe
            405                 410                 415

Asn Thr Trp Arg Ile Ile Lys Asp Gly Ile Asp Pro Leu Val Arg
            420                 425                 430

Gly Leu Leu Ala Lys Lys Ser Lys Leu Met Asn Gln Asp Lys Met Val
            435                 440                 445

Thr Ser Glu Leu Arg Asn Lys Leu Phe Gln Pro Thr His Lys Ile His
450                 455                 460

Gly Phe Asp Leu Ala Ala Ile Asn Leu Gln Arg Cys Arg Asp His Gly
465                 470                 475                 480

Met Pro Gly Tyr Asn Ser Trp Arg Gly Phe Cys Gly Leu Ser Gln Pro
                485                 490                 495

Lys Thr Leu Lys Gly Leu Gln Thr Val Leu Lys Asn Lys Ile Leu Ala
            500                 505                 510

Lys Lys Leu Met Asp Leu Tyr Lys Thr Pro Asp Asn Ile Asp Ile Trp
            515                 520                 525

Ile Gly Gly Asn Ala Glu Pro Met Val Glu Arg Gly Arg Val Gly Pro
530                 535                 540

Leu Leu Ala Cys Leu Leu Gly Arg Gln Phe Gln Gln Ile Arg Asp Gly
545                 550                 555                 560

Asp Arg Phe Trp Trp Glu Asn Pro Gly Val Phe Thr Glu Lys Gln Arg
                565                 570                 575

Asp Ser Leu Gln Lys Val Ser Phe Ser Arg Leu Ile Cys Asp Asn Thr
            580                 585                 590

His Ile Thr Lys Val Pro Leu His Ala Phe Gln Ala Asn Asn Tyr Pro
            595                 600                 605

His Asp Phe Val Asp Cys Ser Thr Val Asp Lys Leu
610                 615                 620

<210> SEQ ID NO 37
<211> LENGTH: 545
<212> TYPE: PRT
<213> ORGANISM: Drosophila sp.

<400> SEQUENCE: 37

Gly Thr Cys Asn Asn Leu Gln His Pro Thr Trp Gly Ala Ser Leu Thr
1               5                   10                  15

Ala Phe Arg Arg Leu Ala Pro Pro Ile Tyr Glu Asn Gly Phe Ser Met
            20                  25                  30

Pro Val Gly Trp Thr Lys Gly Met Leu Tyr Ser Gly His Ala Lys Pro
        35                  40                  45

Ser Ala Arg Leu Val Ser Thr Ser Leu Val Ala Thr Lys Glu Ile Thr
    50                  55                  60

Pro Asp Ala Arg Ile Thr His Met Val Met Gln Trp Gly Gln Phe Leu
65                  70                  75                  80

Asp His Asp Leu Asp His Ala Ile Pro Ser Val Ser Ser Glu Ser Trp
                85                  90                  95

Asp Gly Ile Asp Cys Lys Lys Ser Cys Glu Met Ala Pro Pro Cys Tyr
            100                 105                 110

Pro Ile Glu Val Pro Pro Asn Asp Pro Arg Val Arg Asn Arg Arg Cys
        115                 120                 125

Ile Asp Val Val Arg Ser Ser Ala Ile Cys Gly Ser Gly Met Thr Ser
130                 135                 140
```

```
Leu Phe Phe Asp Ser Val Gln His Arg Glu Gln Ile Asn Gln Leu Thr
145                 150                 155                 160

Ser Tyr Ile Asp Ala Ser Gln Val Tyr Gly Tyr Ser Thr Ala Phe Ala
                165                 170                 175

Gln Leu Ala Arg Asn Leu Thr Ser Gln Glu Gly Leu Leu Arg Val Gly
            180                 185                 190

Val His Phe Pro Arg Gln Lys Asp Met Leu Pro Phe Ala Ala Pro Gln
        195                 200                 205

Asp Gly Met Asp Cys Arg Arg Asn Leu Asp Glu Asn Thr Met Ser Cys
    210                 215                 220

Phe Val Ser Gly Asp Ile Arg Val Asn Glu Gln Val Gly Leu Leu Ala
225                 230                 235                 240

Met His Thr Ile Trp Met Arg Glu His Asn Arg Ile Ala Ser Lys Leu
                245                 250                 255

Lys Gln Ile Asn Ser His Trp Asp Gly Asp Thr Leu Tyr Gln Glu Ala
            260                 265                 270

Arg Lys Ile Val Gly Ala Gln Met Gln His Ile Thr Phe Lys Gln Trp
        275                 280                 285

Leu Pro Leu Ile Ile Gly Glu Ser Gly Met Glu Met Met Ser Glu Tyr
    290                 295                 300

Gln Ala Thr Ser Pro Thr Glu Ser Ser Ile Ala Asn Glu Phe Ala Thr
305                 310                 315                 320

Ala Ala Leu Arg Phe Gly His Thr Ile Ile Asn Pro Ile Leu His Arg
                325                 330                 335

Leu Asn Glu Thr Phe Gln Pro Ile Pro Gln Gly His Leu Leu Leu His
            340                 345                 350

Lys Ala Phe Phe Ala Pro Trp Arg Leu Ala Tyr Glu Gly Gly Val Asp
        355                 360                 365

Pro Leu Met Arg Gly Phe Leu Ala Val Pro Ala Lys Leu Lys Thr Pro
    370                 375                 380

Asp Gln Asn Leu Asn Thr Glu Leu Thr Glu Lys Leu Phe Gln Thr Ala
385                 390                 395                 400

His Ala Val Ala Leu Asp Leu Ala Ala Ile Asn Ile Gln Arg Gly Arg
                405                 410                 415

Asp His Gly Met Pro Gly Tyr Asn Val Tyr Arg Lys Leu Cys Asn Leu
            420                 425                 430

Thr Val Ala Gln Asp Phe Glu Asp Leu Ala Gly Glu Ile Ser Ser Ala
        435                 440                 445

Glu Ile Arg Gln Lys Met Lys Glu Leu Tyr Gly His Pro Asp Asn Val
    450                 455                 460

Asp Val Trp Leu Gly Gly Ile Leu Glu Asp Gln Val Glu Gly Gly Lys
465                 470                 475                 480

Val Gly Pro Leu Phe Gln Cys Leu Leu Val Glu Gln Phe Arg Arg Leu
                485                 490                 495

Arg Asp Gly Asp Arg Leu Tyr Tyr Glu Asn Pro Gly Val Phe Ser Pro
            500                 505                 510

Glu Gln Leu Thr Gln Ile Lys Gln Ala Asn Phe Gly Arg Val Leu Cys
        515                 520                 525

Asp Val Gly Asp Asn Phe Asp Gln Val Thr Glu Asn Val Phe Ile Leu
    530                 535                 540

Ala
545
```

```
<210> SEQ ID NO 38
<211> LENGTH: 538
<212> TYPE: PRT
<213> ORGANISM: Homo sapiens

<400> SEQUENCE: 38

Gly Trp Tyr Asn Asn Leu Met Glu His Arg Trp Ser Lys Gly Ser
1               5                   10                  15

Arg Leu Gln Arg Leu Val Pro Ala Ser Tyr Ala Asp Gly Val Tyr Gln
            20                  25                  30

Pro Leu Gly Glu Pro His Leu Pro Asn Pro Arg Asp Leu Ser Asn Thr
        35                  40                  45

Ile Ser Arg Gly Pro Ala Gly Leu Ala Ser Leu Arg Asn Arg Thr Val
50                  55                  60

Leu Gly Val Phe Phe Gly Tyr His Val Leu Ser Asp Leu Val Ser Val
65                  70                  75                  80

Glu Thr Pro Gly Cys Pro Ala Glu Phe Leu Asn Ile Arg Ile Pro Pro
                85                  90                  95

Gly Asp Pro Met Phe Asp Pro Asp Gln Arg Gly Asp Val Val Leu Pro
            100                 105                 110

Phe Gln Arg Ser Arg Trp Asp Pro Glu Thr Gly Arg Ser Pro Ser Asn
        115                 120                 125

Pro Arg Asp Pro Ala Asn Gln Val Thr Gly Trp Leu Asp Gly Ser Ala
    130                 135                 140

Ile Tyr Gly Ser Ser His Ser Trp Ser Asp Ala Leu Arg Ser Phe Ser
145                 150                 155                 160

Arg Gly Gln Leu Ala Ser Gly Pro Asp Pro Ala Phe Pro Arg Asp Ser
                165                 170                 175

Gln Asn Pro Leu Leu Met Trp Ala Ala Pro Asp Pro Ala Thr Gly Gln
            180                 185                 190

Asn Gly Pro Arg Gly Leu Tyr Ala Phe Gly Ala Glu Arg Gly Asn Arg
        195                 200                 205

Glu Pro Phe Leu Gln Ala Leu Gly Leu Leu Trp Phe Arg Tyr His Asn
    210                 215                 220

Leu Trp Ala Gln Arg Leu Ala Arg Gln His Pro Asp Trp Glu Asp Glu
225                 230                 235                 240

Glu Leu Phe Gln His Ala Arg Lys Arg Val Ile Ala Thr Tyr Gln Asn
                245                 250                 255

Ile Ala Val Tyr Glu Trp Leu Pro Ser Phe Leu Gln Lys Thr Leu Pro
            260                 265                 270

Glu Tyr Thr Gly Tyr Arg Pro Phe Leu Asp Pro Ser Ile Ser Ser Glu
        275                 280                 285

Phe Val Ala Ala Ser Glu Gln Phe Leu Ser Thr Met Val Pro Pro Gly
    290                 295                 300

Val Tyr Met Arg Asn Ala Ser Cys His Phe Gln Gly Val Ile Asn Arg
305                 310                 315                 320

Asn Ser Ser Val Ser Arg Ala Leu Arg Val Cys Asn Ser Tyr Trp Ser
                325                 330                 335

Arg Glu His Pro Ser Leu Gln Ser Ala Glu Val Asp Ala Leu Leu
            340                 345                 350

Leu Gly Met Ala Ser Gln Ile Ala Glu Arg Glu Asp His Val Leu Val
        355                 360                 365

Glu Asp Val Arg Asp Phe Trp Pro Gly Pro Leu Lys Phe Ser Arg Thr
    370                 375                 380
```

```
Asp His Leu Ala Ser Cys Leu Gln Arg Gly Arg Asp Leu Gly Leu Pro
385                 390                 395                 400

Ser Tyr Thr Lys Ala Arg Ala Ala Leu Gly Leu Ser Pro Ile Thr Arg
                405                 410                 415

Trp Gln Asp Ile Asn Pro Ala Leu Ser Arg Ser Asn Asp Thr Val Leu
            420                 425                 430

Glu Ala Thr Ala Ala Leu Tyr Asn Gln Asp Leu Ser Trp Leu Glu Leu
            435                 440                 445

Leu Pro Gly Gly Leu Leu Glu Ser His Arg Asp Pro Gly Pro Leu Phe
        450                 455                 460

Ser Thr Ile Val Leu Glu Gln Phe Val Arg Leu Arg Asp Gly Asp Arg
465                 470                 475                 480

Tyr Trp Phe Glu Asn Thr Arg Asn Gly Leu Phe Ser Lys Lys Glu Ile
                485                 490                 495

Glu Glu Ile Arg Asn Thr Thr Leu Gln Asp Val Leu Val Ala Val Ile
                500                 505                 510

Asn Ile Asp Pro Ser Ala Leu Gln Pro Asn Val Phe Val Trp His Lys
                515                 520                 525

Gly Asp Pro Cys Pro Gln Pro Arg Gln Leu
        530                 535

<210> SEQ ID NO 39
<211> LENGTH: 16
<212> TYPE: PRT
<213> ORGANISM: Caenorhabditis elegans

<400> SEQUENCE: 39

Arg Lys Arg Gly Asn Lys Cys Glu Phe Arg Thr Glu Val Gly Gly Tyr
1               5                   10                  15
```